(12) United States Patent
Rentschler et al.

(10) Patent No.: US 9,339,169 B2
(45) Date of Patent: May 17, 2016

(54) ROBOTIC CAPSULE ENDOSCOPE FOR MINIMALLY INVASIVE SURGICAL PROCEDURES, MICRO-PATTERNED TREADS FOR FRICTION ENHANCEMENT OF A ROBOTIC CAPSULE ENDOSCOPE IN A BIOLOGICAL ENVIRONMENT, AND PROCESS FOR FABRICATION OF MICRO-TREADS

(71) Applicant: The Regents of the University of Colorado, a body corporate, Denver, CO (US)

(72) Inventors: Mark Edwin Rentschler, Boulder, CO (US); Levin John Sliker, Colorado Springs, CO (US); Benjamin Spencer Terry, Lincoln, NE (US); Madalyn Diane Kern, Broomfield, CO (US); Jonathan Schoen, Denver, CO (US)

(73) Assignee: The Regents of University of Colorado, a body corporate, Denver, CO (US)

( * ) Notice: Subject to any disclaimer, the term of this patent is extended or adjusted under 35 U.S.C. 154(b) by 618 days.

(21) Appl. No.: 13/692,743

(22) Filed: Dec. 3, 2012

(65) Prior Publication Data

US 2013/0172671 A1 Jul. 4, 2013

Related U.S. Application Data

(60) Provisional application No. 61/566,611, filed on Dec. 3, 2011.

(51) Int. Cl.
| | |
|---|---|
| *A61B 1/00* | (2006.01) |
| *B29C 65/50* | (2006.01) |
| *B32B 3/30* | (2006.01) |
| *A61B 1/04* | (2006.01) |
| *B32B 25/20* | (2006.01) |

(52) U.S. Cl.
CPC ............ *A61B 1/00156* (2013.01); *A61B 1/0011* (2013.01); *A61B 1/0016* (2013.01);

(Continued)

(58) Field of Classification Search
CPC .. A61B 1/00156; A61B 1/0016; A61B 1/041; A61B 1/0011; B32B 25/20; B32B 3/30; B32B 2433/00; B32B 2255/205; B32B 2255/10; B29C 65/50; Y10T 428/24479
USPC ............ 428/156; 600/101, 109; 156/137, 247
See application file for complete search history.

(56) References Cited

U.S. PATENT DOCUMENTS

| | | |
|---|---|---|
| 6,240,312 B1 | 5/2001 | Alfano et al. |
| 7,042,184 B2 | 5/2006 | Oleynikov et al. |

(Continued)

OTHER PUBLICATIONS

Karagozler, M.E., et al., "Miniature Endoscopic Capsule Robot using Biomimetic Micro-Patterned Adhesives" paper published in "Biomedical Robotics and Biomechatronics," 2006, pp. 105-111, found on http://ieeexplore.ieee.org/stamp/stamp.jsp?tp=&arnumber=1639068.*

(Continued)

*Primary Examiner* — Maria Veronica Ewald
*Assistant Examiner* — Brian Handville
(74) *Attorney, Agent, or Firm* — James A. Sheridan; Sheridan Law, LLC

(57) ABSTRACT

Micro-patterned treads for endoscopes are disclosed. In an embodiment, the treads include a micro-patterned surface and a roller engaging surface. Micro-patterned tread bearing robotic capsule endoscopes are disclosed. In one embodiment, the endoscope includes a housing, a motor, a geared drive, rollers, and at least one micro-patterned tread. Methods of fabricating closed loop treads are disclosed. In an embodiment, a method includes forming a solid layer of PDMS on one side of double-sided tape and wrapping a micro-patterned PDMS strip together with the other side of the double-sided tape. In another embodiment, a method includes forming a timing belt PDMS strip on one side of double-sided tape and a micro-patterned PDMS strip together with the other side of the double-sided tape.

23 Claims, 56 Drawing Sheets

(52) U.S. Cl.
CPC ............... *A61B 1/041* (2013.01); *B29C 65/50* (2013.01); *B32B 3/30* (2013.01); *B32B 25/20* (2013.01); *B32B 2255/10* (2013.01); *B32B 2255/205* (2013.01); *B32B 2433/00* (2013.01); *Y10T 428/24479* (2015.01)

(56) References Cited

U.S. PATENT DOCUMENTS

| | | | |
|---|---|---|---|
| 7,126,303 | B2 | 10/2006 | Farritor et al. |
| 2011/0282150 | A1* | 11/2011 | Yamakawa et al. ........... 600/114 |
| 2011/0313249 | A1 | 12/2011 | Viola et al. |

OTHER PUBLICATIONS

American Elements, "Titanium Based Aluminum Iron Alloy," Sep. 13, 2011, found on https://web.archive.org/web/20110913105107/http://www.americanelements.com/titanium-aluminum-iron.html.*

Delcorte, A., et al., "Improvement of metal adhesion to silicone films: a ToF-SIMS study" report published in "Adhesion Aspects of Thin Films," 2004, VSP, vol. 2, pp. 1-12, found on http://perso.uclouvain.be/arnaud.delcorte/aatf203.pdf.*

* cited by examiner

| Tread Pattern | Maximum Drawbar Force (N) | Maximum Input Power (W) | Drawbar/ Normal Ratio |
|---|---|---|---|
| 0.10 N Normal Force | | | |
| 1) Equally spaced circular treads | 0.08 | 0.14 | 84% |
| 2) Straight rows circular treads | 0.06 | 0.10 | 61% |
| 3) Helical rows of circular treads | 0.06 | 0.12 | 55% |
| 4) Equally spaced square treads | 0.09 | 0.10 | 85% |
| 5) Equally spaced rhombus treads | 0.07 | 0.14 | 74% |
| 6) No pattern (flat) treads | 0.12 | 0.15 | 118% |
| 0.20 N Normal Force | | | |
| 1) Equally spaced circular treads | 0.14 | 0.16 | 69% |
| 2) Straight rows circular treads | 0.10 | 0.11 | 50% |
| 3) Helical rows of circular treads | 0.09 | 0.13 | 46% |
| 4) Equally spaced square treads | 0.14 | 0.12 | 69% |
| 5) Equally spaced rhombus treads | 0.13 | 0.16 | 64% |
| 6) No pattern (flat) treads | 0.22 | 0.20 | 111% |
| 0.30 N Normal Force | | | |
| 1) Equally spaced circular treads | 0.21 | 0.20 | 71% |
| 2) Straight rows circular treads | 0.16 | 0.14 | 55% |
| 3) Helical rows of circular treads | 0.16 | 0.16 | 52% |
| 4) Equally spaced square treads | 0.18 | 0.16 | 61% |
| 5) Equally spaced rhombus treads | 0.21 | 0.19 | 69% |
| 6) No pattern (flat) treads | 0.34 | 0.23 | 113% |
| 0.53 N Normal Force | | | |
| 1) Equally spaced circular treads | 0.33 | 0.22 | 62% |
| 2) Straight rows circular treads | 0.30 | 0.18 | 57% |
| 3) Helical rows of circular treads | 0.25 | 0.18 | 47% |
| 4) Equally spaced square treads | 0.31 | 0.20 | 58% |
| 5) Equally spaced rhombus treads | 0.35 | 0.23 | 65% |
| 6) No pattern (flat) treads | 0.37 | 0.23 | 70% |

TABLE 1

Figure 53

ROBOTIC CAPSULE ENDOSCOPE FOR MINIMALLY INVASIVE SURGICAL PROCEDURES, MICRO-PATTERNED TREADS FOR FRICTION ENHANCEMENT OF A ROBOTIC CAPSULE ENDOSCOPE IN A BIOLOGICAL ENVIRONMENT, AND PROCESS FOR FABRICATION OF MICRO-TREADS

REFERENCE TO PENDING PRIOR PATENT APPLICATION

This application claims the benefit under 35 USC 119(e) of U.S. Provisional Patent Application No. 61/566,611, filed Dec. 3, 2011 by Mark Edwin Rentschler, et al. for "ROBOTIC CAPSULE ENDOSCOPE FOR MINIMALLY INVASIVE SURGICAL PROCEDURES MICRO-PATTERNED TREADS FOR FRICTION ENHANCEMENT OF A ROBOTIC CAPSULE ENDOSCOPE IN A BIOLOGICAL ENVIRONMENT, AND PROCESS FOR FABRICATION OF MICRO-TREADS," which application is hereby incorporated by reference.

BACKGROUND

Minimally invasive surgery (MIS) is a broad encompassing term that includes keyhole type procedures from orthopedic joint repair to cardiac stent placement. MIS reduces collateral trauma by using tools inserted into the body through small incisions, which allows the patient to recover and resume a normal lifestyle quicker.

Laparoscopic MIS has been advanced by the introduction of the da Vinci surgical system by Intuitive Surgical, Inc. in the early 2000s. The da Vinci system is a tele-robotic system, which includes four robotic arms (that are external to the patient) that hold the laparoscope camera and instruments. Advantages of such surgical robotics include hand tremor reduction, additional articulations in surgical instruments end effectors, corrections for motion reversal, and motion scaling. However, since a da Vinci system is an extension of laparoscopy, it also suffers the inherit disadvantages of laparoscopy. First, these robots are situated outside the patient and, thus, remain subject to the dexterity limitations imposed by the use of long tools inserted through small incisions. Most studies suggest that current externally situated robotic systems offer little or no improvement over standard laparoscopic instruments in the performance of basic skills (Dakin, G. F. and Gagner, M., 2003. "Comparison of Laparoscopic Skills Performance Between Standard Instruments and Two Surgical Robotic Systems". Surgical Endoscopy, 17(4), April, pp. 574-579; and Nio, D., Bemelman, W. A., den Boer, K. T., Dunker, M. S., Gouma, D. J., and van Gulik, T. M., 2002. "Efficiency of Manual vs. Robotical (Zeus) Assisted Laparoscopic Surgery in the Performance of Standardized Tasks". Surgical Endoscopy, 16(3), March, pp. 412-415.) Furthermore, a limited range of motion for the robotic camera can still result in obstructed or incomplete visual feedback. Finally, a da Vinci system carries a significant price tag of approximately $1.5M (plus required inspection and scheduled maintenance costs), which limits such a system to be available only to larger hospitals. Currently, there are efforts focusing on developing next generation robots that improve mobility and sensing capability while reducing complexity and cost (Cavusoglu, M. C., Williams, W., Tendick, F., and Sastry, S. S., 2003. "Robotics for Telesurgery: Second Generation Berkeley/UCSF Laparoscopic Telesurgical Workstation and Looking Towards the Future Applications". Industrial Robot: An International Journal, 30(1), January, pp. 22-29; Cavusoglu, M. C., Tendick, F., and Sastry, S. S., 2001. "Telesurgery and Surgical Simulation Haptic Interfaces to Real and Virtual Surgical Environments". Touch in Virtual Environments, IMSC Series in Multimedia; Ang, W., 2004. Active Tremor Compensation in Handheld Instrument for Microsurgery. Tech Report SMU-R1—TR-04-28, Carnegie Mellon University, Pittsburgh, Pa., May; Riviere, C., Ang, W., and Khosla, P., 2003. "Toward Active Tremor Canceling in Handheld Microsurgical Instruments". IEEE Transactions on Robotics and Automation, 19(5), October, pp. 793-800; and Rosen, J., Lum, M. Trimble, D., Hannaford, B., and Sinanan, M., 2005. "Spherical Mechanism Analysis of a Surgical Robot for Minimally Invasive Surgery—Analytical and Experimental Approaches". Studies in Health Technology and Informatics, 111(1), January, pp. 422-428.)

In Vivo Laparoscopic Robots

As shown by the da Vinci system, the use of robots in MIS offers advantages, but these are limited when situating the robot outside the body. An alternative approach is to build smaller, low-cost, robotic devices or in vivo robots that can be placed inside the patient and near the surgical site.

A number of research groups are working on in vivo robotic devices for use in minimally invasive surgery. For example, a proof-of-concept design of an in vivo stereoscopic imaging system has been described by Miller et al. (Miller, A., Allen, P., and Fowler, D., 2004. "In vivo Stereoscopic Imaging System with 5 Degrees-of-Freedom for Minimal Access Surgery". Studies in Health Technology and Informatics, 12(1), January, pp. 234-240.) A second generation single camera pan and tilt prototype based on this initial concept is described in Hu et al. (Hu, T., Allen, P. K., and Fowler, D. L., 2008. "In vivo Pan/Tilt Endoscope with Integrated Light Source". Studies in Health Technology and Informatics, 132 (1), January, pp. 174-179), and is currently being evaluated in ex vivo and in vivo tests. Finally, the HeartLander robot employs a suction-based drive to move across the surface of the beating heart. (Patronik, N., Zenati, M. A., and Riviere, C., 2005. "Preliminary Evaluation of a Mobile Robotic Device for Navigation and Intervention on the Beating Heart". Computer Aided Surgery, 10(4), April, pp. 225-232; and Patronik, N., Zenati, M. A., and Riviere, C., 2004. "Crawling on the Heart: A Mobile Robotic Device for Minimally Invasive Cardiac Interventions". MICCAI, 3217, pp. 9-16.)

Others have previously developed a family of in vivo fixed-base and two-wheeled mobile robots (30 $cm^3$), and demonstrated that they can successfully operate within the insufflated abdominal cavity. (Rentschler, M., Iagnemma, K., Farritor, S., 2007. "Mechanical Design of Robotic In vivo Wheeled Mobility". ASME Journal of Mechanical Design, 129(10), October, pp. 1037-104.) These robots have been used to enhance the ability of laparoscopic surgeons to visualize the surgical field (M., Hadzialic, A., Dumpert, J., Platt, S. R., Farritor, S., and Oleynikov, D., 2004. "In vivo Robots for Laparoscopic Surgery". Studies in Health Technology and Informatics, 98, pp. 316-322; and Rentschler, M., Dumpert, J., Platt, S. R., Farritor, S., and Oleynikov, D., 2006. "Mobile In vivo Robots Can Assist In Abdominal Exploration". Surg. Endosc., 20(1), January, pp. 135-138), and to obtain tissue samples during a single-port liver biopsy in a porcine model. (Rentschler, M., Dumpert, J., Platt, S. R., Iagnemma, K., Oleynikov, D., and Farritor, S., 2007. "An In vivo Mobile Robot for Surgical Vision and Task Assistance". ASME Journal of Medical Devices, 1, pp. 23-29.)

In Vivo Gastrointestinal Robots

While this work has shown that in vivo mobility is possible, some such designs will be ineffective in un-insufflated cavities and cylindrical lumens (i.e. GI tract) where fundamentally different mobility approaches and designs are needed. In addition, insufflation in remote/trauma situations is extremely limited due to lack of equipment, and especially in cases where cavity trauma wounds may prevent proper sealing. Thus, an in vivo robot must also be able to traverse an uninsufflated cavity in order to be effective in remote/trauma environments.

The simplest such developed in vivo robotic mechanisms for the GI tract have been maneuverable endoscopes for colonoscopy and laparoscopy (Fukuda, T., Guo, S., Kosuge, K., Arai, F., Negoro, M., Nakabayashi, K., 1994. "Micro Active Catheter System with Multi Degrees of Freedom". *Proceedings of the IEEE International Conference on Robotics and Automation*, San Diego, Calif., 3, pp. 2290-2295; and Suzumori, K., Iikura, S., Tanaka, H., 1991. "Development of Flexible Microactuator and its Applications to Robotics Mechanisms," *Proceedings of the IEEE International Conference on Robotics and Automation*, Sacramento, Calif., 2, pp. 1622-1627.) These devices possess actuators to rotate the endoscope tip after it enters the body. Other in vivo robots have been developed to explore hollow cavities (e.g., the colon or esophagus) with locomotion systems based on 'inchworm' motion that use a series of grippers and extensors (Phee, L, Accoto, D., Menciassi, A., Stefanini, C., Carrozza, M., Dario, P, 2002. "Analysis and Development of Locomotion Devices for the Gastrointestinal Tract". *IEEE Transaction on Biomedical Engineering*, 49(6), June, pp. 613-616), rolling tracks (Flynn, A., Udayakumar, K., Barret, D., et al, 1995. "Tomorrow's Surgery; Micro-motors and Microrobots for Minimally Invasive Procedures". *Minimally Invasive Surgery & Allied Technologies*, 7(4), April, pp. 343-52), rolling stents (Breedveld, P., Danielle, E., Van Gorp, M., 2004. "Locomotion through the Intestine by means of Rolling Stents". *Proceedings of the ASME Design Engineering Technical Conferences*, Salt Lake City, Utah), or the rotational motion of a spiral-shaped body (Kim, Y. T., and Kim, D. E., 2010. "Novel Propelling Mechanisms Based on Friction Interaction for Endoscopic Robot". *Tribology Transactions*, 53(2), March, pp. 203-211). These devices apply radial pressure to the walls of the hollow cavities they explore. Dario et al. have recently described an endoscopic pill with an active locomotion system that uses legs to push against the gastrointestinal walls (Stefanini, C., Menciassi, A, and Dario, P., 2006. "Modeling and Experiments on a Legged Microrobot Locomoting in a Tubular, Compliant and Slippery Environment". *The International Journal of Robotics Research*, 25(5-6), May, pp. 551-560; Menciassi, A., Stefanini, C., Gorini, S., Pernorio, G., Kim, B., Park, J. O., Dario, P., 2004. "Locomotion of a Legged Capsule in the Gastrointestinal Tract: Theoretical Study and Preliminary Technological Results". *IEEE Int. Conf. on Engineering in Medicine and Biology*, San Francisco, Calif., pp. 2767-2770; and Valdastri, P., Webster, R. J., Quaglia, C., Quirini, M., Menciassi, A., and Dario, P., 2009. "A New Mechanism for Mesoscale Legged Locomotion in Compliant Tubular Environments". *IEEE Transactions on Robotics*, 25(5), October, pp. 1047-1057), a system that uses an external magnetic field to move the device through the intestine (Ciuti, G., Valdastri, P., Menciassi, A., and Dario, P., 2010. "Robotic magnetic steering and locomotion of capsule endoscope for diagnostic and surgical endoluminal procedures". *Robotica*, 28(2), March, pp. 199-207), a system that combines the two aforementioned systems (Simi, M., Valdastri, P., Quaglia, C., Menciassi, A., and Dario, P., 2010. "Design, Fabrication, and Testing of a Capsule With Hybrid Locomotion for Gastrointestinal Tract Exploration". *IEEE/ASME Transactions on Mechatronics*, 15(2), April, pp. 170-180), and a clamping system that uses shape memory alloys (Menciassi, A., Moglia, A., Gorini, S., Pernorio, G., Stefanini, C., and Dario, P., 2005. "Shape Memory Alloy Clamping Devices of a Capsule for Monitoring Tasks in the Gastrointestinal Tract". *J. Micromech Microeng*, 15(1), January, pp. 2045-2055.) Additionally, Dario et al. have described a modular robot that enters the body in subsections through the mouth, assembles itself within the gastric cavity for a surgical task, and then disassembles itself upon completion of the task for natural excretion (Harada, K., Oetomo, D., Susilo, E., Menciassi, A., Daney, D., Merlet, J., and Dario, P., 2010. "A reconfigurable modular robotic endoluminal surgical system: vision and preliminary results". *Robotica*, 28(2), March, pp. 171-183.)

SUMMARY

In an embodiment, there is provided a micro-patterned tread for a robotic capsule endoscope, the micro-patterned tread comprising a first side and a second side of the micro-patterned tread, the first side and the second side in opposition to one another; a micro-patterned surface disposed on the first side in a direction extending outwardly from the second side; and a roller engaging surface disposed on the second side in a direction extending outwardly from the first sides.

In another embodiment, there is provided a micro-patterned tread bearing robotic capsule endoscope, comprising an outer housing having a first end and a second end in opposition to one another; a motor disposed within the outer housing between the first end and the second end; a geared drive train in operable connection with the motor; a series of rollers supported by the outer housing; and at least one micro-patterned tread disposed on the series of rollers and in operable connection to the geared drive train so as to selectively drive the micro-patterned tread with the motor.

In yet another embodiment, there is provided a method of fabricating closed loop treads for a robotic capsule endoscope, the method comprising exposing a first side of double-sided tape by removing a backing paper; providing a thing layer of liquid PDMS to the first side of exposed double-sided tape; curing the liquid PDMS with heat to form a solid layer of PDMS; wrapping the solid layer of PDMS to overlap a first end of the double-sided tape to a second end of the double-sided tape; exposing a second side the double-sided tape by removing a backing paper; exposing the second side of the double-sided tape and a smooth side of a micro-patterned PDMS strip to $O_2$ plasma; and wrapping the smooth side of the micro-patterned PDMS strip together with the second side of the double-sided tape.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which:

FIG. 53 illustrates a set of results identified as Table 1.

DETAILED DESCRIPTION

Figure 1:
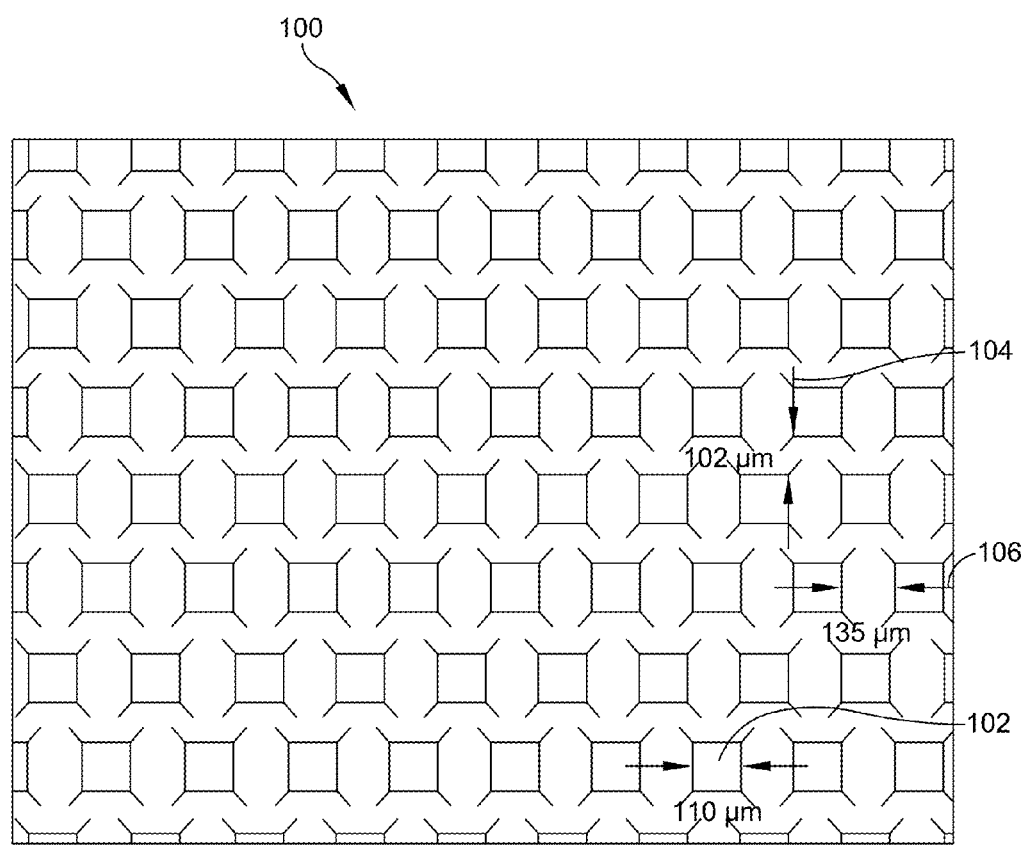
FIG. 1 illustrates an optical microscope view of micro-tread pattern mold with 1:2 aspect ratio (height:width)

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Despite revolutionary advances in many fields of medicine, there are no active mobile in vivo devices commercially available, or in use, today. Several research groups are actively looking at a number of mobility methods in a number of lumens, but little commercial work has been done. While robotic surgery is available today thanks to ex vivo robots such as the da Vinci surgical system, these methods are very expensive, require heavy external equipment, and are still constrained by entry incisions. An alternative approach may be to place the robot completely inside the patient. Such devices may enable non-invasive imaging and diagnostics. These devices may be significantly less expensive than current minimally invasive methods, without extensive support equipment, which may allow them to be also used routinely in the ER/trauma sites and remote locations. This disclosure provides micro-patterned treads that may enable mobile capsule crawlers inside the body. Current research efforts into providing contact locomotion using micro-tread tracks are explored including initial drawbar force generation experimental results, dynamic finite element analysis with these tread designs, and in vivo porcine evaluation and comparison of two leading tread designs.

Contact Locomotion

Various exemplary embodiments focus on tread-tissue interaction for wheel- or tank-based locomotion devices with simple drive trains. Such results may be applicable to other contact locomotion systems (i.e., wheels, tracks, inch-worms, etc.), in a multitude of cavities (i.e., abdominal, gastrointestinal, cardiac, pleural, etc.), for a variety of devices (i.e., in vivo robots, deployed colon and esophageal scopes, etc).

A mobile robot moving inside a collapsed lumen or insufflated cavity can be viewed in the general context of tread-surface interaction. Tread-surface interaction has been studied extensively in the robotics and automotive communities in the context of vehicle-terrain interaction. While these passenger car tire studies can yield insight into some aspects of tread-tissue interaction, the locomotion on deformable, fragile tissue involves rather different physical phenomena which yield different tread layouts. Contact methods and tread materials are disclosed that could ultimately enable locomotion in uninsufflated cavities, while maintaining a small footprint to conserve onboard space.

The use of endoscopic devices to diagnose and treat a range of gastrointestinal (GI) complications has recently grown. However, minimally invasive exploratory and surgical procedures within the gastrointestinal tract are currently generally limited to endoscopic techniques. When utilizing an endoscopic device, the surgeon has two options of entering the gastrointestinal tract, which are through the oral cavity, down the esophagus, through the stomach and into the small intestine via the duodenum, or through the anus, through the rectum, and into the colon and large intestine. A long 'push' endoscope entering the oral cavity can reach mid-small intestine, while an endoscope entering the anus can only reach the distal part of the small bowel. This leaves a section of the small intestine that is inaccessible by endoscope. The Pill-Cam™ (by Given Imaging of Yogneam, Isreael) is a device that contains an imaging system, which is swallowed by the patient. Although the PillCam can visualize the entire GI tract, it is a passive device, and therefore cannot be maneuvered through the tract.

The focus of exemplary various embodiments is not primarily development the endoscopic system, but rather a locomotion system for an active mobile device that can be placed completely inside the patient and that can provide mobility in both insufflated and collapsed lumens and cavities. This in vivo device, equipped with cameras and other sensors, could locate the surgical site of interest after performing diagnostic scans of the region. Therapy may be provided in the form of biopsy, or tissue dissection. Such an in vivo robot could ultimately be swallowed, deployed off of the end of an endoscope, or injected with a syringe. The various exemplary embodiments relate to development of very small mobile devices for in vivo diagnostics and therapy. This development includes 1) design of contact locomotion systems; 2) design and implementation of micro sensors (e.g. fluid flow, pressure, vision, pH); and 3) therapy at the surgical sites. Various exemplary embodiments are also focused on initial contact locomotion candidate systems and implementation with a capsule device for preliminary surgical evaluation in an animal model. Discussed below are tread designs and providing contact locomotion using micro-tread tracks. Initial drawbar force generation data using such tracks are presented, dynamic numerical modeling results are described, and early in vivo results are discussed.

Researchers at Carnegie Mellon University (K. Harada, D. Oetomo, E. Susilo, A. Menciassi, D. Daney, J.-P. Merlet, and P. Dario, "A Reconfigurable Modular Robotic Endoluminal Surgical System: Vision and Preliminary Results," *Robotica*, vol. 28, pp. 171-183, March 2010; R. G. Beutel, and S, N. Gorb, "Ultrastructure of attachment specializations of hexapods (Arthropoda): evolutionary patterns inferred from a revised ordinal phylogeny," *J. Zool. Syst. Evol. Research*, vol. 39, pp. 177-207, December 2001; and R. G. Beutel, and S. N. Gorb, "A Revised Interpretation of the Evolution of Attachment Structures in Hexapoda with Special Emphasis on Mantophasmatodea," *Anthropod Systematics & Phylogeny*, vol. 64, pp. 3-25, October 2006) have developed a method for anchoring a capsule robot in the gastrointestinal tract. In their work, polydimethylsiloxane (PDMS) is used to coat the legs of their anchoring device. Traction is improved further by forming micropillars on the surface of the PDMS. Dry PDMS with a micropillar pattern produced 50-100% more traction than flat surfaces. The PDMS was coated with a thin silicon oil layer, which resulted in as much as a 400% friction improvement. Thus, it was hypothesized that if a thin layer of micro-tread patterned PDMS was applied to the wheels, or treads, of an in vivo mobile robot an increase in friction traction could result.

The preliminary PDMS tread pattern tested was derived from an optimized anchoring design (K. Harada, D. Oetomo, E. Susilo, A. Menciassi, D. Daney, J.-P. Merlet, and P. Dario, "A Reconfigurable Modular Robotic Endoluminal Surgical System: Vision and Preliminary Results," *Robotica*, vol. 28, pp. 171-183, March 2010) including 140 μm pillars with less than 1:2 aspect ratio (i.e. height:width) and 105 μm equidistant spacing. In addition to testing this equally spaced circular pillar design, treads including various other patterns (evenly spaced, straight rows, slanted rows) of circular and square pillars as well as a smooth surface (no pillars) were tested for a total of six tread patterns.

Two of the other five patterns included circular pillars with 140 μm diameter and a 1:2 aspect ratio (height to width). The straight row tread had rows of 245 μm spaced pillars. The rows were spaced 534 μm apart, and oriented perpendicular to the circumference of the wheel. The slanted row tread (helical pattern when wrapped around a wheel) had rows of pillars spaced 245 μm apart. The rows had a perpendicular spacing of 534 μm, and were oriented 30° from a line perpendicular to the circumference of the wheel.

Square pillars were integrated into two additional tread designs. The first square pillar pattern 100 (FIG. 1) had 110 μm pillars 102 with a 1:2 aspect ratio with 102 μm vertical spacing 104 and 135 μm horizontal spacing 106. The second square pillar pattern had square pillars rotated at 45° (rhombus) so that the corners of the square were facing in the direction of travel. The sides of the square were 330 μm, and the edge-to-edge spacing was 127 μm. The sixth tread tested was smooth PDMS, with no pillars.

Figure 2:
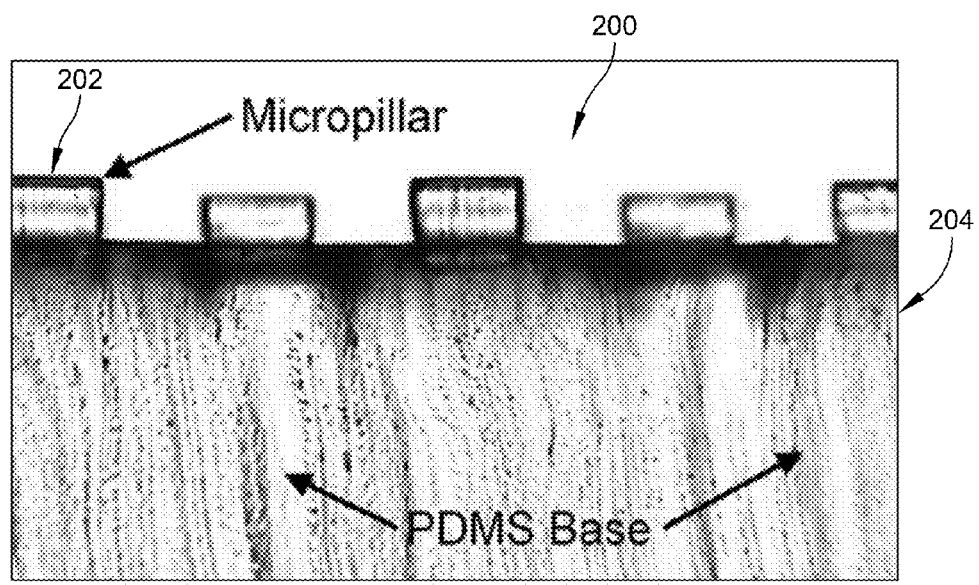
FIG. 2 illustrates a profile view of micro-tread pattern with 100× magnification.

With general reference to FIG. 2, which illustrates a profile view of a micro-tread pattern 200, with 100× magnification, with a series of micropillars 202 on a PDMS base 204. The PDMS treads (the micro-tread pattern 200) were fabricated using a micro-mold constructed from silicon wafers with SU-8 photo-resist. To make the mold, SU-8 2075 photo-resist was poured onto a 7.62 centimeter circular silicon wafer. The wafer was then spun at 500 rotations per minute (RPM) for 10 seconds (s) at an acceleration of 100 RPM/s and then ramped to 3000 RPM for 30 seconds at an acceleration of 255 RPM/s. The wafer was baked for 5 min at 65° C. and 9 minutes at 95° C. The tread pattern was transferred from a chrome mask to the SU-8 photo-resist using a mask aligner and exposure to ultraviolet (UV) light. The mask had a chrome printout of the five tread patterns on it. As the SU-8 mold was exposed to UV light, the SU-8 partially cured. The pattern, which was blocked by the mask, remained uncured. After UV exposure, the wafer was baked again using the same times and temperatures above from the first bake. The wafer was submerged in SU-8 developer for 7 min. The developer washed away the uncured SU-8, producing the mold. Then 2.25 mL of liquid PDMS was poured into the SU-8 micro-mold to create a 0.5 mm thick sample. Once cured, the PDMS was peeled from the mold, and cut into 6 mm wide strips. The strips were glued on 5 mm outer diameter steel hubs that were 8 mm wide using Loctite brand precision super glue (Loctite of Dusseldorf, Germany). These micro-tread patterned hubs were then experimentally tested for drawbar force generation performance.

Micro-Tread Testing Device

Figure 3:
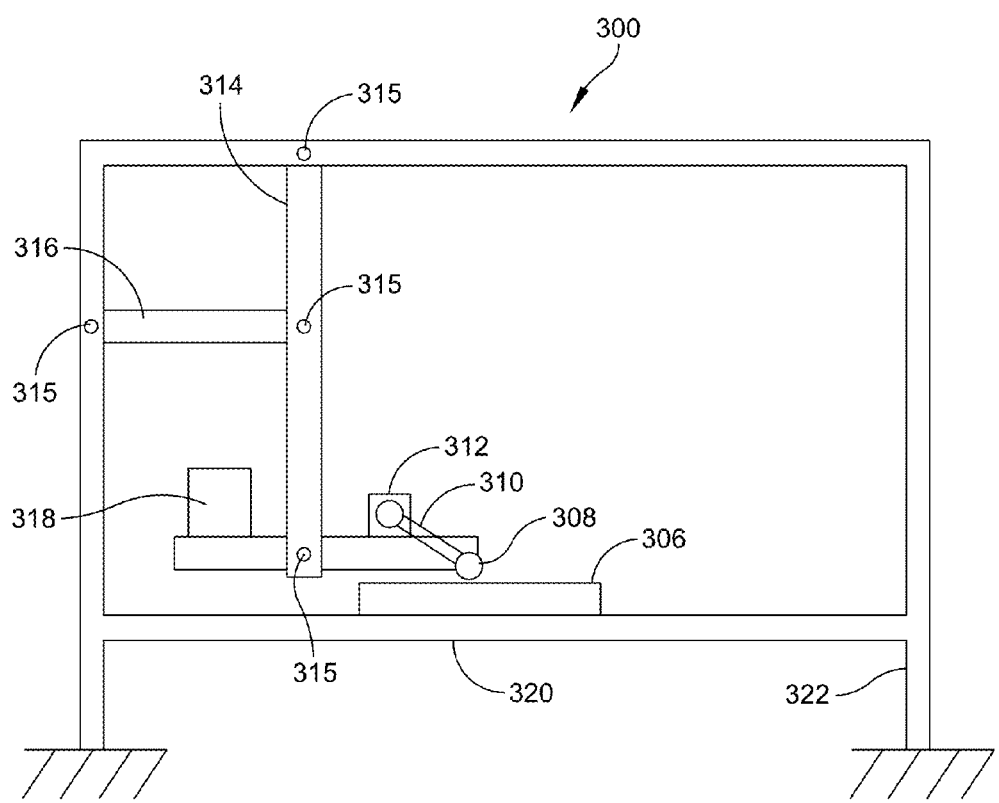
FIG. 3 illustrates a benchtop testing platform schematic.
Figure 4:
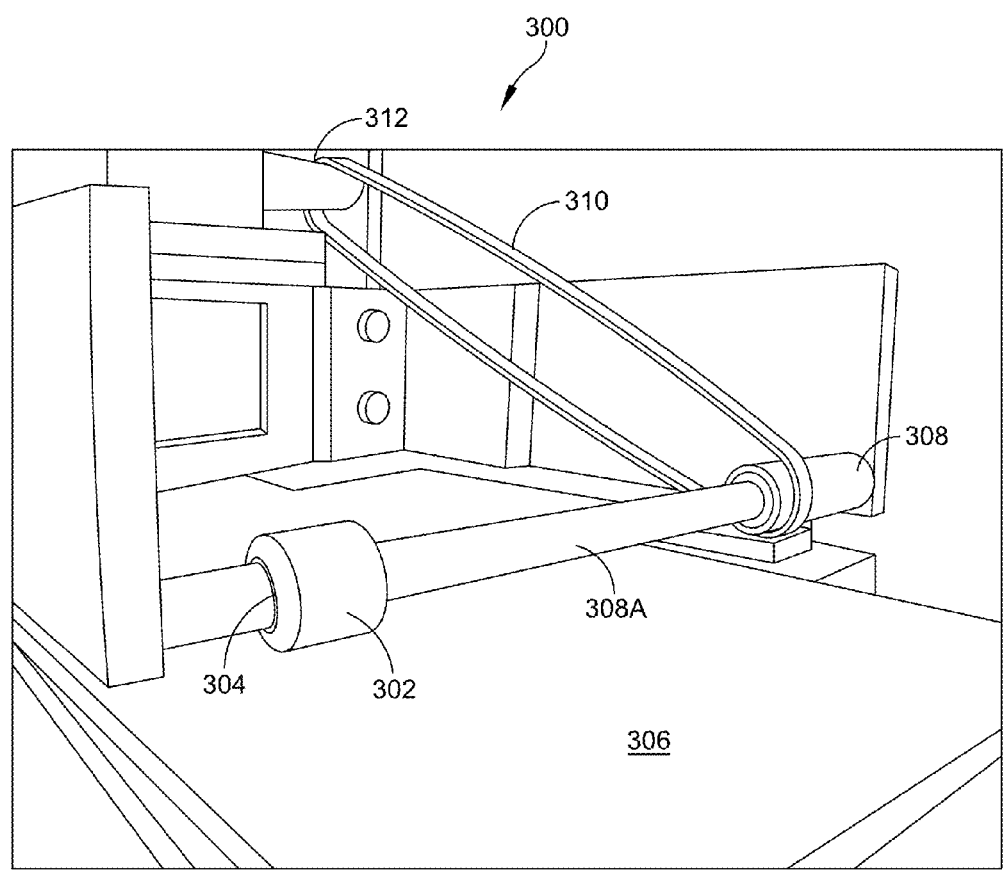
FIG. 4 illustrates a close-up view of the laboratory benchtop testing platform.

To test traction performance of a number of different tread patterns, on a number of different materials, a laboratory benchtop testing apparatus 300 was designed and fabricated (FIGS. 3 and 4). Using this apparatus 300, any number of different treads 302 coated to hub 304 could be evaluated on any number of materials 306 by varying the normal load (i.e. weight of the hub 304), and wheel torque while measuring the resulting generated drawbar force. The testing apparatus featured a rotational axle 308A, 4.5 mm in diameter, to accommodate the removable PDMS coated hubs 304, which made contact with interchangeable surface materials 306. A wheel 308 or timing pulley 308 connected with rotational axle 308A was driven by a belt 310 connected to a direct-current motor 312 (0615 C 4,5S) with a factory installed precision gearhead (06/1 from FAULHABER) that provided a 64:1 gear reduction. The rotational axle 308A and wheel hub 304 were on a pivoting arm 314 to enable changes in applied normal force (i.e. robot or wheel weight). The rotational axis was 12.7 centimeters from a pivot point 315. The pivoting arm 314 was attached to a 20.3 centimeters lever that would apply pressure to a load cell 316 (ESP4-1 KG, Load Cell Central) located 12.7 centimeters above the pivot point 316 as drawbar force was generated. The testing apparatus was controlled by a custom software program (LabVIEW) that moved the wheel axle 308 by setting prescribed power input while simultaneously recording drawbar force measured by load cell 316, and applied current and voltage to the motor 312. Apparatus 300 may also include a counter weight 318 opposite one of the pivot points 315 to balance wheel 308, belt 310, and motor 312. A platform 320 and a frame 322 may be provided to support apparatus 300. In the initial tests presented here, focus was placed on looking at the results from static drawbar tests (i.e., measured maximum drawbar force at the point of sustained slippage). Dynamic tests may be completed in which the material is moved relative to the wheel to induce slip in a controlled manner as various slip ratios are studied.

Figure 5:
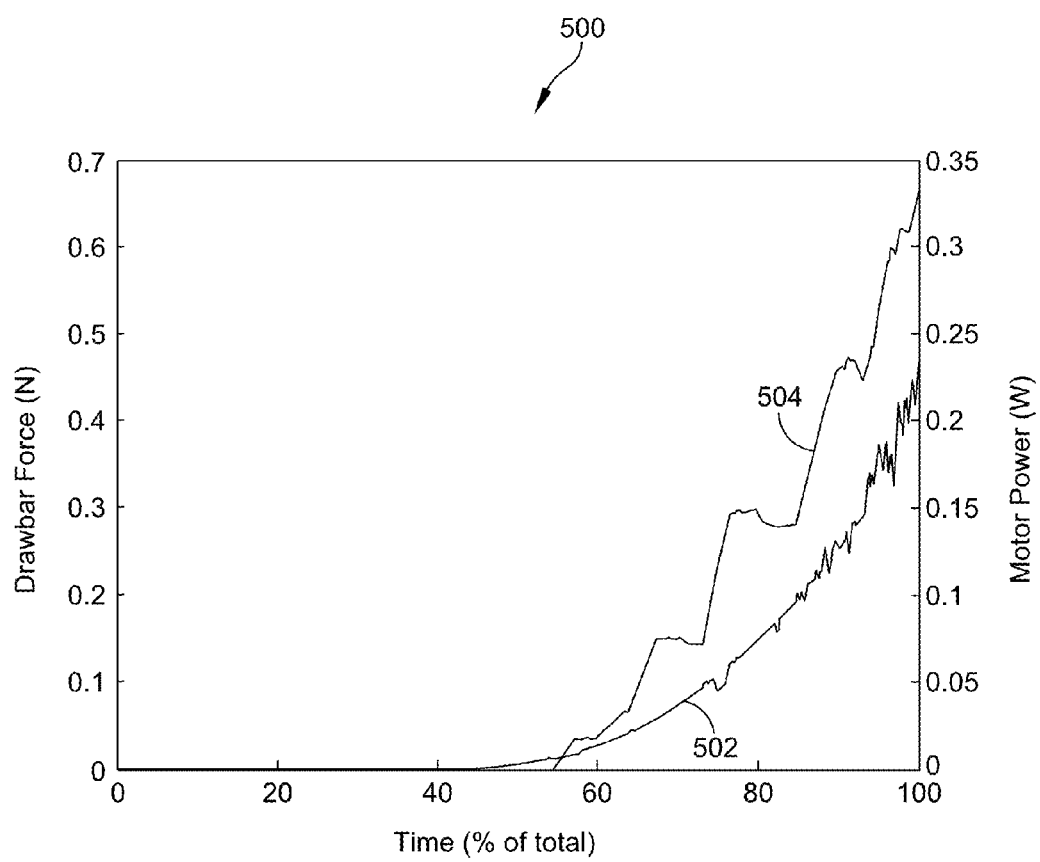
FIG. 5 illustrates typical trial results of patterned PDMS on synthetic tissue.

Test preparation included sliding the wheel hub on to the tapered axle for a frictional fit. The test material (Simulated Tissue, TSS-10, Simulab Corporation of Seattle, Wash.) was placed on the platform, and four normal forces (0.10 N, 0.20 N, 0.30 N, and 0.53 N) were applied sequentially to the axle by adding or removing weights from the horizontal pivoting arm (FIG. 3). During each test, the voltage to the motor driving the axle was ramped at a rate of 0.1 Volt/second. As voltage ramping occurred, the wheel would rotate slightly without slipping, and cause the soft material to deform. Upon further ramping, the wheel would momentarily slip slightly, but then immediately regain traction (FIG. 5). The test was terminated at the point of sustained slippage. Each test would last approximately 15 seconds, from voltage ramp initiation to sustained slippage. Voltage to the motor, current drawn by the motor, and drawbar force produced at the load cell were time-stamped and collected at 1 kHz by the custom software program, and the force produced at the wheel/tissue interface was calculated based on the pivot arm geometry. Each of the six tread patterns was individually tested with each weight five times on the synthetic tissue (Simulated Tissue, TSS-10, Simulab Corporation of Seattle, Wash.) for a total of 120 tests.

Preliminary Micro-Tread Track Results

An example of a typical trial 500 is shown in FIG. 5. The raw power 504 and force data 502 are plotted against a percent of the total time. As the voltage was ramped, the current to the motor increased. The first significant force recorded occurred approximately 70% into the test. As the power continued to increase, the drawbar force generated also increased. The input power signal was uniform, while the measured force signal included some noise that was filtered during data processing.

Figure 6:
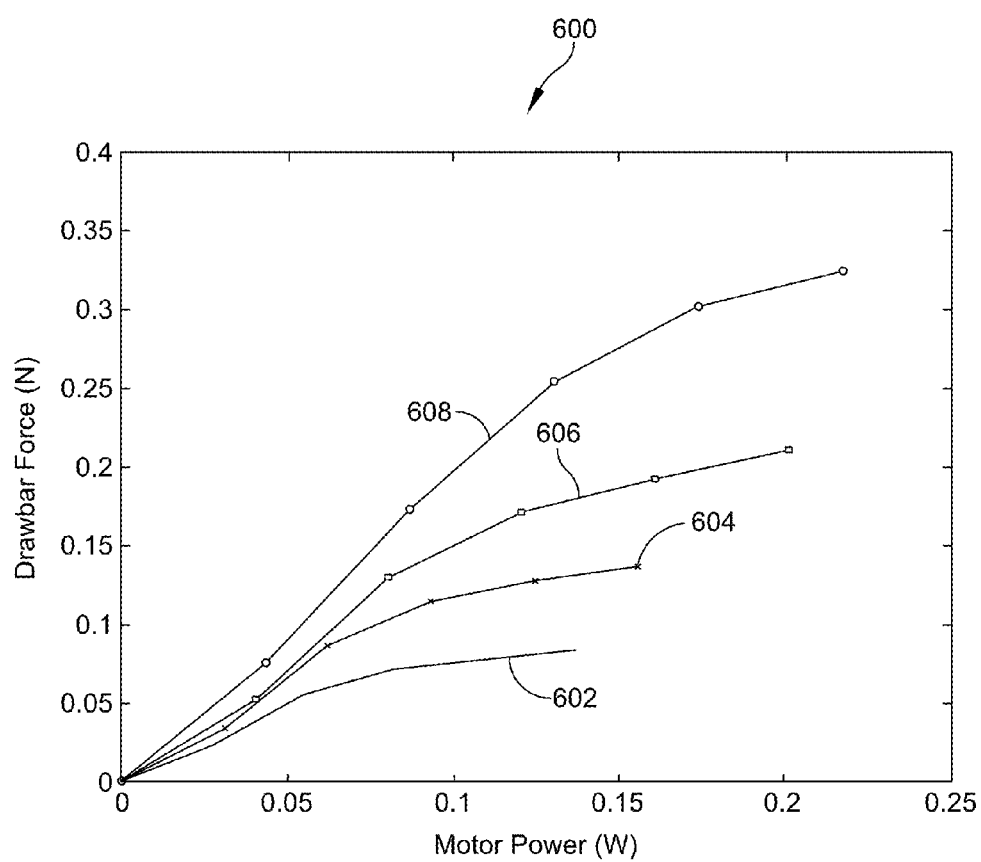
FIG. 6 illustrates test results for varying normal forces (equally spaced circular pillars)
Figure 7:
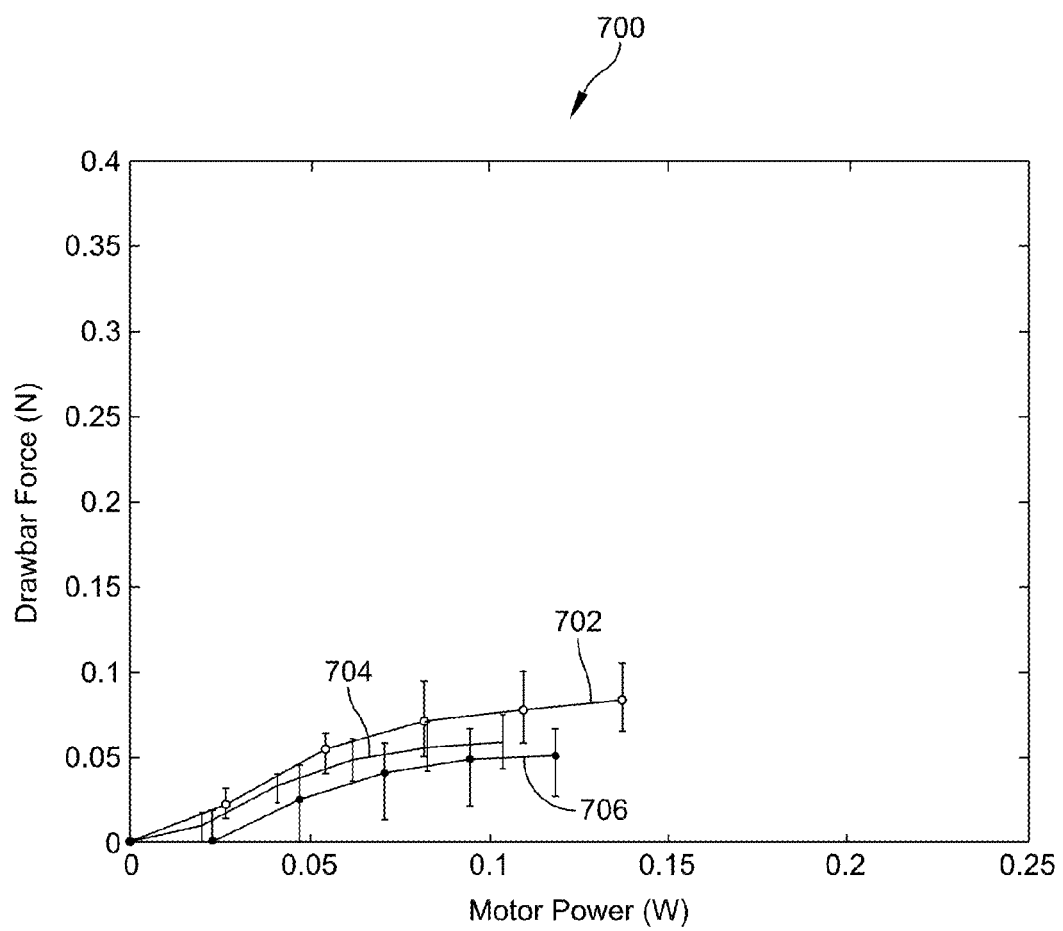
FIG. 7 illustrates drawbar force results for patterns of circular pillars at 0.10 N normal force.
Figure 8:
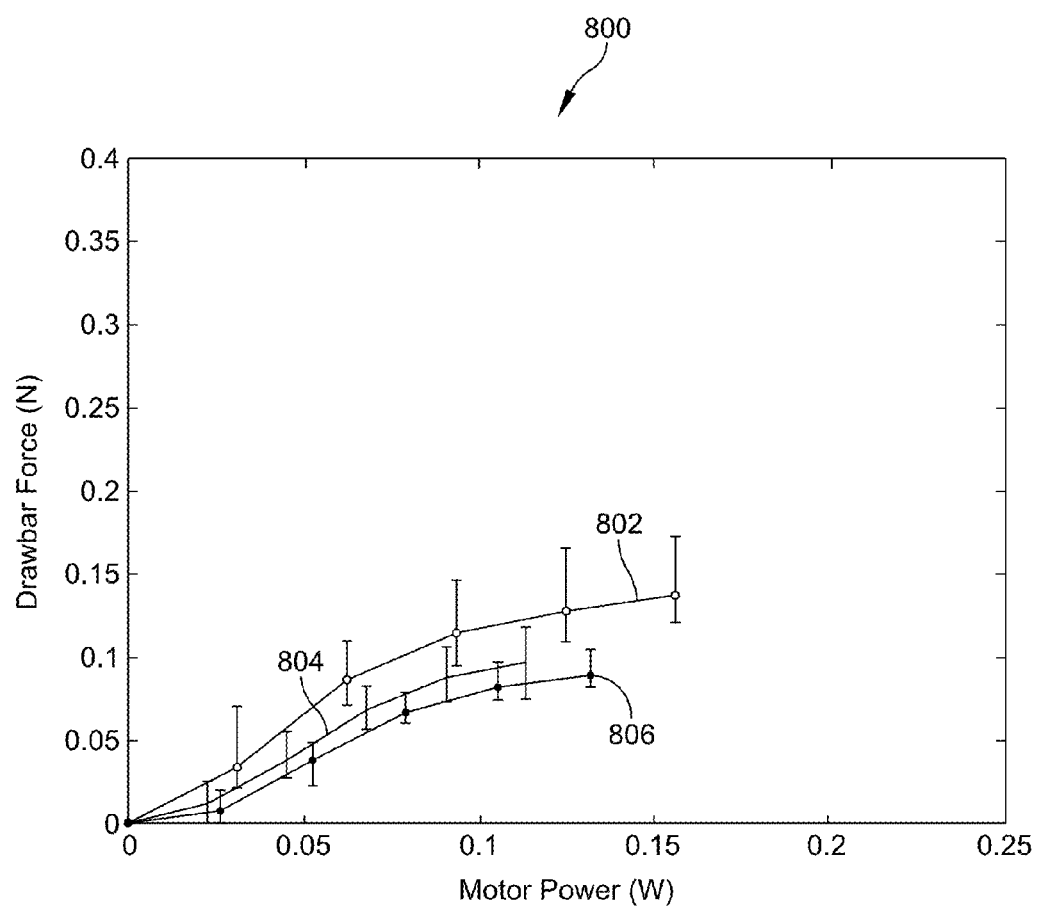
FIG. 8 illustrates drawbar force results for patterns of circular pillars at 0.20 N normal force.
Figure 9:
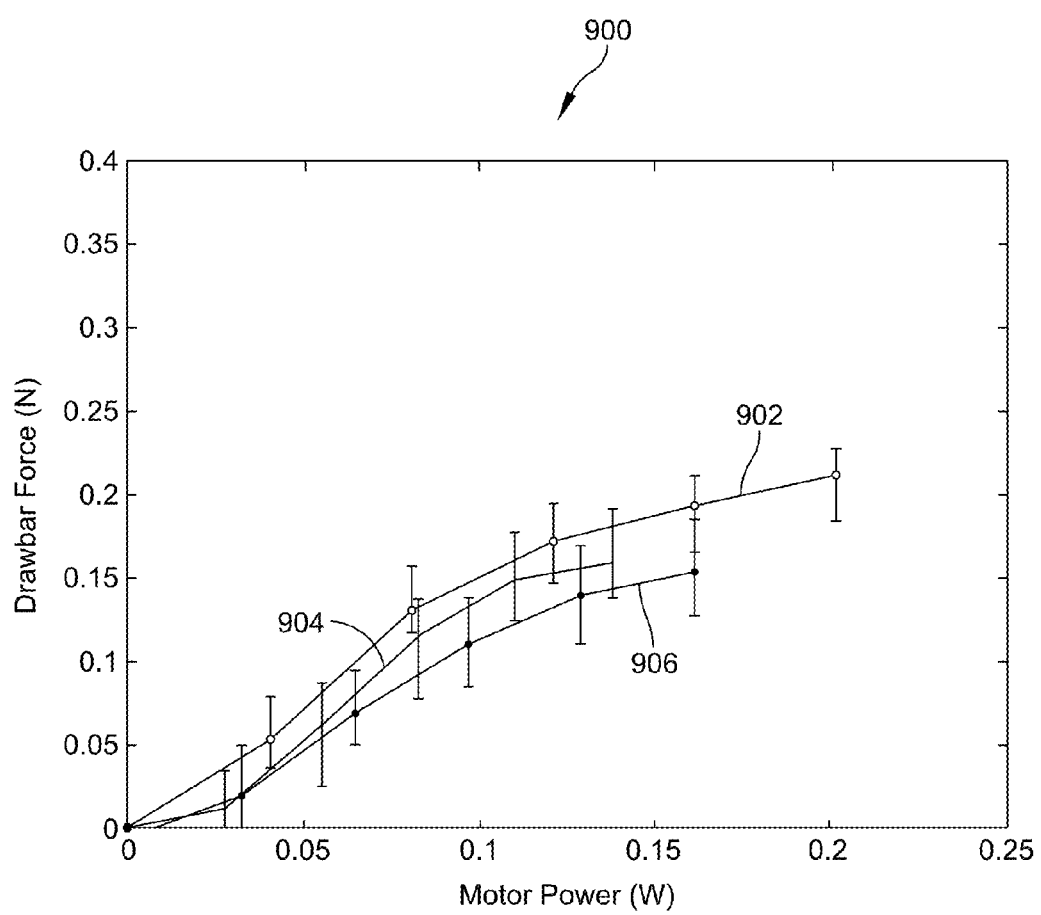
FIG. 9 illustrates drawbar force results for patterns of circular pillars at 0.30 N normal force.
Figure 10:
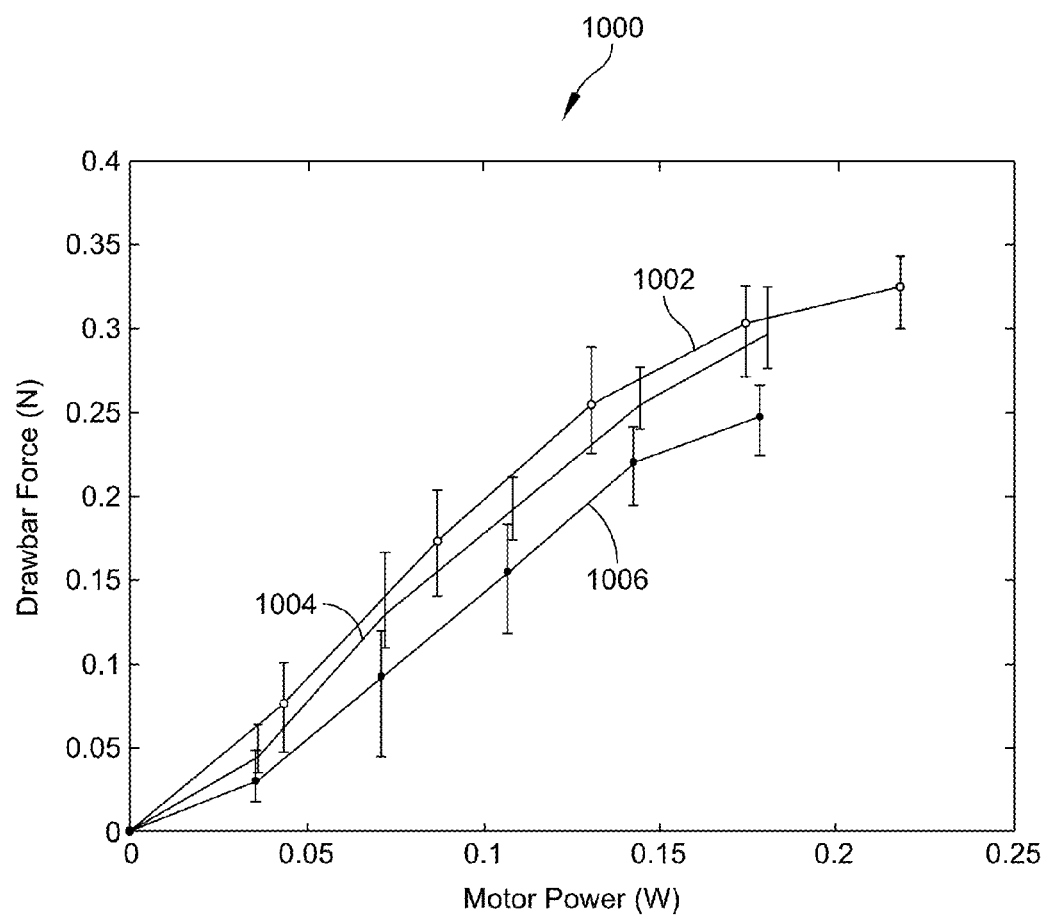
FIG. 10 illustrates drawbar force results for patterns of circular pillars at 0.53 N normal force.
Figure 11:
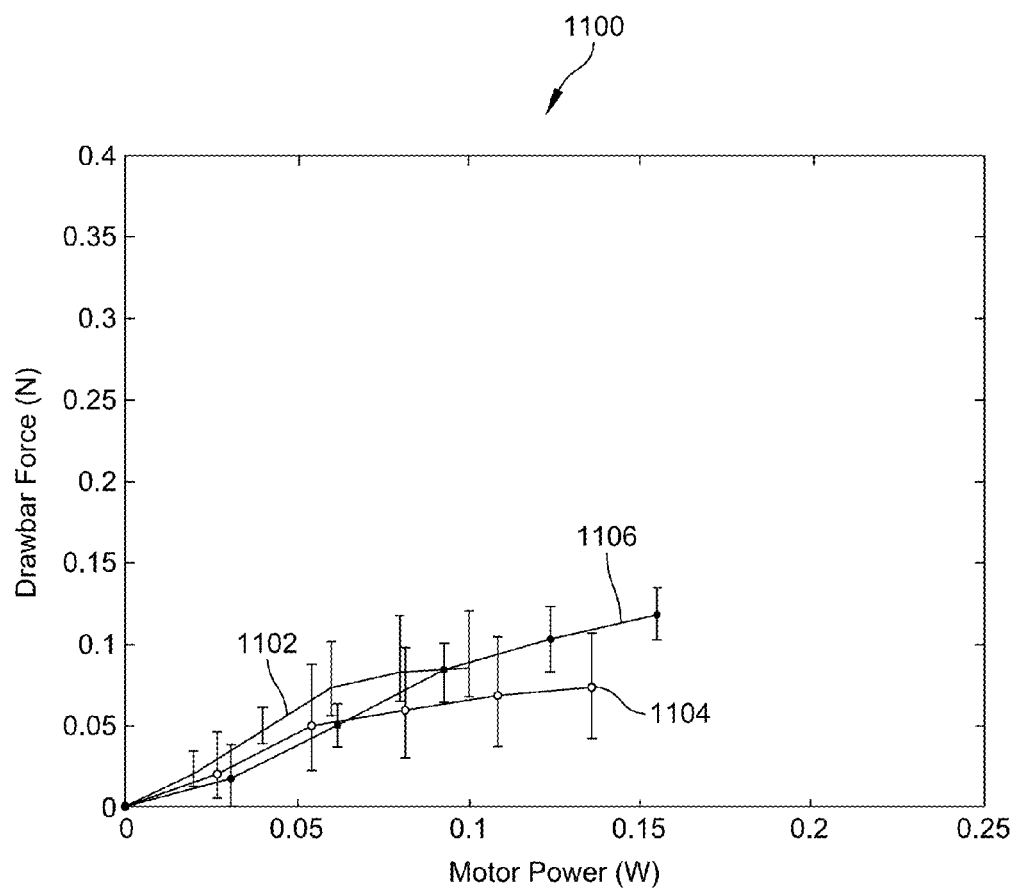
FIG. 11 illustrates drawbar results for alternative shaped tread patterns at 0.10 N normal force.
Figure 12:
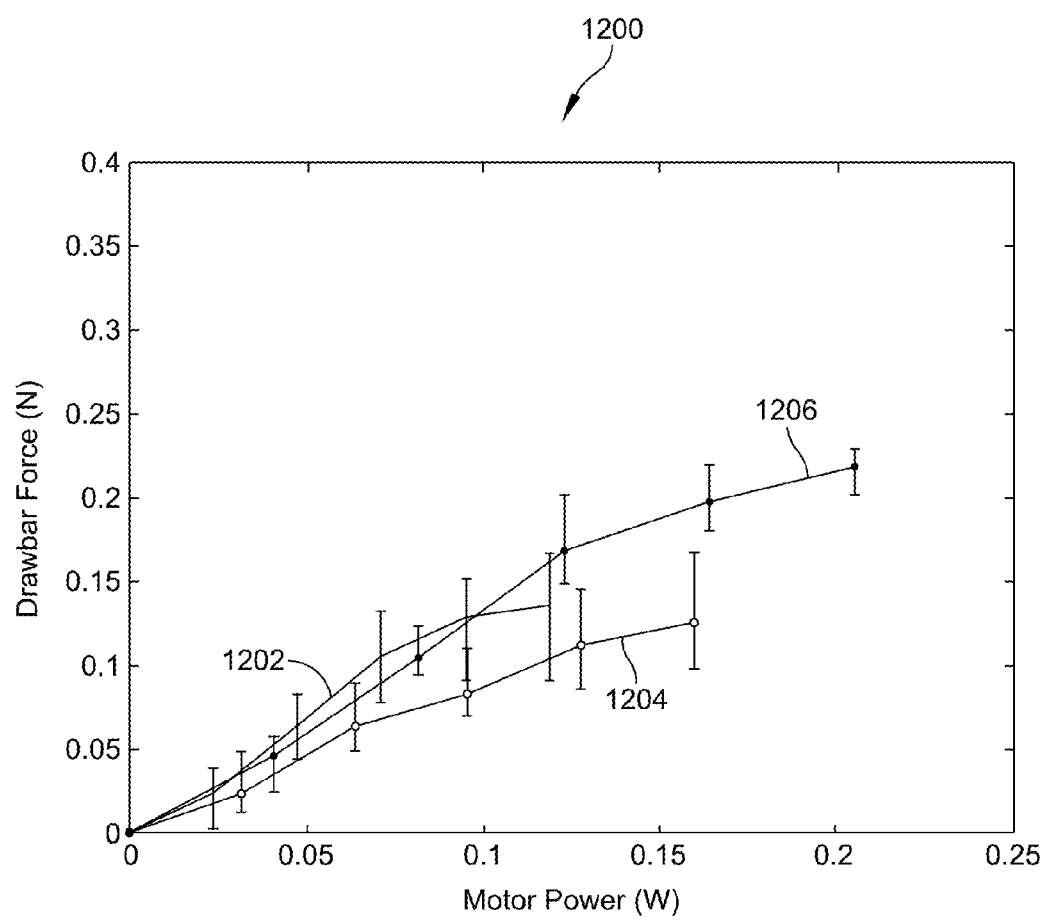
FIG. 12 illustrates drawbar results for alternative shaped tread patterns at 0.20 N normal force.
Figure 13:
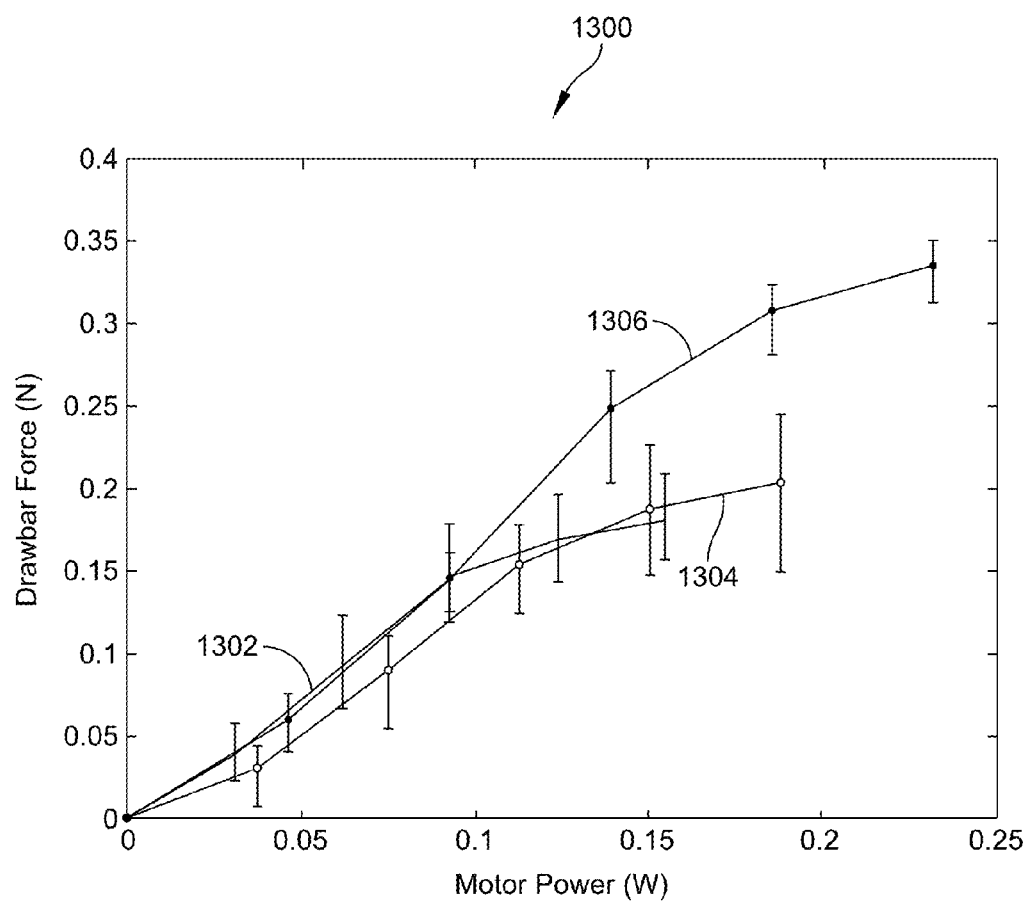
FIG. 13 illustrates drawbar results for alternative shaped tread patterns at 0.30 N normal force.
Figure 14:
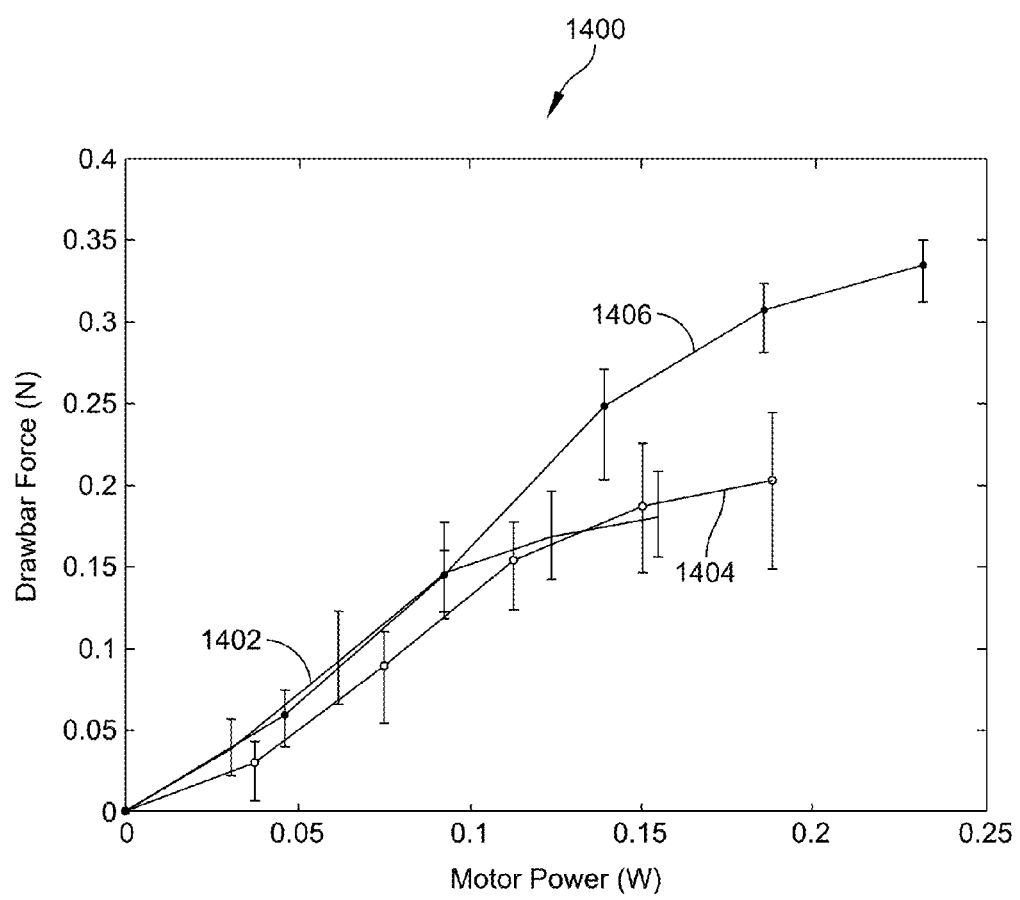
FIG. 14 illustrates drawbar results for alternative shaped tread patterns at 0.53 N normal force.

The critical point within the test was the point of sustained slippage. To find this point in the data set, the motor power was plotted against the percent of total trial time. As the wheel was holding traction, but nearing slipping, the current draw of the motor increased as well as the input power. Once the wheel reached the point of continuous slip, the motor was relieved of the resistance, and the power usage immediately decreased. To locate the point of sustained slippage, a sudden decrease in current was located in the data set. The maximum static drawbar force generated corresponds with this maximum current and power input at the wheel prior to slipping continuously. Representative drawbar test results 600 for varying normal forces including 0.10 N at 602, 0.20 N at 604, 0.30 N at 606, and 0.53 N at 608 are shown in FIG. 6 (equally spaced circular pillars).

Using the input voltage and current, electrical motor input power was calculated. The power and drawbar force data for the five trials for each tread pattern were filtered, averaged, and divided into two categories: treads with circular pillars 700, 800, 900, 1000 (FIGS. 7-10), and treads with alternative pillar shapes 1100, 1200, 1300, 1400 (FIGS. 11-14). The three types of circular treads included: (1) equally spaced (equidistant) 702, 802, 902, 1002, (2) straight rows 704, 804, 904, 1004, and (3) helical rows 706, 806, 906, 1006 (at 30°). The three types of other treads tested were: (4) square treads 1102, 1202, 1302, 1402, (5) rhombi (or diamond shaped treads that were square treads rotated 45°) 1104, 1204, 1304, 1404, and (6) flat no pattern treads 1106, 1206, 1306, 1406. The recorded mean drawbar forces for each tread pattern were plotted against input power on two different graphs, one for each category with error bars showing maximum and minimum drawbar force values. Results are condensed in Table 1, which is shown in FIG. 53.

For all normal forces, the results of the circular pillar comparison revealed two trends. The equally spaced pattern 702-1002 produced a larger maximum drawbar force at the slipping point than both the helical pattern 706-1006 and straight row patterns 704-1004. Similarly, the straight row pattern 704-1004 produced a larger maximum drawbar force at the slipping point than the helical row pattern 706-1006. The maximum drawbar force to normal force ratio was compared between the three circular pillar patterns, and for each normal force, the equally spaced pattern 702-1002 had a higher ratio than both the helical pattern 706-1006 and straight row pattern 704-1004. Similarly, the straight row pattern 704-1004 had a higher ratio than the helical row pattern 706-1006.

The square treads 1102-1402 and rhombi patterned treads 1104-1404 performed similarly to the circular helical treads 706-1106 and circular straight treads 704-1004. The smooth tread 1106-1406 with no patterned pillars performed similar to the other treads as power was increased but it generated the largest drawbar force before slipping. This possibly suggests that an evenly distributed, or flatter tread, allows for the largest static force as the normal force is more evenly distributed and not discretized with pillars.

All treads roughly followed the same force vs. power curve (FIGS. 7-14), but deviated towards the top of the curve. The smooth tread 1106-1406 was able to produce a larger drawbar force at a higher power, where as the square pillar treads 1102-1402 and rhombus pillar treads 1104-1404 started slipping at a lower power while producing less force. In addition to producing the largest drawbar force at the slipping point, the smooth tread 1106-1406 displayed the largest maximum drawbar force to normal force ratio, indicating that it is the most efficient tread design. The success of the smooth tread could be attributed to the applied normal forces. The patterned treads may not have experienced enough normal force to make the pillars useful. With too little normal force, the patterned treads might have been bouncing on top of the tissue, instead of gaining traction. With less normal force, a larger distributed contact surface area might have been the leading factor for success. With a large contact surface area, and low normal force, the smooth tread 1106-1406 might have had an advantage in this static testing. Additionally, the success of the smooth tread 1106-1406 could be attributed to the material surface environment. In these tests, the synthetic tissue was dry. On a wet synthetic tissue surface, the patterned and smooth PDMS treads might perform differently.

The results presented here for the equally spaced circular pillar tread results, were compared with other results (Valdastri, P., Webster, R. J., Quaglia, C., Quirini, M., Menciassi, A., and Dario, P., 2009. "A New Mechanism for Mesoscale Legged Locomotion in Compliant Tubular Environments". *IEEE Transactions on Robotics,* 25(5), October, pp. 1047-1057; Ciuti, G., Valdastri, P., Menciassi, A., and Dario, P., 2010. "Robotic magnetic steering and locomotion of capsule endoscope for diagnostic and surgical endoluminal procedures". *Robotica,* 28(2), March, pp. 199-207; and Simi, M., Valdastri, P., Quaglia, C., Menciassi, A., and Dario, P., 2010. "Design, Fabrication, and Testing of a Capsule With Hybrid Locomotion for Gastrointestinal Tract Exploration". *IEEE/ASME Transactions on Mechatronics,* 15(2), April, pp. 170-180.) [24-26]. In those studies, a micro-patterned PDMS anchor was drug over tissue. The static force measured was approximately 0.08 N with an applied normal force of 0.50 N. Thus, the results presented here show similar drawbar forces.

The maximum drawbar force to normal force ratio was compared between all tread patterns. For all tread patterns, the maximum ratio occurred at a normal force of 0.10 N (Table 1, which is shown in FIG. 53), indicating that all of the treads are more efficient at the lower normal force.

Numerical Modeling

Figure 15:
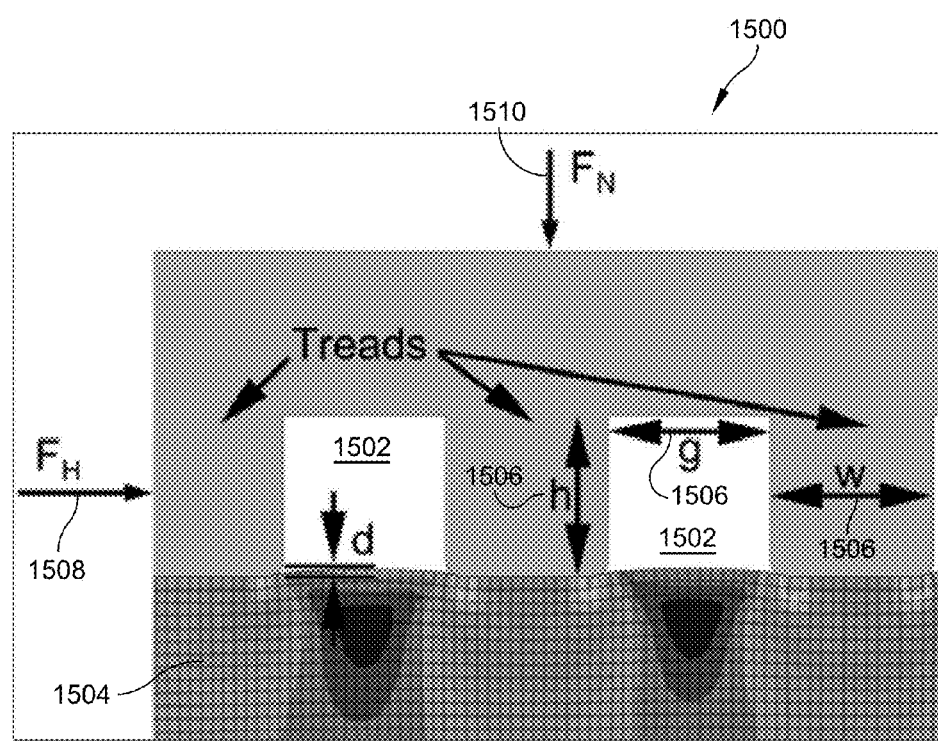
FIG. 15 illustrates 2D-planar model of PDMS micro-treads on tissue (using properties of viscoelastic liver)
Figure 16:
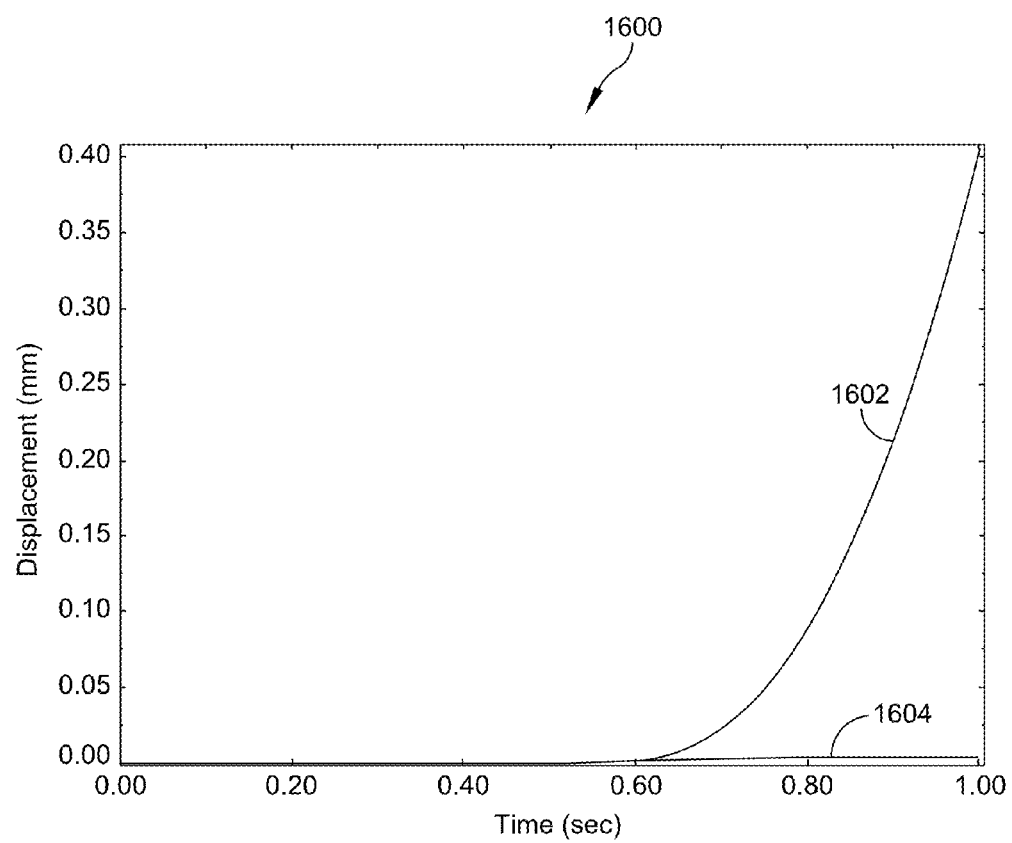
FIG. 16 illustrates results of the numerical simulation using Abaqus Finite Element Analysis (FEA) software in which the patterned tread (bottom) performs superior to the smooth tread (top)

Prior to animal surgical testing, both the treaded PDMS material and smooth PDMS material was numerically modeled using Abaqus Finite Element Analysis (FEA) software. An image 1500 of the model is shown in FIG. 15. The micro-treads were modeled as 2D-planar pillars 1502 on top of liver 1504 (FIG. 15). As the PDMS material is 40 to 150 times stiffer (depending on the modulus of PDMS, which ranges from 360 kPa to 870 kPa) than tissue, the PDMS treads were modeled as solid, rigid bodies, while the tissue was modeled using the viscoelastic properties of liver. (Rentschler, M., Reid, J., "The Development of a Material Model and Wheel-Tissue Interaction for Simulating Wheeled Surgical Robot Mobility," *Computer Methods in Biomechanics and Biomedical Engineering.* 12(2): 239-248, 2009.) The pillars 1502 in the numerical model were equally spaced 1506 (h=w=g=100 µm), with an edge radius of 10 µm; and constant normal force 1508 ($F_N$=0.24 N) and horizontal force 1510 ($F_H$=0.07 N) were applied to the treads (FIG. 15) during the simulation. The output of the simulation was horizontal tread displacement as a function of time. An optimal tread would be one that has minimal horizontal movement throughout the simulation (good traction), while a poor performing tread would have significant horizontal motion throughout the simulation (poor traction). The simulation was repeated with identical normal and horizontal forces for smooth (no pillars) PDMS. The duration of each simulation was one second. The results 1600 of the two simulations are shown in FIG. 16.

The smooth wheel 1602 had significantly more horizontal motion during the simulation, thus indicating an inferior performance when compared to the patterned model 1604 in this dynamic simulation. The patterned tread moved minimally, suggesting that the patterned wheel would perform superior to the smooth wheel on liver.

Figure 17:
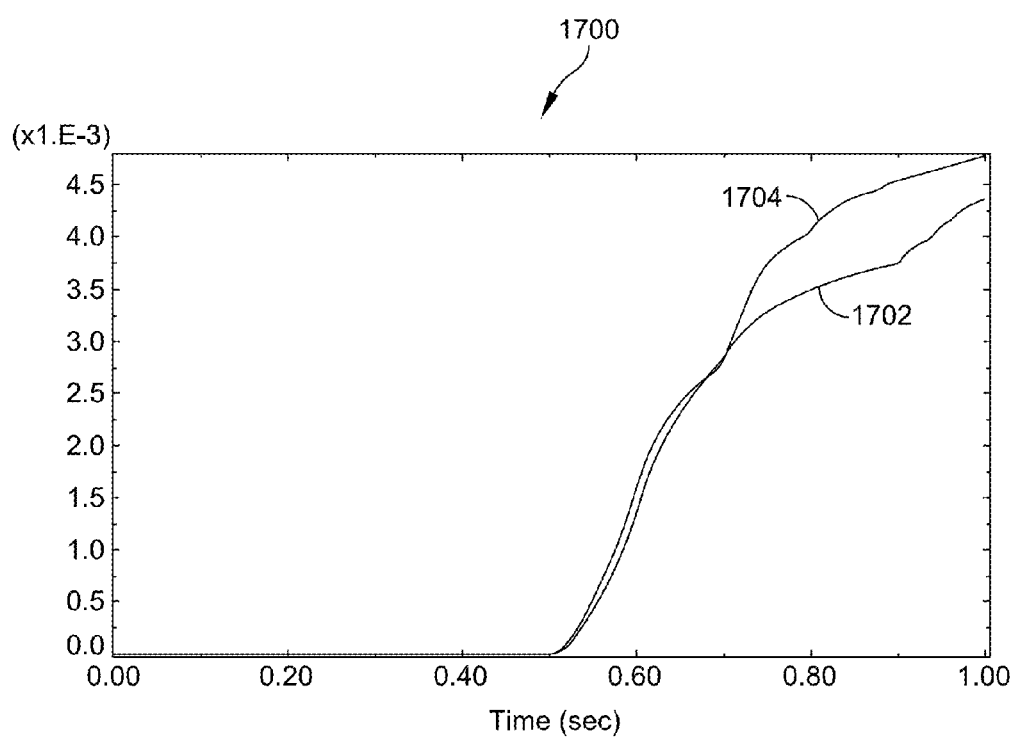
FIG. 17 illustrates results of the pillar density simulation in which the low-density pillars (top) had a larger horizontal displacement during the simulation than the high-density pillars (bottom)

In addition to comparing the performance of smooth and patterned PDMS treads on viscoelastic liver, a simulation was performed to investigate the effect of pillar density on tread performance. A second, higher density model 1702, with a tread size reduced by 50% (h=w=g=50 μm), was compared with the 100 μm spacing model 1704. Both simulations included the same pillar surface area, lasted for one second, and had identical constant applied normal and horizontal forces. The results 1700 of the density simulations are shown in FIG. 17.

The high-density pillars had less horizontal movement during the simulation, thus indicating a superior performance when compared to the low-density pillars. The results of this test would suggest that the higher the pillar density for a given tread, the more traction that tread will provide on liver, though these results have not yet been confirmed experimentally.

In Vivo Results

Figure 18:
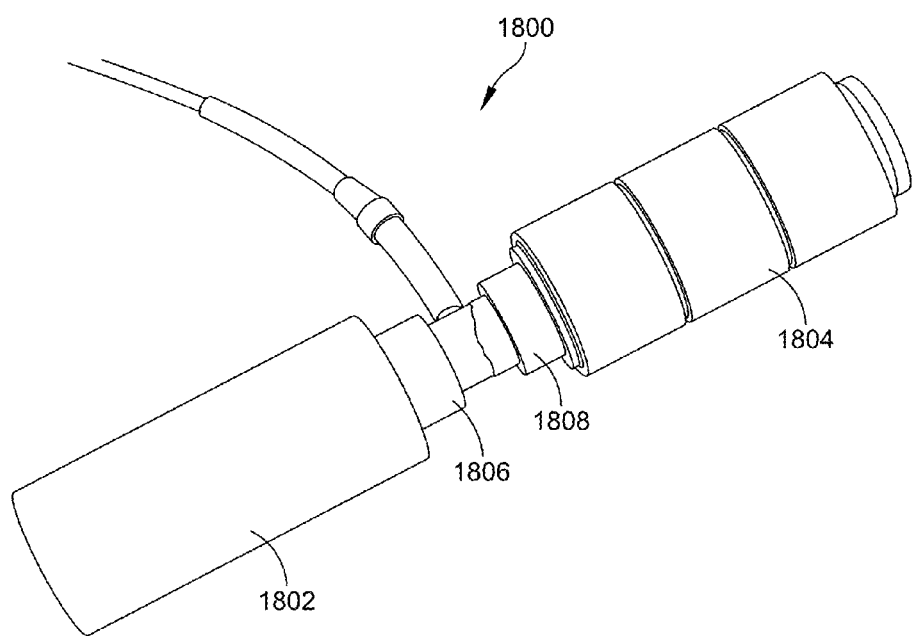
FIG. 18 illustrates a robot used for in vivo comparison of micro-patterned vs. smooth wheels.

The results of the dynamic numerical model on viscoelastic liver suggested that the wheels would perform differently in a dynamic, in vivo, environment than they had during the static benchtop tests on dry synthetic tissue. To better understand the tread performance, a simple robot 1800 was fabricated to test the theory in vivo. The robot 1800, shown in FIG. 18, was constructed using aluminum. The robot had two wheels 1802, 1804, each with an identical surface area and evenly distributed weight. Each wheel was powered by an identical FAULHABER motor (FAULHABER, Croglio, Switzerland) with a 64:1 FAULHABER gear head. Each motor was capable of clockwise and counterclockwise motion, creating a tank-like steering environment. The robot 1800 was tethered to provide power and control communications. The symmetrical robot 1800 was 19 mm in diameter, 110 mm long, and weighed 50 g. The center of mass of the robot 1800 was in its middle, so the normal force of each wheel 1802, 1804 was identical. One of the wheels 1802 was coated with smooth (no pattern) PDMS, while the other wheel 1804 was coated with patterned (equally spaced circular pillars) PDMS.

Figure 19:
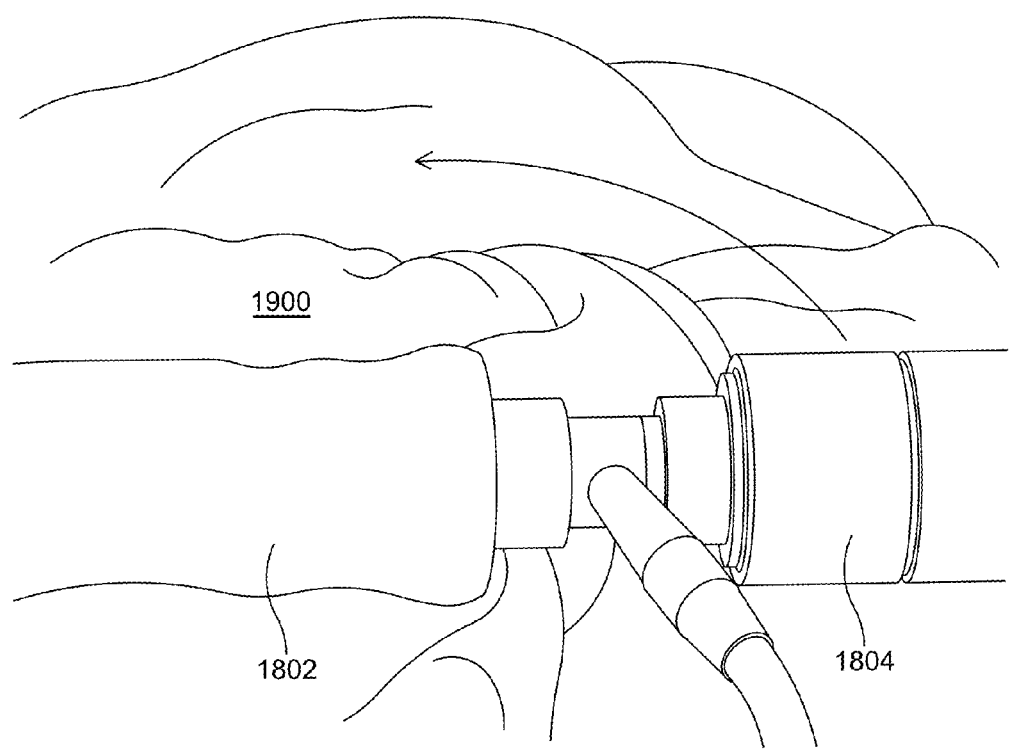
FIG. 19 illustrates in vivo robot on small bowel (view from laparoscope)
Figure 20:
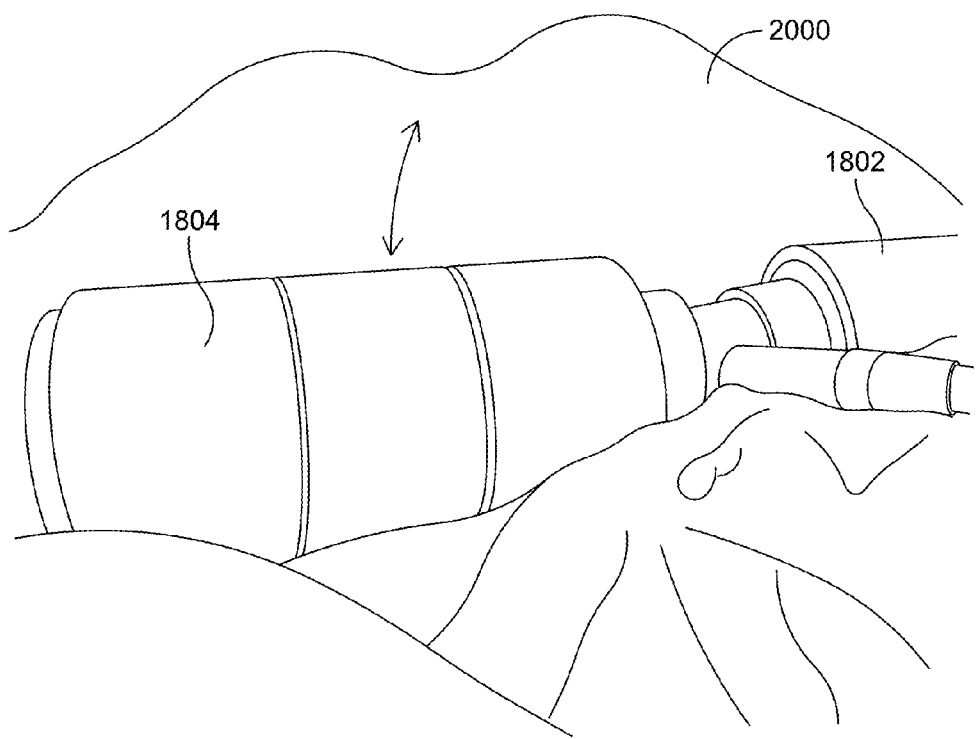
FIG. 20 illustrates in vivo robot on liver (view from laparoscope)

The robot 1800 was placed in an insufflated abdomen of a live anesthetized porcine (pig) model. The robot wheels 1802, 1804 were activated, and it was observed that the patterned wheel 1804 performed superior to the smooth wheel 1806. The robot 1800 was placed on a variety of different tissues including small bowel 1900 (FIG. 19), stomach (not shown), and liver 2000 (FIG. 20). The wheels performed similarly on all tissues. The patterned wheel 1804 had sufficient traction to move the robot on all tissues, while the smooth wheel 1802 generally spun freely with no sign of traction. These mobility tests were administered for approximately 15 min on all tissues in the abdominal cavity.

In various embodiments, treads with micro-patterns of varying geometries and spacing were tested using a static open-loop testing apparatus. The treads were tested to compare their drawbar force on dry synthetic tissue as a starting point. It was found that a smooth PDMS tread outperformed all other tread patterns. There were no significant differences between the performance of square and circular pillars. Of the patterns featuring circular pillars, an equally spaced configuration performed superior to the other configurations.

Dynamic numerical modeling was also performed to further investigate the tissue-tread interaction. Treads were modeled as 2D-planar solid, rigid bodies on viscoelastic liver. The results of the simulations suggested that a patterned tread would perform superior to a smooth wheel in viva An in vivo comparison of a smooth PDMS covered wheel and a patterned (equally spaced circular pillars) PDMS covered wheel was performed, and the patterned wheel outperformed the smooth wheel.

More benchtop testing may be undertaken with a closed-loop dynamic system. The effects of slip ratio, additional materials (including excised tissues), and pillar density may be investigated experimentally. Numerical modeling may be used to predict the performance of new treads, coupled with benchtop tests, and candidate tread designs will be evaluated in vivo.

The static benchtop tests suggest that all of the treads perform most efficiently at the lowest normal force tested (0.10 N). In future tests, the range of varied normal forces will be increased to include even lower normal forces (lighter mobile robots) to determine if the efficiency trend continues for these lower normal forces.

The use of endoscopic devices to diagnose and treat a range of gastrointestinal (GI) conditions has recently grown, however minimally invasive surgical and exploratory procedures within the lumen of the GI tract are currently limited to endoscopic techniques. When utilizing an endoscopic device, a surgeon has two options of entering the GI tract: (1) through the oral cavity, down the esophagus, through the stomach, and into the small intestine via the duodenum, or (2) through the anus, through the rectum, and into the colon and large intestines. A long "push" endoscope inserted through the oral cavity can reach the medial small intestine whereas an endoscope inserted through the anus can only reach the distal part of the small bowel. This leaves a section of the small intestine that is inaccessible by traditional endoscopes. Some diseases, such as celiac sprue, can only be diagnosed through biopsy, whereas others can be diagnosed visually, such as cancerous polyps, but may only be observed on a small fraction of the available tissue within the GI tract (P. H. Green, and C. Cellier, "Medical progress: Celiac disease," *N Engl J. Med., vol.* 357, pp. 1731-1743, October 2007.) Additionally, 2.3% of colonoscopies with polypectomies result in complications (J. A. Dominitz, G. M. Eisen, T. H. Baron, et al., "Complications of colonoscopy," *Gastrointestinal Endoscopy*, vol. 57, pp. 441-445, April 2003.)

In order to improve diagnostic statistics of GI diseases and increase the number of successful outcomes of GI surgical procedures, a new technique is being developed. This technique moves away from long flexible scopes, and towards small, pill-sized capsules termed capsule endoscopes. The most advanced capsule endoscope (CE) on the market today is the PillCam (Made by Given Imaging, headquartered in Yoqneam, Israel), a device that contains an imaging system, which is swallowed by the patient. Although the PillCam can visualize the GI tract, it is a passive device, and therefore cannot be maneuvered through the GI tract. The PillCam has a maximum imaging rate of 18 images/s (half that of standard video) and cannot be used in patients with existing cardiac pacemakers or other implanted electromedical devices (*Given Imaging Website* (2011, April 6), Given Imaging Ltd., Duluth, Ga. Available: www.givenimaging.com.) Furthermore, for patients with Crohn's disease (an inflammatory bowel disease diagnosable by PillCam), 5% of PillCam procedures result in capsule retention. (D. Cave, P. Legnani, R. de Franchis, and B. S. Lewis, "ICCE consensus for capsule retention," *Endoscopy*, vol. 37, pp. 1065-1067, October 2005; and L. Zhuan, G. Rui, X. Can, L. Zhao-Shen, "Indications and detection, completion, and retention rates of small-bowel capsule endoscopy: a systematic review," *Gastrointestinal*

Endoscopy, vol. 71, pp. 280-286, February 2010.) This results in required surgical removal of the PillCam. One way to improve this statistic would be to introduce the ability to actively maneuver the CE while inside the GI tract.

The focus of this disclosure is a locomotion system for an active robotic capsule endoscope (RCE) that can be placed completely inside the patient and that can be maneuvered in both insufflated and collapsed lumens and cavities. This in vivo device, equipped with a real-time imaging system, sensors, and tools could be precisely controlled to move anywhere within the GI tract. Once at the surgical site of interest, the RCE would provide therapy in the form of biopsy, tissue dissection, drug delivery, or the "tagging" of tissue for future surgical removal (e.g., colectomy for a cancerous section of colon). This RCE could ultimately be swallowed, deployed off of the end of an endoscope, or possibly injected with a large syringe. Potentially, the RCE will be used for natural orifice translumenal endoscopic surgery (NOTES), where the RCE enters through a natural orifice, travels through the GI tract, exits the GI tract, performs a surgical procedure elsewhere in the body (e.g., a cholecystectomy), returns to the GI tract, and exits the body naturally. The long-term objective of this work is to develop very small mobile devices for in vivo diagnostics and therapy. The short-term goal of this work, and the work presented in this paper, is to design and experimentally evaluate micro-patterned treads as a contact locomotion candidate system. Also disclosed is an in depth review of the design of the custom benchtop testing platform used to evaluate the micro-patterned tread traction force.

Micro-Patterns for Friction Enhancement

Micro-patterning has been used in many applications, ranging from fluids to friction enhancement. For various embodiments, friction enhancement properties of micro-patterning is of interest. Micro-patterning for friction enhancement stems from a biological phenomenon found on the feet of various animals. Terrestrial animals have evolved to develop one of two different micro-patterns on the pads of their feet to enhance friction for locomotion on a variety of different substrates: hairy pads and smooth pads. (R. G. Beutel, and S. N. Gorb, "Ultrastructure of attachment specializations of hexapods (Arthropoda): evolutionary patterns inferred from a revised ordinal phylogeny," *J. Zool. Syst. Evol. Research*, vol. 39, pp. 177-207, December 2001; and R. G. Beutel, and S, N. Gorb, "A Revised Interpretation of the Evolution of Attachment Structures in Hexapoda with Special Emphasis on Mantophasmatodea," *Anthropod Systematics & Phylogeny*, vol. 64, pp. 3-25, October 2006.) Both types of pads are able to match the surface structure of their respective substrates, maximizing the contact surface area, and thus increasing the frictional and adhesive properties of the feet. (S. Gorb, "Biological microtribology: anisotropy in frictional forces of orthopteran attachment pads reflects the ultrastructure of a highly deformable material," *Proc. Roy. Soc. London B*, vol. 267, pp. 1239-1244, June 2000; S, N. Gorb, *Attachment Devices of Insect Cuticle*, New York, N.Y.: Springer, 2001; and B. N. J. Persson, S. Gorb, "The effect of surface roughness on the adhesion of elastic plates with application to biological systems," *J. Chem. Phys.*, vol. 119, pp. 11437-11444, December 2003.) Micro-patterned (circular pillars) polydimethylsiloxane (PDMS) has been used as a method for anchoring a capsule robot. (M. Karagozler, E. Cheung, J. Kwon, and M. Sitti, "Miniature Endoscopic Capsule Robot Using Biomimetic Micro-Patterned Adhesives," *Biomedical Robotics and Biomechatronics*, pp. 105-111, February 2006; E. Cheun, E. Karagozler, S. Park, B. Kim, and M. Sitti, "A New Endoscopic Microcapsule Robot Using Beetle Inspired Microfibrillar Adhesives," in *Proc. of the 2005 IEEE/ASME International Conf. on Advanced Intelligent Mechatronics*, Monterey, Calif., 2005, pp. 551-557; and P. Glass, E. Cheung, and M. Sitti, "A Legged Anchoring Mechanism for Capsule Endoscopes Using Micro-patterned Adhesives," *IEEE Trans. Biomed. Eng.*, vol. 55, pp. 2759-2767, December 2008.) The legs of the anchoring device were coated with the micro-patterned PDMS and friction between PDMS and porcine intestine was measured. Results of the study showed that dry PDMS with a micro-pattern produced 50-100% more traction than flat surfaces. Additionally, PDMS coated with a thin layer of silicone oil resulted in as much as a 400% friction improvement. Most recently, Buselli et al. have placed micro-patterned pads on the ends of the legs of the device in the following: C. Stefanini, A. Menciassi, and P. Dario, "Modeling and Experiments on a Legged Microrobot Locomoting in a Tubular, Compliant and Slippery Environment," *Int. J. Robot. Res.*, vol. 25, pp. 551-560, May 2006; A. Menciassi, C. Stefanini, S. Gorini, G. Pernorio, B. Kim, J. O. Park, and P. Dario, "Locomotion of a Legged Capsule in the Gastrointestinal Tract: Theoretical Study and Preliminary Technologoical Results," in *IEEE International Conf. on Engineering in Medicine and Biology*, San Francisco, Calif., 2004, pp. 2767-2770; and P. Valdastri, R. J. Webster, C. Quaglia, M. Quirini, A. Menciassi, and P. Dario, "A New Mechanism for Mesoscale Legged Locomotion in Compliant Tubular Environments," *IEEE Transactions on Robotics*, vol. 25, pp. 1047-1057, October 2009 in order to enhance the friction at the leg-tissue interface. (E. Buselli, V. Pensabene, P. Castrataro, P. Valdastri, A. Menciassi, and P. Dario, "Evaluation of friction enhancement through soft polymer micro-patterns in active capsule endoscopy," *Meas. Sci. Technol., vol. 21*, pp. 1-7, September 2010.)

Micro-patterned treads may be implemented into an RCE for use as a mobility system. The specifics of why the micro-pattern enhances friction from a contact mechanical perspective are unknown, and the purpose of this work is to experimentally investigate this problem.

Design of Micro-Patterned Treads

A series of micro-patterned treads were designed for traction force testing. A base case was designed from a previously optimized design, along with additional tread patterns that were designed to investigate edge effects within the pattern. Due to its biocompatibility, accessibility, ease of use, and hydrophobicity, PDMS was chosen as a polymer for the micro-pattern fabrication. All PDMS samples with micro-patterns were tested against smooth (no pattern) PDMS.

Base Case

Figure 21:
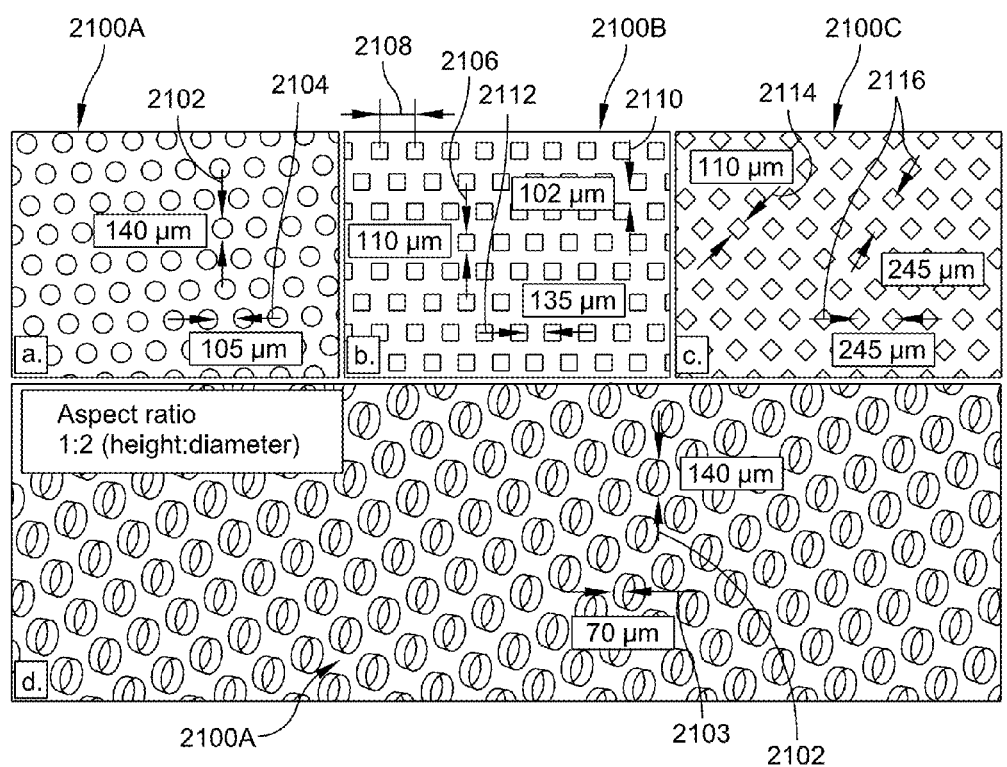
FIG. 21 illustrates an overhead view of the micro-patterns: equally-spaced circular pillars (a), equally-spaced square pillars (b), and equally-spaced rhombus pillars (c), and an isometric view of equally-spaced circular pillars (d)

The base case micro-pattern 2100A (FIG. 21a) was derived from an optimized anchoring design (Rentschler, M., Reid, J., "The Development of a Material Model and Wheel-Tissue Interaction for Simulating Wheeled Surgical Robot Mobility," *Computer Methods in Biomechanics and Biomedical Engineering.* 12(2): 239-248, 2009) including circular pillars of 140 μm in diameter 2012 with a height 2103 forming an aspect ratio (i.e., height:diameter) of 1:2 as illustrated in FIG. 21d. The pillars were equally-spaced at 105 μm edge-to-edge distance 2104 (245 μm center-to-center distance).

Geometrical Variations

It is believed that no one has successfully modeled the contact mechanics between a micro-patterned surface and tissue. It's well known that tissue is viscoelastic in nature, and is inherently rough on a microscopic level. The micro-patterned surface most likely mechanically interacts on a microscopic level to enhance friction, however there are likely to be other contributing forces, such as van der Waals and capillary forces. The capillary forces would be a result of the liquid layer (mucous in a live animal or saline in a laboratory setting)

between the tissue and micro-patterned surface. The presence of liquid will either hinder or enhance the friction between the two surfaces depending on the micro-pattern and the hydrodynamic properties of the material (PDMS). PDMS is naturally hydrophobic, and thus water has a high contact angle when in contact with it (water is repelled).

In an attempt to determine the effect of pillar geometry on friction, micro-patterns of varying pillar geometries were designed. The alternative geometries were designed to introduce edge effects into the micro-pattern in an attempt to disturb fluid flow, and thus capillary forces, along with increasing mechanical engagement. To avoid introducing additional variables, the alternative geometries for the pillars were designed to have equivalent polygonal circumferences, which kept the lateral surface areas of the pillars identical. It was thought that the lateral surface of the pillars would provide the mechanical forces necessary for friction enhancement, as opposed to the top surface of the pillars.

The first geometrical variation was designed so that the faces of the pillars were either perpendicular or parallel to the direction of travel (or fluid flow), which led us to a pillar with a square cross-section. To keep the circumference of all pillars constant (440 µm), the length of the square's side 2106 was set to 110 µm. The aspect ratio of this equally-spaced square pillar tread 21008 (FIG. 21*b*) was kept constant at 1:2. The center-to-center distance 2108 (245 µm) of the micro-pattern was kept constant by setting the vertical edge-to-edge distance 2110 to 102 µm and the horizontal edge-to-edge distance 2112 to 135 µm.

The second geometrical variation may be designed so that the sides of the pillars were neither perpendicular nor parallel to the direction of travel and so that one edge of the pillar was facing the direction of travel. A square pillar 2114, with a side dimension of 110 µm (to keep the circumference of all pillars equivalent) was oriented at an angle of 45 deg. The tilted squares were arranged with 245 µm center-to-center distance 2116 to form an array of rhombus pillars. The aspect ratio of this equally-spaced rhombus pillar tread 2100C (FIG. 21*c*) was kept constant at 1:2.

Fabrication of Micro-Patterned Treads

All of the tread patterns may be fabricated using a photolithography technique. The patterns are computer generated, and transferred to a chrome mask (Fine Line Imaging, Colorado). All three micro-patterns were printed side-by-side on a single 102 millimeters by 102 millimeters mask so that a single mold would produce all three patterns.

Fabrication of SU-8 Mold

In an embodiment, the first part of the photolithography technique results in a wafer coated with SU-8 to a desired thickness (70 µm for the 1:2 aspect ratio.) Then, the wafer incurs a pre-exposure bake including 5 min at 65° C. and then 95° C. for 9 min using a level vacuum hotplate (Fairweather TPS66.) After cooling, the micro-patterns are transferred from the chrome mask to the SU-8 photo-resist using a maskaligner (Suss MJB3 maskaligner.) Using the maskaligner, the chrome side of the mask is placed against the SU-8 on the silicon wafer. Upon contact between the two, an ultraviolet (UV) light is activated from above the mask. The photosensitive SU-8 cross-links as it was exposed to UV light and thus cures while the SU-8 that was not exposed to UV light remained uncured. After UV exposure, the silicon wafer incurred a post-exposure bake identical to the pre-exposure bake. Then, the wafer was submerged in SU-8 developer to remove the uncured SU-8.

Fabrication of Micro-Patterned PDMS Wheels

After fabrication of the SU-8 mold, the mold is used to transfer the micro-pattern onto the surface of a PDMS sample. The PDMS (Dow Corning Sylgard 184 Silicone Elastomer Kit) may be mixed using a 10:1 elastomer to curing agent ratio. Once mixed, the PDMS is thermally cured. During the mixing process, bubbles are introduced into the liquid mixture, so a degassing procedure may be utilized. In one embodiment, the liquid PDMS is placed in an ultrasonic bath for 10 min to help rid the mixture of bubbles. After the ultrasonic bath, the mixture is placed in a 10 ml syringe. To produce a 0.5 mm thick micro-patterned sample, 2.25 ml of liquid PDMS may be poured onto the mold. In addition to, or an alternative to, the ultrasonic bath, the mold may be placed on a level plate in a vacuum oven to facilitate degassing. The PDMS may be cured in a 100° C. oven for 60 minutes and then peeled from the mold.

Prior to testing, the micro-patterned PDMS samples may be inspected under a microscope to verify correct and accurate patterns were produced. The non-patterned side of the PDMS sample may be coated with 100 nm of titanium using a thermal deposition process to produce a surface more susceptible to adhesives. Four cylindrical aluminum wheel hubs (18 mm in diameter and 38 mm wide) may be machined and wrapped in double-sided tape. Each micro-patterned PDMS sample may be wrapped around its own wheel hub to produce three wheels, each coated with a unique micro-pattern: equally spaced circular pillars, equally-spaced square pillars, and equally-spaced rhombus pillars. The fourth cylinder wheel for the test was wrapped with smooth PDMS.

Design of Benchtop Testing Platform

Figure 22:
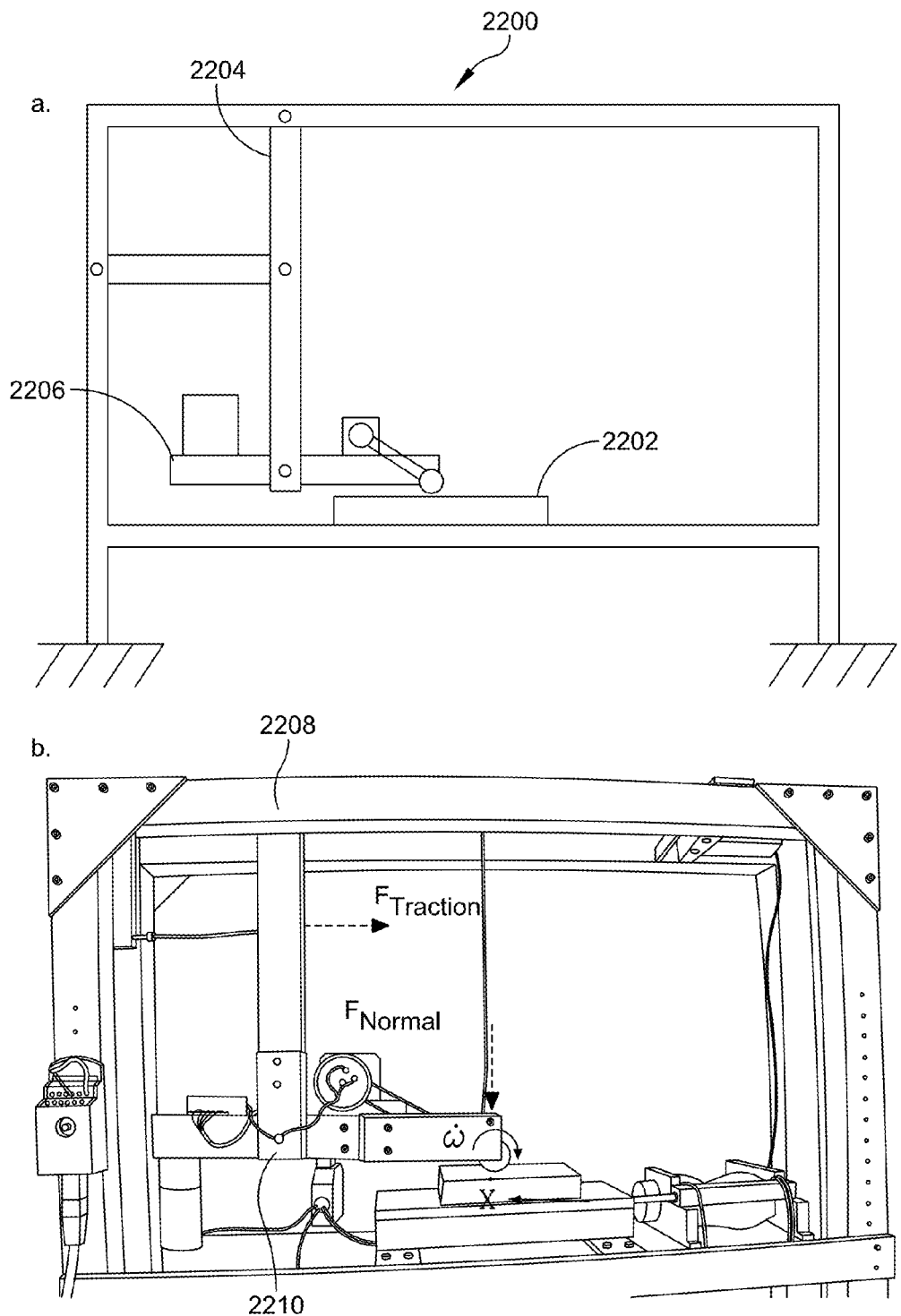
FIG. 22 is a schematic illustration of the benchtop testing platform components (a) and a schematic of the relevant forces (dashed arrows) and velocities (solid black arrows) of the benchtop testing platform (b)

To evaluate the performance of each of the micro-patterned wheels, a custom benchtop testing platform 2200 was designed (FIG. 22). The testing platform needed to evaluate each micro-patterned wheel on various substrates at various predetermined normal forces (i.e., robot weight), and multiple velocity profiles. In order to evaluate the micro-patterned wheels at varying velocity profiles, the testing device needed to be both rotationally and linearly dynamic (i.e., rotate the wheels while providing linear motion). In an attempt to simplify the design the testing platform was designed to rotate a fixed wheel while moving the substrate (i.e., a vehicle driving on a treadmill), which is dynamically synonymous to rotating a wheel while moving it horizontally (i.e., a vehicle driving on the street).

The testing platform was constructed from an aluminum frame foundation. The frame supports two main components: the linear drive system, and the rotational drive system. The linear drive system included a horizontal linear sliding platform 2202 (FIG. 22*a*), a linear actuator (26 DBM12D2B-L, Portescap), and a linear potentiometer (LCP12B-50, ETI Systems). The driving screw of the linear actuator and the wiper on the potentiometer were fixed to the sliding platform. When the linear actuator is activated, the platform moves horizontally, which simultaneously moves the wiper on the potentiometer. The rotational drive system includes a vertical pivoting bar 2204 (FIG. 22*a*) and a horizontal pivoting bar 2206 (FIG. 22*a*). The vertical bar has an attachment point 2208 to the frame (FIG. 22*b*) and hangs freely. The horizontal bar has an attachment point 2210 to the vertical bar. A wheel is attached to an axle (into the page, FIG. 22), on the right side of the horizontal bar. The axle also contains a timing pulley, which is driven by a timing belt and motor (STH-39C804, Shinano Kenshi). The motor shaft is also fixed to the wiper of a rotary potentiometer (132-0-0-103, Spectrol). When the rotary motor is activated, the axle/wheel and wiper of the rotary potentiometer are driven.

Upon activation of the linear actuator, the sliding platform moves with linear velocity x (mm/s) (FIG. 22*b*, solid black arrow). Upon activation of the rotary motor, the wheel moves with an angular velocity $\dot{\theta}$ (rad/s) (FIG. 22b, solid black arrow). The wheel has a known radius r (mm). The following combination of these parameters yields a non-dimensional value termed slip ratio (SR).

$$SR = 1 - \left|\frac{\dot{X}}{r\dot{\theta}}\right| \quad (1)$$

Slip ratio is defined as the ratio between the relative rotational and linear velocities. For the testing platform, slip ratio is the ratio between the linear speed of the substrate platform and the rotational speed of the wheel. Slip ratio can theoretically vary between negative infinite and one. A slip ratio with a value of negative infinite is indicative of a wheel that is not rotating but translating (i.e., pure sliding). A slip ratio with a value of one is indicative of a wheel with a finite rotational speed and no translational speed relative to the substrate (i.e., a stationary vehicle performing a "burnout"). A slip ratio with a value of zero indicates that the relative rotational and translational speeds of the wheel and substrate, respectively, are equivalent (i.e., pure rolling).

Figure 23:
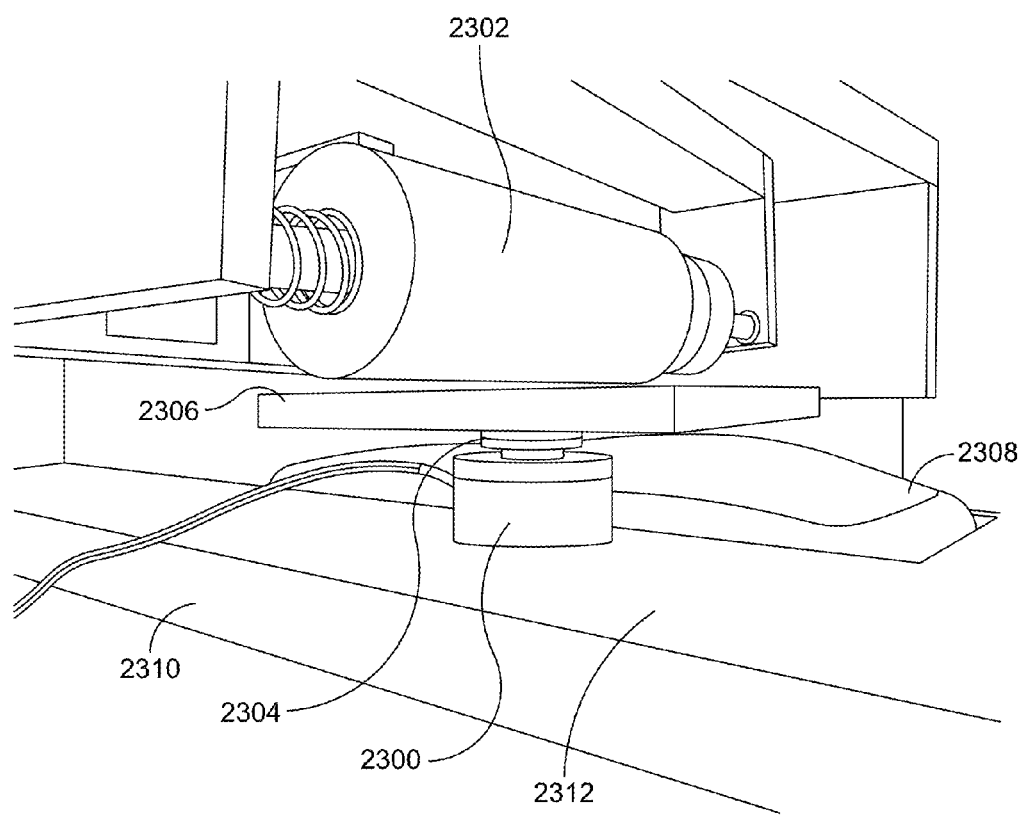
FIG. 23 is a close-up image of the normal force calibration setup. Also pictured is the water bag base for porcine intestine tissue samples to more accurately mimic the viscoelastic nature of an in vivo environment.

In the test platform, wheel traction force ($F_{Traction}$) is a measured quantity, while normal force ($F_{Normal}$), or robot weight, is a controlled quantity (FIG. 22b, dashed arrows). Test values for the normal force are calculated by dividing the weight of the robot by the contact surface area of the treads (for a robot with tank treads) and then multiplying by the contact surface area of a test wheel (most general case). For a future prototype RCE, it was estimated that the contact surface area of the tank treads would be about twice the contact surface area of the test wheel, and that the weight of the prototype robot would be approximately 40 grams, thus, a normal force of 0.20 N. In the interest of understanding the behavior of the micro-patterned treads at higher and lower normal forces, three test weights were chosen: 0.10 N, 0.20 N, and 0.30 N. The normal force at the wheel is adjusted by the addition or removal of counterweights (FIG. 22a). The normal forces were calibrated by placing a load cell force sensor 2300 (ELFM-T2E-25L, Entran), directly under the wheel 2302. The horizontal bar was positioned horizontal by adding or removing spacers 2304 between the load cell 2300 and the platform 2306 (FIG. 23). The load cell 2300 was monitored in real-time using a custom software program (LabVIEW). Counterweights were adjusted until the desired normal forces were achieved, within 0.005 N.

As a wheel rotates on its substrate, it will produce a horizontal drawbar, or traction, force. The horizontal force produced by the test wheel is transferred to a load cell (ESP4-1 KG, Load Cell Central) through the rigid horizontal and vertical bars. The traction force generated at the wheel is magnified by a factor of three by the vertical lever 2204 (FIG. 22a). The wheel on the testing platform is driven clockwise, applying a rightward "pull" force on the load cell. The vertical bar is attached to the load cell using a string, as the force it produces on the load cell is a close approximation to a point load. Attaching the vertical bar to the load cell using a rigid connection created larger variability in the data. The load cell was preloaded by tensioning the string (pulling the vertical bar towards the load cell) in order to ensure that negative traction forces could be measured, where the wheel is being dragged.

A linear solenoid was installed at the top of the frame to automate the testing process. The solenoid was vertically connected to the horizontal bar by a string. When the solenoid is inactive, the string is slack, and the wheel rests on the substrate. When the solenoid is activated, the string becomes taught and lifts the wheel off of the substrate. After each trial, the testing device is reconfigured. As the linear tray and wheel are being reset to their original positions, the solenoid is activated, lifting the wheel and preventing contact during reset. Once the platform is reset, the solenoid is deactivated which causes the wheel to regain contact with the substrate, and the test platform is ready for the next trial.

Due to variations in substrate thickness, occasionally the horizontal bar tilts, leading to offsets in applied normal force and measured traction force. To measure this tilting angle, an accelerometer (SEN-09652, Sparkfun Electronics) was installed on the horizontal bar to constantly monitor tilt. If the variation in the tilt of the bar is significant throughout the tests, these data will be used as a calibration tool.

The sliding platform 2310 has an aluminum tray 2312 fastened to the top of it to accommodate the substrate. The aluminum tray has a recessed area (82 mm×40 mm×5 mm) to help contain a substrate sample (e.g. bovine liver, or porcine intestine). In the case of a bovine liver sample, the tissue is thick enough to be placed by itself in the recessed area. In the case of a porcine intestine sample, the tissue is thin enough that a substrate base is needed to more accurately mimic an in vivo environment. To accomplish this, a custom water-filled latex bag 2308 (82 mm×40 mm×4 mm) was fabricated and placed in the recessed area as a base substrate for porcine intestine samples (FIG. 23).

Experimental Setup

The micro-patterned treads were evaluated using large wheels (relative to tank tread size of future RCEs). Although the micro-patterned PDMS will eventually be used as tank treads, wheels are easier to precisely control, and the relatively large wheel radius approximates a tank tread-tissue interface. Additionally, the large wheels help to increase the signal to noise ratio of the system. In addition to the benchtop platform, the different micro-patterns were compared in an in vivo study using a series of two-wheeled robots with different treads.

Benchtop Evaluation

Four aluminum wheel hubs were coated with a different PDMS treads: equally spaced circular pillars, equally spaced square pillars, equally spaced rhombus pillars, and smooth PDMS. A custom software program (LabVIEW) was set to run the testing device through seven different slip ratios (−0.10, 0.00, 0.05, 0.10, 0.15, 0.20, 0.25). Each set of slip ratios was run at a constant linear speed (i.e., the rotational speed was changed), and repeated three times at various linear speeds (2 mm/s, 3 mm/s and 6 mm/s). Each of the four wheels was evaluated at all slip ratios and all three normal forces (0.10 N, 0.20 N, and 0.30 N) on bovine liver for a total of 252 combinations. Each combination was tried 10 times (i.e., 2520 total trials).

One single trial included a combination of a wheel, normal force, slip ratio, and linear speed. While the motors were running, data was being collected from the load cell (1000 samples/s, 24-bit resolution), linear potentiometer, rotary potentiometer and accelerometer all at 1000 samples/s, 14-bit resolution. Data from the load cell was defined as the traction force, while the linear and rotary potentiometer data were used to calculate induced slip ratio to verify that the actual velocities were equivalent to the desired velocities. Data from the accelerometer was used to verify that the tilt on the horizontal bar remained constant throughout the entirety of the experiment. The motors were programmed to run for 5 s, and data was collected through the entirety of that time for a total of 5000 data points per transducer per trial.

Figure 24:
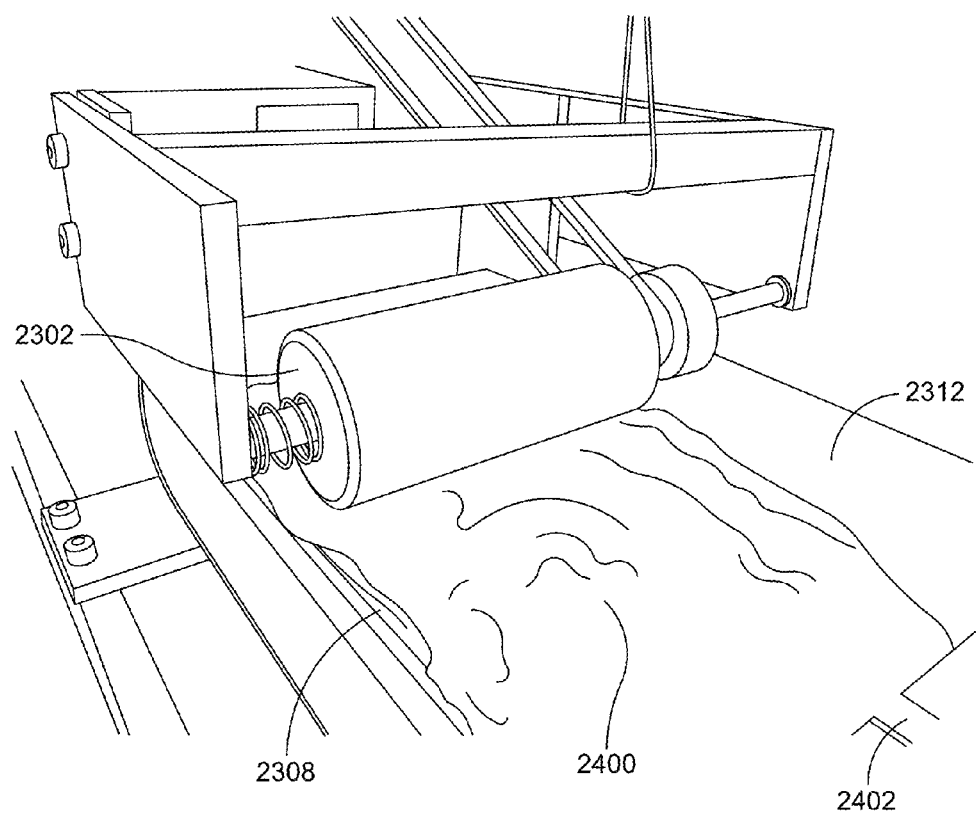
FIG. 24 illustrates an exemplary experimental setup for the dynamic benchtop testing platform in which each micro-patterned PDMS tread is evaluated at three normal force (0.10 N, 0.20 N, 0.30 N), seven slip ratios (−0.10, 0.00, 0.05, 0.10, 0.15, 0.20, 0.25), three linear speeds (2 mm/s, 3 mm/s, 6 mm/s) and one tissue type (bovine liver)

The device was set to autonomously run through 10 trials of 21 slip ratios (210 total trials). This expedited the evaluation process by reducing user input. Upon mounting a wheel, setting a counterweight (normal force), or preparing a tissue sample, the device would autonomously run 210 trials without user input, however during this period (about 20 min) saline would be periodically (approximately every 3 min) sprayed onto the tissue sample to keep the sample hydrated. Each time the user adjusted the device (changed the normal force, tissue sample or wheel), the preload on the normal force would be calibrated (to be subtracted from the data during post-processing). Tissue samples were changed after three sets of 210 trials (all three normal forces), so as to keep the tissue sample the same throughout the evaluation of a single micro-patterned tread (wheel). No noticeable damage to the tissue was observed during the tests, and the order of normal force testing was randomized. Tissue samples 2400 were preheated to room temperature prior to testing, kept hydrated throughout the entirety of testing and secured to the platform using a clip 2402 to prevent lateral sliding (FIG. 24).

In Vivo Tread Comparison Study

Figure 25:
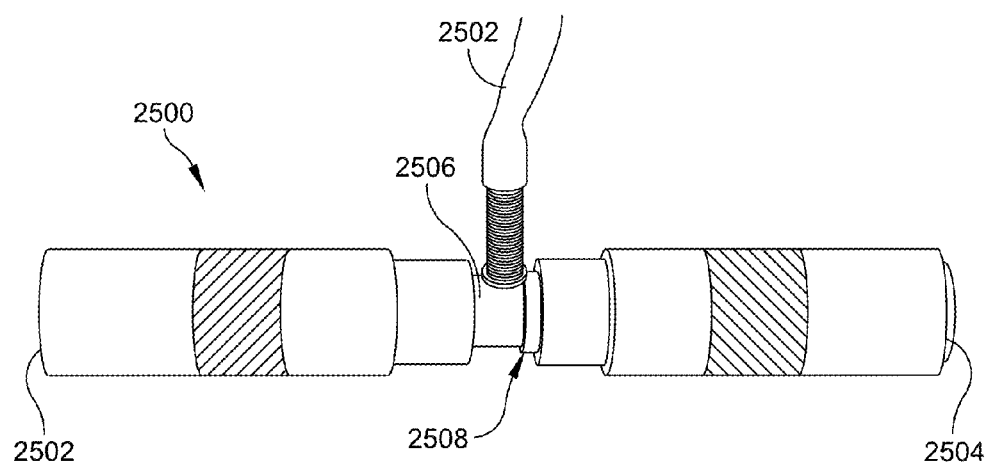
FIG. 25 illustrates a two-wheeled robot for in vivo micro-pattern tread comparison study in which the removable wheels were each covered in a different micro-pattern (green: equally-spaced circular pillars, yellow: equally-spaced square pillars, and red: equally-spaced rhombus pillars)

A comparison study between the different tread patterns was performed in vivo using a series of two-wheeled robots 2500 (FIG. 25). This was completed only to evaluate tread performance and not device design.

The robot body 2500 was constructed using aluminum. A hollow cylinder housed two identical motors 2506, 2508 (0615 C 4.5 S, FAULHABER), each with a 64:1 gear head (06/1 64:1, FAULHABER). The motors were press-fit, end-to-end, within the cylinder so that the shafts of the motors protruded from each end of the cylinder. The robot wheels 2502, 2504 were also made from hollow aluminum cylinders. Each wheel was painted a different color (for identification during the test) and coated with PDMS of varying micro-patterns. To fix a wheel to the robot, it was slid over the hub and around the robot body. Then, the wheel was fastened to the hub with a small screw. Each wheel had an identical surface area and evenly distributed weight. Each motor was capable of clockwise and counterclockwise motions, creating a tank-like steering environment. The robot 2500 included a tether 2502 to provide power and control communications. The symmetrical robot 2500 in this embodiment was 15 mm in diameter, 104 mm long, and weighed 0.29 N.

Results from Benchtop Evaluation

Figure 26:
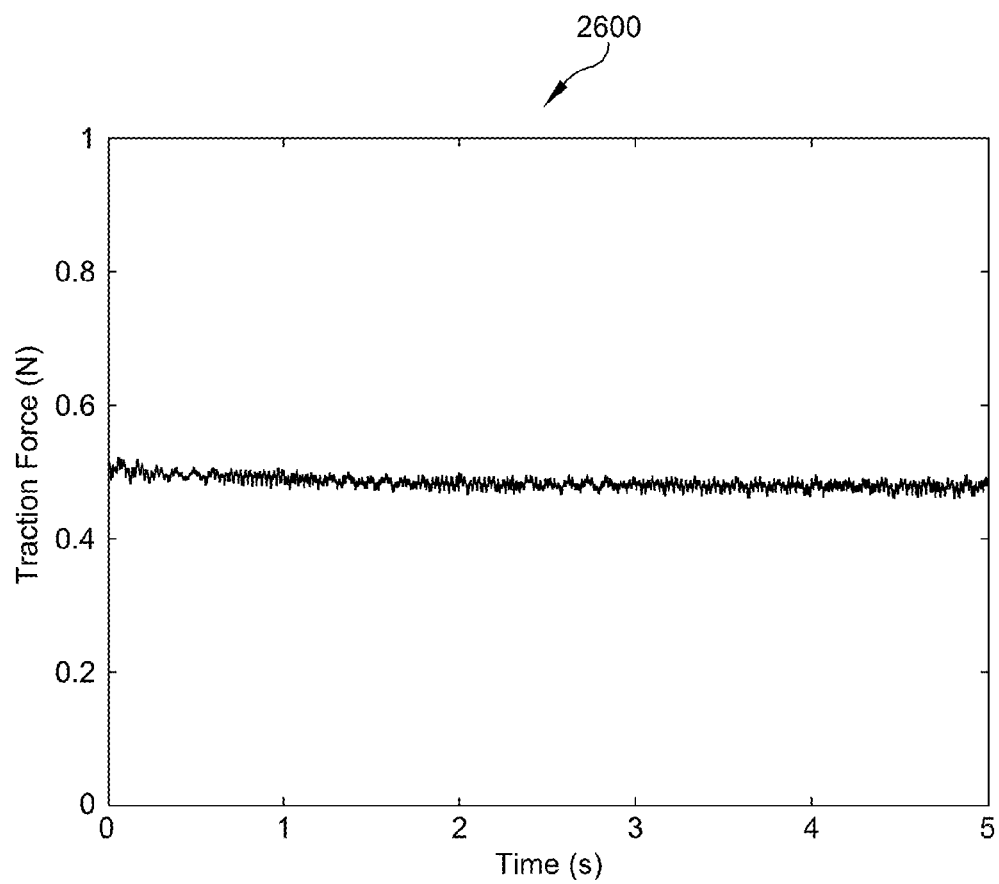
FIG. 26 illustrates typical raw data from one trial from the benchtop testing platform load cell.

Raw data from a typical benchtop experimental trial 2600 looks similar to FIG. 26. The wheels produce a relatively steady-state traction force over the entire trial (5 seconds).

Due to the steady force produced, the 5000 data points were averaged, so that each trial is represented by one value. The 10 trials for each combination are averaged to produce one value, and the standard error is calculated. Traction force generation is shown in the data plots 2700, 2800, 2900, 3000 (FIGS. 27-30) with standard error as the error bars.

Figure 27:
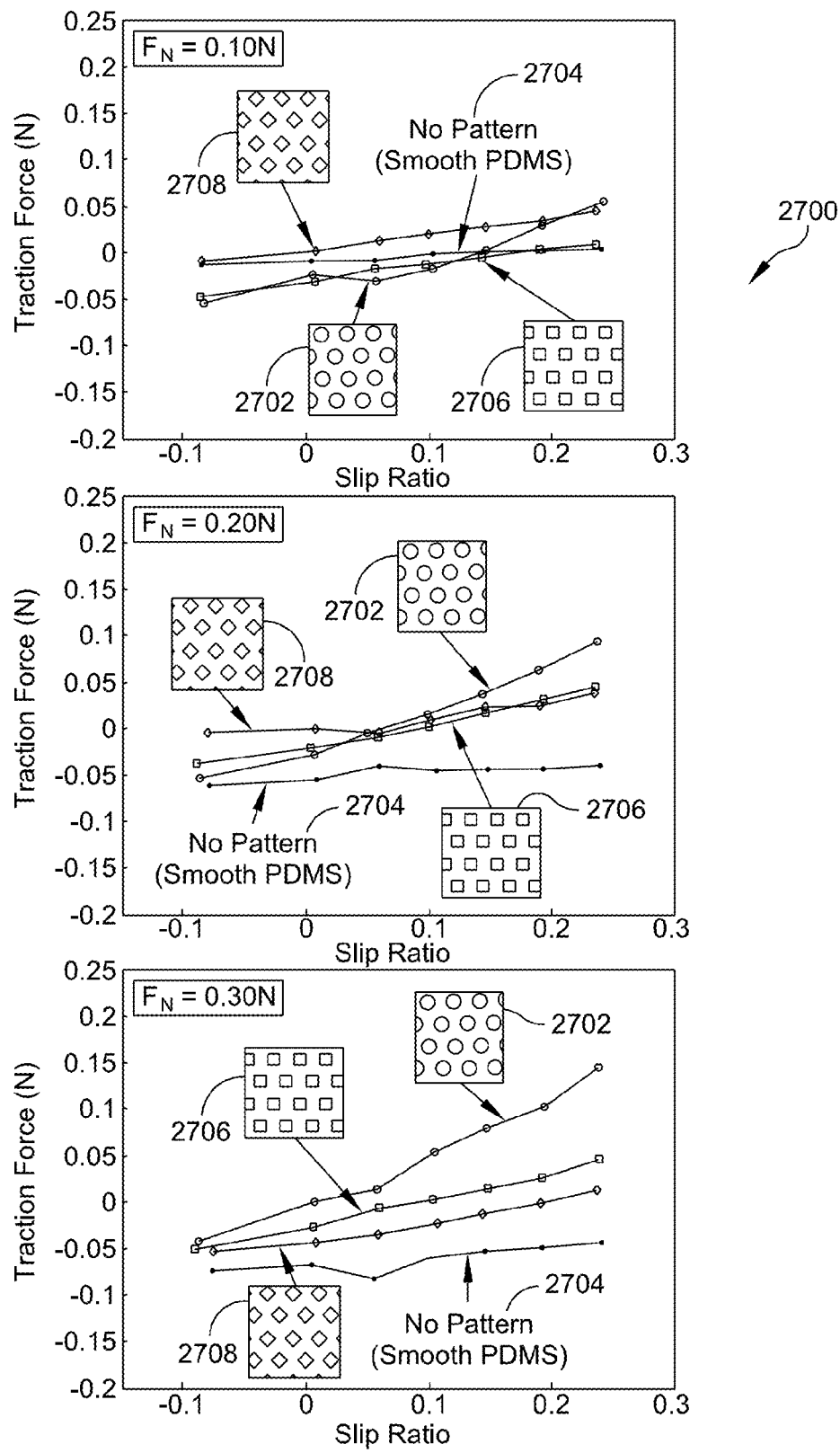
FIG. 27 illustrates a comparison of all micro-patterns at a linear speed of 2 mm/s.
Figure 28:
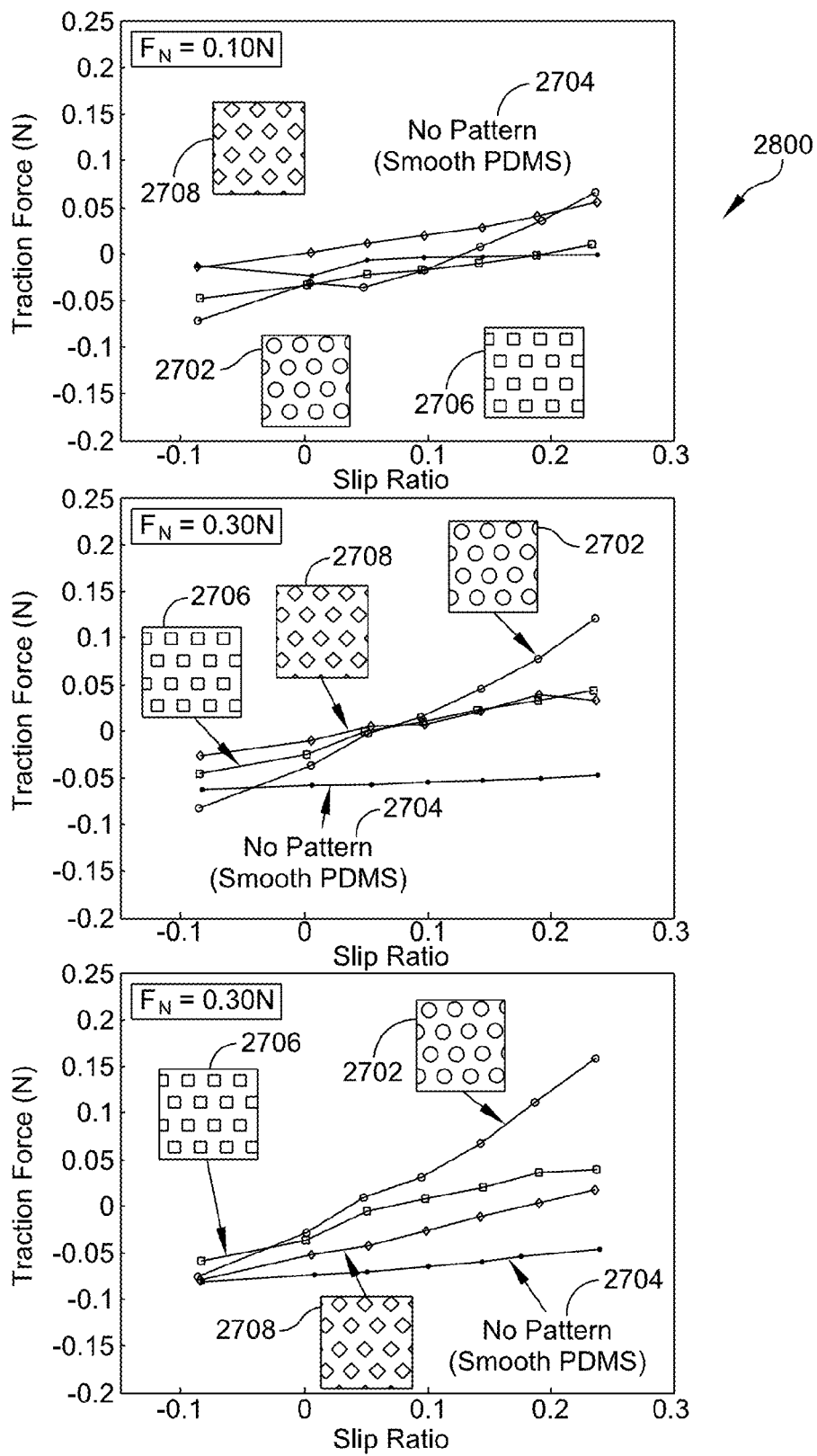
FIG. 28 illustrates a comparison of all micro-patterns at a linear speed of 3 mm/s.
Figure 29:
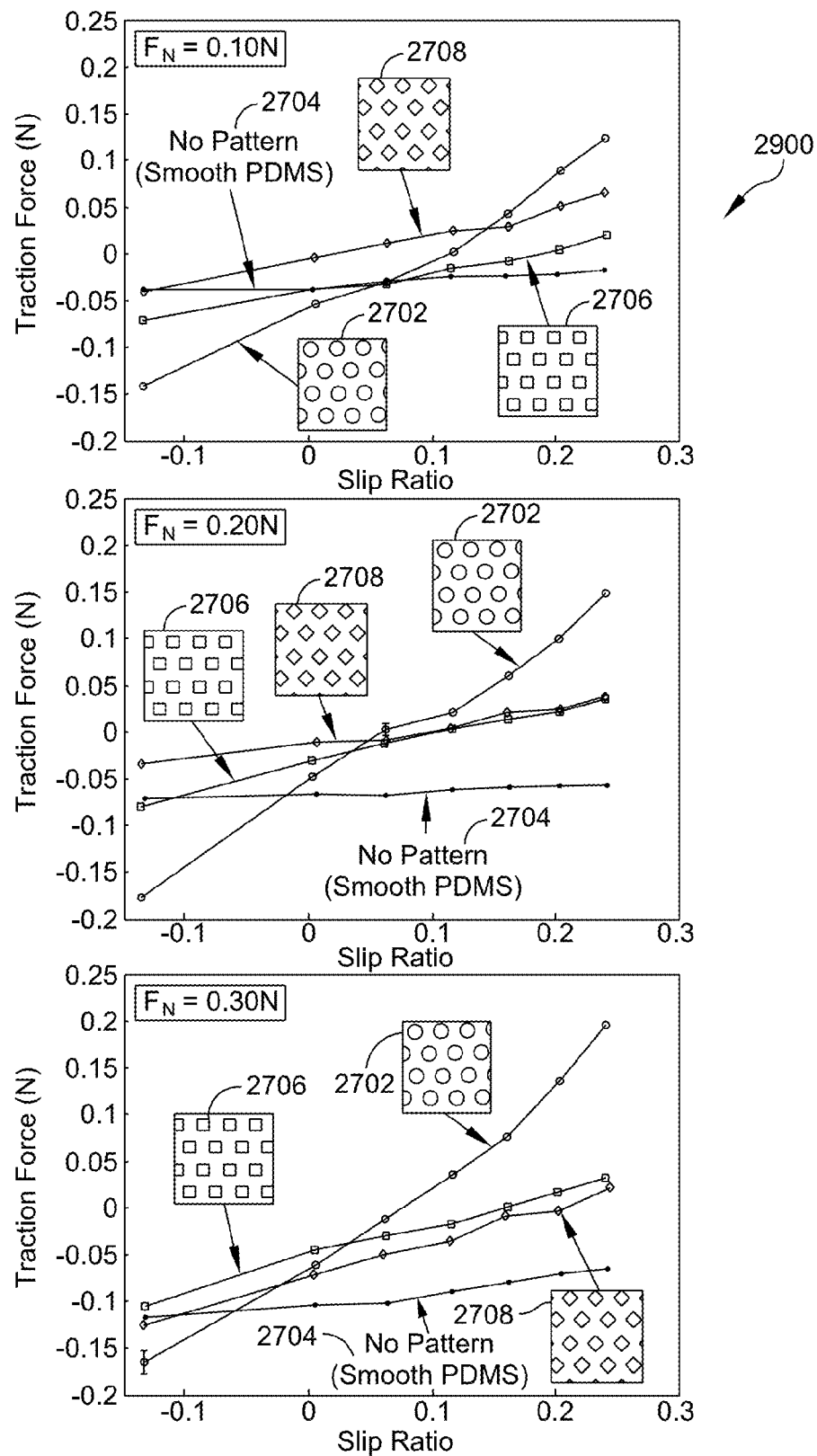
FIG. 29 illustrates a comparison of all micro-patterns at a linear speed of 6 mm/s.

The first relationships to examine are the comparisons between the base case micro-patterned PDMS (equally-spaced circular pillars 2702) and the smooth (no pattern 2704) PDMS (FIGS. 27-29). The traction force produced by the smooth PDMS does not increase significantly with increasing slip ratio. This can be explained by analyzing the forces occurring at the wheel-tissue interface. For smooth PDMS 2704, it is likely that the dominating force producing traction is kinetic friction. Typically, the coefficient of kinetic friction is independent of speed, so with increasing slip ratio, the friction force should not change dramatically. Notice that the smooth PDMS 2704 never produces a positive traction force during any of these tests. This can be explained by examining the dynamics of the experiment. As the wheel rests on the tissue, it depresses into the substrate due to the viscoelastic properties of tissue. The amount of depression increases with increasing normal force. As a test runs, the sliding platform moves towards the load cell. As the wheel rolls, it produces a certain amount of traction, however, the tissue that bulges up on the front side of the wheel, is being pushed against the wheel by the linear tray. In other words, the wheel is being dragged. Most likely this dragging force is much larger than the traction produced by the rotating wheel, and results in a negative traction force for all slip ratios for the smooth wheel.

A similar phenomenon can be observed with the micro-patterned wheel. At negative slip ratios, the dragging force overcomes the traction produced by the wheel resulting in a negative traction force. However, at positive slip ratios, the micro-patterned wheel produces enough traction to overcome the dragging force resulting in positive traction forces. In general, for negative slip ratios, the micro-patterned wheel produces a more negative force than the smooth wheel. This also can be explained by assuming that the micro-patterned wheel is being affected more by the dragging due to the micro-pattern.

Again, examination of the data shown in FIGS. 27-29 reveals information about the effect of varying geometry on traction force production. The first trend to note is that equally-spaced circular pillars (circle) produce more traction force per incremental slip ratio than the equally-spaced square (square 2706) or rhombus (rhombus 2708) pillars (i.e., the slope of circle is larger than the slopes of square or rhombus). Also, the slope of square and rhombus are very similar. In general, the circular fibrils produce a larger traction force than both square and rhombus for all normal forces and linear speeds. Also, it appears that rhombus produces a larger traction force than square at a low normal force for all linear speeds, but produces less traction force than square at a high normal force for all linear speeds. Also, at 0.20 N, rhombus and square appear to perform very similarly.

Figure 30:
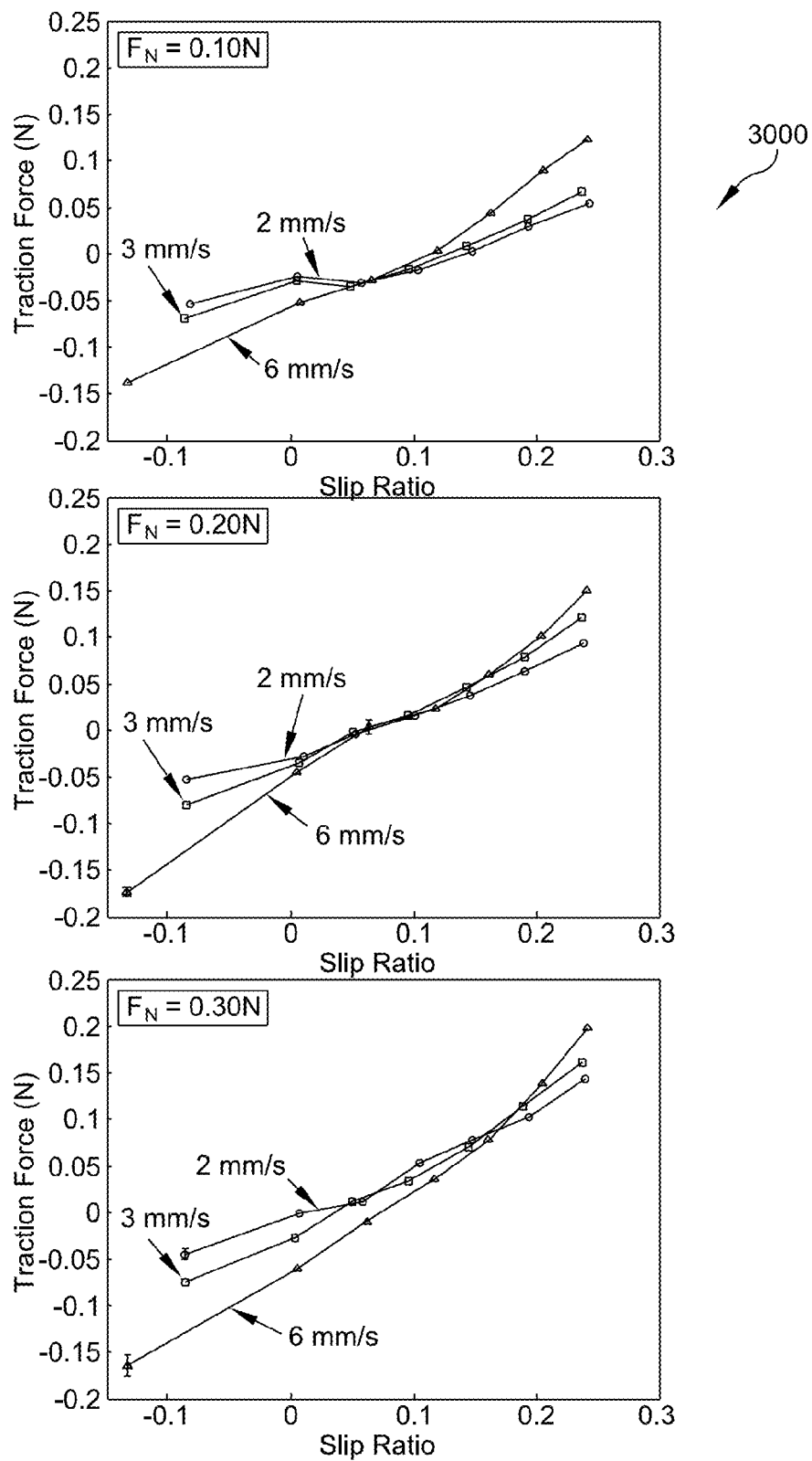
FIG. 30 illustrates a micro-patterned tread (equally-spaced circular pillars) at varying linear speeds and normal forces.

The next plot series 3000 reveals the effect that varying speed has on traction force production (FIG. 30). In these tests, the slip ratios (−0.10, 0.00, 0.05, 0.10, 0.15, 0.20, 0.25), normal forces (0.10 N, 0.20 N, 0.30 N), and tread (equally-spaced circular pillars) remained constant, while the speed at which the wheel rotated and the linear tray moved were varied. For example, for the linear speed to increase from 3 mm/s to 6 mm/s while keeping the slip ratio constant, the rotational speed for the 6 mm/s case must be twice that of the 3 mm/s case. For all three normal forces, traction force is enhanced by slower speeds at low slip ratios, and by faster speeds at higher slip ratios. There is a fairly distinct point at which this relationship inverts for each normal force, and that this point moves to the right (towards higher slip ratios) with increasing normal force. Although the cause of this is unknown at this time, it can be hypothesized that this phenomenon is probably related to the strain rate of the viscoelastic tissue. At high speeds, the wheel pushes against the tissue faster than it does at slow speeds. Viscoelastic material becomes stiffer with increasing speed at which the force is applied, thereby possibly leading to less force loss to tissue resistance.

Results from In Vivo Tread Comparison Study

Figure 31:
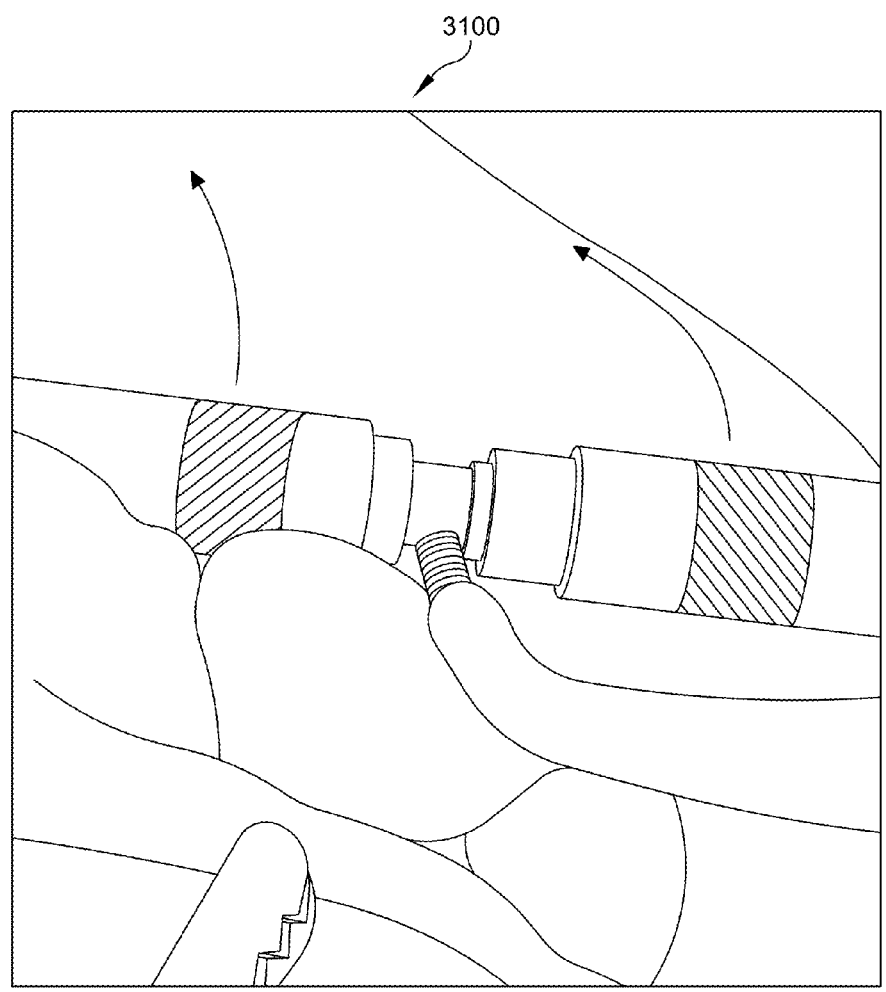
FIG. 31 illustrates results from the in vivo micro-patterned tread comparison study between equally-spaced rhombus pillars and equally-spaced square pillars.

During in vivo testing, the robot 2500 (FIG. 25) was first outfitted with two wheels, equally-spaced square pillars and equally-spaced rhombus pillars. The robot 2500 was placed in an insufflated abdomen of a live anesthetized porcine (pig) model 3100 (FIG. 31).

The robot wheels were activated and it was observed that both treads were obtaining similar traction on the tissue. The wheel with equally spaced square pillars was removed and replaced with the wheel with equally spaced circular pillars, and the comparison test was repeated. Again, the wheels performed similarly. Although there is experimental evidence to claim that the micro-pattern with equally spaced circular pillars performed better than the square and rhombus pillars, the difference is probably not large enough to be observed in this qualitative study on uneven in vivo terrain.

Micro-patterned treads were evaluated using the custom benchtop testing platform and in vivo two-wheeled robots. Throughout benchtop testing, treads were evaluated over a range of slip ratios, from −0.10 to 0.25. It is unrealistic to actually build a robot to operate within the negative slip ratio regime, however, the results from the experimental evaluation are presented because it provides insight for the behavior of the micro-patterned treads. The micro-patterned treads are producing a larger negative traction force at negative slip ratios than the smooth wheel due to the friction enhancement from the micro-pattern.

The results show that there is a significant difference in traction force generation between the square and circular pillars. Also, the results show that there is a significant difference between the rhombus and circular pillars. In both cases, the circular pillars performed better than their counterpart. A conclusion cannot be drawn about any significant difference between the square and rhombus pillars at this point. Based on the major geometrical difference between the square and the circle, and between the rhombus and the circle, it can be inferred that by introducing edge effects into a micro-pattern, the traction force production is decreased. It is possible that by introducing edge effects the efficiency of the micro-patterned tread decreases. In other words, for every incremental increase of slip ratio, the equally spaced circular pillars produce a larger traction force than either the equally-spaced square pillars or the equally-spaced rhombus pillars (i.e., the slope of slip ratio-traction force plot is larger for circular pillars than it is for square or rhombus pillars). According to contact mechanics theory, there are four possible forces contributing to the traction for the micro-patterned wheel: friction, van der Waals forces, capillary forces, and mechanical forces between the micro-pillars and the microscopic surface structure of the tissue. One explanation for the performance differences between the different micro-patterns is that there are capillary forces occurring due to the liquid layer between the tissue and the tread. With angular pillars, the flow might be getting interrupted, resulting in less capillary forces, and thus less traction.

When it comes to designing a micro-patterned tread, this information may be used to create a tread that produces a relatively large amount of traction force with a relatively small amount of slip.

Access to the gastrointestinal (GI) tract is essential for clinical diagnosis, prevention and therapy in GI related pathologies. As a continuation of the outside environment, the GI tract can be accessed through two natural orifices, the oral cavity or the anus. Currently, the most common tool used by physicians during GI surgeries is an endoscope, which is a long flexible tube that is inserted through a natural orifice and advanced to the area of interest. An endoscope is typically equipped with a light source, camera, and a channel to allow entry of surgical instruments. A conventional endoscope can reach the esophagus, stomach and duodenum (esophagogastroduodenoscopy), the small bowel (enteroscopy), and the large bowel and colon (colonoscopy). A long "push" endoscope inserted through the oral cavity can reach the medial small bowel whereas an endoscope inserted through the anus can only reach the distal part of the small bowel. In 2001, double-balloon enteroscopy was introduced as a method of exploring a larger part of the small bowel in either antegrade or retrograde approach. This technology improved handling control, biopsy, and endoscopic treatment. (L. Xin, Z. Liao, Y.-P. Jiang, and Z.-S. Li, "Indications, detectability, positive findings, total enteroscopy, and complications of diagnostic double-balloon endoscopy: a systematic review of data over the first decade of use," Gastrointestinal Endoscopy, vol. 74, no. 3, pp. 563-570, September 2011.) The introduction of the capsule endoscope (CE), a small swallowable pill-shaped camera, enabled total visual exploration of the GI tract, from mouth to anus. Capsule endoscope technology is young, yet has the capacity to replace much of conventional endoscopy. (P. Swain, "The future of wireless capsule endoscopy," *World Journal of Gastroenterology*, vol. 12, no. 26, pp. 4142-4145, July 2008.) Though, to replace conventional endoscopy, a CE may need to be maneuverable and provide equivalent therapies. Unfortunately, the most advanced CEs today are small passive devices with limited power.

Various embodiments provide a mobility system for use in a robotic capsule endoscope 3200 (RCE), implement the most promising mobility design into a RCE prototype, and evaluate the prototype in vivo. The mobility system examined in this work is biologically inspired by the microscopic hairs on the ends of insect feet. Micro-patterns of varying geometry are fabricated on polydimethylsiloxane (PDMS), and formed into wheel coatings (for experimental evaluation) or treads 3202 (for an RCE prototype). The performance (i.e., traction force production) of the micro-patterned PDMS is evaluated on two substrates (bovine liver and synthetic tissue), with various loading and velocity profiles. The specifics of why the micro-pattern enhances friction from a contact mechanical perspective are unknown. The most promising micro-pattern is implemented into an RCE prototype 3200 (FIG. 32) and tested for mobility in the small bowel of a live anesthetized pig. RCE prototype 3200 may include, but is not limited to, rollers 3204 carrying micro-patterned treads 3202; a timing pulley 3206 operably connected to treads 3202; a motor 3208 operably driving treads 3202; a camera and LEDs 3210 for imaging; and a gear train 3212 operable connecting motor 3208 to treads 3202.

There are many diseases associated with the GI tract. Some diseases, such as celiac sprue, can only be diagnosed through biopsy. (P. H. R. Green and C. Cellier, "Celiac Disease," *N Engl J Med*, vol. 357, no. 17, pp. 1731-1743, October 2007.) The available CEs today have no therapeutic capabilities making diagnosis through biopsy impossible. Even if a biopsy tool were implemented on a passive CE, the 3.7 g capsule would be no match for the 100 g push force needed for biopsy or the 400 g pull force needed for tissue resection. (P. Swain, "The future of wireless capsule endoscopy," *World Journal of Gastroenterology*, vol. 12, no. 26, pp. 4142-4145, July 2008.) One approach to providing the additional reaction force for a biopsy would be to implement a mobility system for the CE to enable active pushing and pulling engagement with the lumen wall.

Other diseases, such as colon cancer, can be diagnosed visually, but polyps may only be observed on a small fraction of the available tissue within the GI tract. (P. H. R. Green and C. Cellier, "Celiac Disease," *N Engl J Med*, vol. 357, no. 17, pp. 1731-1743, October 2007.) Additionally, 2.3% of conventional colonoscopies with polypectomies result in complications. (D. A. Fisher et al., "Complications of colonoscopy," *Gastrointestinal endoscopy*, vol. 74, no. 4, pp. 745-752, October 2011.) The most advanced small bowel CE available, the PillCam SB, has an imaging rate of only 4 frames/sec (a fraction of standard video) and a battery life of about 11 h whereas the most advanced esophageal CE on the market, the PillCam ESO, has an imaging rate of 18 frames/sec and a battery life of about 20 min. (P. Swain, "The future of wireless capsule endoscopy," *World Journal of Gastroenterology*, vol. 12, no. 26, pp. 4142-4145, July 2008.) With slow imaging rates and sparsely located cancerous polyps, it could be possible for the PillCam SB to bypass a cancerous polyp during its passive travel through the GI tract. Additionally, for a complete examination of the 5 m long GI tract, a passive capsule would need to run continuously for 24-48 h. An RCE would not only decrease transit time through the GI tract, but also provide maneuverability, so that the physician could orient the device to suit the task at hand (i.e., exploration, drug delivery, biopsy, cauterization, etc.).

Furthermore, for patients with Crohn's disease (an inflammatory bowel disease diagnosable by PillCam), 5% of PillCam procedures result in capsule retention. (D. Cave, P. Legnani, R. de Franchis, and B. S. Lewis, "ICCE consensus for capsule retention," *Endoscopy*, vol. 37, no. 10, pp. 1065-1067, October 2005; and Z. Liao, R. Gao, C. Xu, and Z.-S. Li, "Indications and detection, completion, and retention rates of small-bowel capsule endoscopy: a systematic review," *Gastrointestinal Endoscopy*, vol. 71, no. 2, pp. 280-286, February 2010.) This results in required surgical removal of the PillCam. One approach to improve this outcome is providing the ability to actively maneuver the CE while inside the GI tract.

In Vivo Robotic Mobility

Mobility within the human body on various tissues is possible using a variety of different techniques. The HeartLander robot employs a suction-based drive to move across the surface of a beating heart. (N. A. Patronik, M. A. Zenati, and C. N. Riviere, "Preliminary Evaluation of a Mobile Robotic Device for Navigation and Intervention on the Beating Heart," *Computer Aided Surgery*, vol. 10, no. 4, pp. 225-232, April 2005; and N. A. Patronik, M. A. Zenati, and C. N. Riviere, "Crawling on the Heart: A Mobile Robotic Device for Minimally Invasive Cardiac Interventions," in *Proceedings of the 7th International Conference on Medical Image Computing and Computer-Assisted Intervention (MICCAI)*, Saint-Malo, France, 2004, pp. 9-16.) Other research groups have previously developed a family of in vivo fixed-base and two-wheeled mobile robots, and demonstrated that they can successfully operate within the insufflated abdominal cavity using helical macroscopic tread designs. (M. E. Rentschler, S. M. Farritor, and K. D. Iagnemma, "Mechanical Design of Robotic In Vivo Wheeled Mobility," *Journal of Mechanical Design*, vol. 129, no. 10, pp. 1037-1045, October 2007.) These robots have been used to visually enhance the surgical field for laparoscopic surgeons (M. Rentschler, A. Hadzialic, J. Dumpert, S. Platt, S. Farritor, and D. Oleynikov, "In vivo Robots for Laparoscopic Surgery," presented at the Studies in Health Technology and Informatics—Medicine Meets Virtual Reality, Newport Beach, Calif., USA, 2004, vol. 98, pp. 316-322; and M. Rentschler, J. Dumpert, S. Platt, S. Farritor, and D. Oleynikov, "Mobile In vivo Robots Can Assist In Abdominal Exploration," Fort Lauderdale, Fla., USA, April-2005) and to obtain tissue samples during a single-port liver biopsy in a porcine model. (M. E. Rentschler, J. Dumpert, S. R. Platt, K. Iagnemma, D. Oleynikov, and S. M. Farritor, "An In Vivo Mobile Robot for Surgical Vision and Task Assistance," *Journal of Medical Devices*, vol. 1, no. 1, pp. 23-29, March 2007.)

In previous work (L. J. Sliker, X. Wang, J. A. Schoen, and M. E. Rentschler, "Micropatterned Treads for In Vivo Robotic Mobility," *Journal of Medical Devices*, vol. 4, no. 4, pp. 041006-1-041006-8, December 2010), a two-wheeled robot was developed in an effort to verify a theoretical prediction that a micro-patterned wheel would apply more traction on tissue than a smooth wheel made of the same material. The two-wheeled robot was weight-symmetric, with one micro-patterned wheel and one smooth wheel. Both wheels were made from identical materials. In an in vivo study, the micro-patterned wheel far outperformed the smooth wheel on various tissues within an insufflated porcine abdomen.

Capsule Endoscope Mobility Systems

While previous work (L. J. Sliker, X. Wang, J. A. Schoen, and M. E. Rentschler, "Micropatterned Treads for In Vivo Robotic Mobility," *Journal of Medical Devices*, vol. 4, no. 4, pp. 041006-1-041006-8, December 2010) with wheeled robots has shown that in vivo mobility on a planar surface is possible, this design will be ineffective in uninsufflated cavities and collapsed cylindrical lumens (i.e., GI tract), where fundamentally different mobility approaches and designs are needed.

The simplest such developed in vivo robotic mechanisms for the GI tract are maneuverable endoscopes for colonoscopy and laparoscopy. (T. Fukuda, S. Guo, K. Kosuge, F. Arai, M. Negoro, and K. Nakabayashi, "Micro active catheter system with multi degrees of freedom," in *Proceedings of the 1994 IEEE International Conference on Robotics and Automation*, San Diego, Calif., USA, 1994, vol. 3, pp. 2290-2295.; and K. Suzumori, S. Iikura, and H. Tanaka, "Development of flexible microactuator and its applications to robotic mechanisms," in *Proceedings of the 1991 IEEE International Conference on Robotics and Automation*, Sacramento, Calif., USA, 1991, vol. 2, pp. 1622-1627.) These devices possess actuators to orient the endoscope tip after it enters the body. Other in vivo robots have been developed to explore hollow cavities (e.g., the colon or esophagus) with locomotion systems based on "inch-worm" motion. For mobility, these robots use either a series of grippers and extensors (L. Phee, D. Accoto, A. Menciassi, C. Stefanini, M. C. Carrozza, and P. Dario, "Analysis and development of locomotion devices for the gastrointestinal tract," *IEEE Transactions on Biomedical Engineering*, vol. 49, no. 6, pp. 613-616, June 2002), rolling tracks (A. M. Flynn, K. R. Udayakumar, D. S. Barrett, J. D. McLurkin, D. L. Franck, and A. N. Schectman, "Tomorrow's surgery: Micromotors and microrobots for minimally invasive procedures," *Minimally Invasive Therapy & Allied Technologies*, vol. 7, no. 4, pp. 343-352, January 1998), rolling stents (P. Breedveld, D. E. van der Kouwe, and M. A. J. van Gorp, "Locomotion Through the Intestine by Means of Rolling Stents," in *28th Biennial Mechanisms and Robotics Conference, Parts A and B, Salt Lake City, Utah, USA,* 2004, vol. 2, pp. 963-969), rotational motion of a spiral-shaped body (Y.-T. Kim and D.-E. Kim, "Novel Propelling Mechanisms Based on Frictional Interaction for Endoscope Robot," *Tribology Transactions*, vol. 53, no. 2, pp. 203-211, January 2010), a magnetically actuated tail (E. Morita et al., "In vivo trial of a driving system for a self-propelling capsule endoscope using a magnetic field (with video)," *Gastrointestinal Endoscopy*, vol. 72, no. 4, pp. 836-840, October 2010), magnetic propulsion (G. Kosa, P. Jakab, F. Jolesz, and N. Hata, "Swimming capsule endoscope using static and RF magnetic field of MRI for propulsion," in *IEEE International Conference on Robotics and Automation*, Pasadena, Calif., USA, 2008, pp. 2922-2927), or electrical stimulation of the GI muscles. (A. C. Mosse, T. N. Mills, M. N. Appleyard, S. S. Kadirkamanathan, and P. C. Swain, "Electrical stimulation for propelling endoscopes," *Gastrointestinal Endoscopy*, vol. 54, no. 1, pp. 79-83, July 2001.) Stefanini et al., Menciasi et al., and Valdastri et al. recently described an endoscopic pill with an active locomotion system that uses legs to push against the gastrointestinal walls (C. Stefanini, A. Menciassi, and P. Dario, "Modeling and Experiments on a Legged Microrobot Locomoting in a Tubular, Compliant and Slippery Environment," *The International Journal of Robotics Research*, vol. 25, no. 5-6, pp. 551-560, May 2006; A. Menciassi et al., "Locomotion of a legged capsule in the gastrointestinal tract: theoretical study and preliminary technological results," in *26th Annual International Conference of the IEEE Engineering in Medicine and Biology Society*, 2004, vol. 1, pp. 2767-2770; and P. Valdastri, R. J. Webster, C. Quaglia, M. Quirini, A. Menciassi, and P. Dario, "A New Mechanism for Mesoscale Legged Locomotion in Compliant Tubular Environments," *IEEE Transactions on Robotics*, vol. 25, no. 5, pp. 1047-1057, October 2009), a system that uses an external magnetic field to move the device through the intestine (G. Ciuti, P. Valdastri, A. Menciassi, and P. Dario, "Robotic magnetic steering and locomotion of capsule endoscope for diagnostic and surgical endoluminal procedures," *Robotica*, vol. 28, no. 2, pp. 199-207, October 2009), and a system that combines these two systems. (M. Simi, P. Valdastri, C. Quaglia, A. Menciassi, and P. Dario, "Design, Fabrication, and Testing of a Capsule With Hybrid Locomotion for Gastrointestinal Tract Exploration," *IEEE/ASME Transactions on Mechatronics*, vol. 15, no. 2, pp. 170-180, April 2010.) Menciassi et al. also describe a clamping system that uses shape memory alloys. (A. Menciassi, A. Moglia, S. Gorini, G. Pernorio, C. Stefanini, and P. Dario, "Shape memory alloy clamping devices of a capsule for monitoring tasks in the gastrointestinal tract," *Journal of Micromechanics and Microengineering*, vol. 15, no. 11, pp. 2045-2055, September 2005.) Additionally, Harada et al. describe a modular robot that enters the body in subsections through the mouth, assembles itself within the gastric cavity for a surgical task, and then disassembles itself upon completion of the task for natural excretion. (K. Harada et al., "A reconfigurable modular robotic endoluminal surgical system: vision and preliminary results," *Robotica*, vol. 28, no. 2, pp. 171-183, December 2009.) Finally, Sitti et al. describe a method of anchoring a capsule endoscope within the GI tract using micro-patterned PDMS (P. Glass, E. Cheung, and M. Sitti, "A Legged Anchoring Mechanism for Capsule Endoscopes Using Micropatterned Adhesives," *IEEE Transactions on Biomedical Engineering*, vol. 55, no. 12, pp. 2759-2767, December 2008; and E. Cheung, M. E. Karagozler, S. Park, B. Kim, and M. Sitti, "A new endoscopic microcapsule robot using beetle inspired microfibrillar adhesives," in *Proceedings IEEE/ASME International Conference on Advanced Intelligent Mechatronics*, 2005, pp. 551-557), and an inchworm legged robot using micro-patterned PDMS. (M. E. Karagozler, E. Cheung, J. Kwon, and M. Sitti, "Miniature Endoscopic Capsule Robot using Biomimetic Micro-Patterned Adhesives," in *Proceedings IEEE/RAS-EMBS International Conference on Biomedical Robotics and Biomechatronics*, 2006, pp. 105-111.)

Micro-patterned treads that allow for nearly continuous tissue-RCE contact. This distributed approach helps maximize traction and propulsion, while providing stability and minimizing drag.

Micro-patterning has been used in many applications, ranging from fluids to friction enhancement. The friction enhancement properties of micro-patterning are of interest to gain traction in vivo. Micro-patterning for friction enhancement stems from a biological phenomenon found on the feet of various animals, such as beetles and geckos. Terrestrial animals have evolved to develop one of two different micro-patterns on the pads of their feet to enhance friction for locomotion on a variety of different substrates: hairy pads and smooth pads. (R. G. Beutel and S, N. Gorb, "Ultrastructure of attachment specializations of hexapods (Arthropoda): evolutionary patterns inferred from a revised ordinal phylogeny," *Journal of Zoological Systematics and Evolutionary Research*, vol. 39, no. 4, pp. 177-207, December 2001; and R. G. Beutel and S, N. Gorb, "A Revised Interpretation of the Evolution of Attachment Structures in Hexapoda with Special Emphasis on Mantophasmatodea," *Arthropod Systematics & Phylogeny*, vol. 64, no. 1, pp. 3-25, October 2006.) Both types of pads are able to match the surface structure of their respective substrates, maximizing the contact surface area, and thus increasing the frictional and adhesive properties of the feet. (S. Gorb, "Biological microtribology: anisotropy in frictional forces of orthopteran attachment pads reflects the ultrastructure of a highly deformable material," *Proceedings of the Royal Society of London. Series B: Biological Sciences*, vol. 267, no. 1449, pp. 1239-1244, June 2000; S, N. Gorb, *Attachment Devices of Insect Cuticle*. New York, N.Y.: Springer, 2001; and B. N. J. Persson and S, N. Gorb, "The effect of surface roughness on the adhesion of elastic plates with application to biological systems," *Journal of Chemical Physics*, vol. 119, no. 21, pp. 11437-11444, December 2003.) Micro-patterned (circular pillars) PDMS has been used as a method for anchoring and mobilizing a capsule robot in the small intestine. (P. Glass, E. Cheung, and M. Sitti, "A Legged Anchoring Mechanism for Capsule Endoscopes Using Micropatterned Adhesives," *IEEE Transactions on Biomedical Engineering*, vol. 55, no. 12, pp. 2759-2767, December 2008.; E. Cheung, M. E. Karagozler, S. Park, B. Kim, and M. Sitti, "A new endoscopic microcapsule robot using beetle inspired microfibrillar adhesives," in *Proceedings IEEE/ASME International Conference on Advanced Intelligent Mechatronics*, 2005, pp. 551-557; and M. E. Karagozler, E. Cheung, J. Kwon, and M. Sitti, "Miniature Endoscopic Capsule Robot using Biomimetic Micro-Patterned Adhesives," in *Proceedings IEEE/RAS-EMBS International Conference on Biomedical Robotics and Biomechatronics*, 2006, pp. 105-111.) The legs of the anchoring device were coated with the micro-patterned PDMS and friction between PDMS and porcine intestine was measured. Results of the study showed that dry PDMS with a micro-pattern produced 50-100% more traction than flat surfaces. Additionally, PDMS coated with a thin layer of silicone oil results in as much as a 400% friction improvement. Most recently, Buselli et al. have placed micropatterned pads on the ends of the legs of the device (C. Stefanini, A. Menciassi, and P. Dario, "Modeling and Experiments on a Legged Microrobot Locomoting in a Tubular, Compliant and Slippery Environment," *The International Journal of Robotics Research*, vol. 25, no. 5-6, pp. 551-560, May 2006; A. Menciassi et al., "Locomotion of a legged capsule in the gastrointestinal tract: theoretical study and preliminary technological results," in *26th Annual International Conference of the IEEE Engineering in Medicine and Biology Society*, 2004, vol. 1, pp. 2767-2770; and P. Valdastri, R. J. Webster, C. Quaglia, M. Quirini, A. Menciassi, and P. Dario, "A New Mechanism for Mesoscale Legged Locomotion in Compliant Tubular Environments," *IEEE Transactions on Robotics*, vol. 25, no. 5, pp. 1047-1057, October 2009) to enhance the friction at the leg-tissue interface. (E. Buselli, V. Pensabene, P. Castrataro, P. Valdastri, A. Menciassi, and P. Dario, "Evaluation of friction enhancement through soft polymer micro-patterns in active capsule endoscopy," *Measurement Science and Technology*, vol. 21, no. 10, pp. 105802-1-105802-7, September 2010.)

Benchtop Tread Testing

Conceptual micro-patterned treads were designed, fabricated, and tested on several substrates. All micro-patterns were tested against a smooth (non-patterned) PDMS surface.

A series of micro-patterned treads were designed for tread performance testing. A base case was generated from a previously optimized design (M. E. Karagozler, E. Cheung, J. Kwon, and M. Sitti, "Miniature Endoscopic Capsule Robot using Biomimetic Micro-Patterned Adhesives," in *Proceedings IEEE/RAS-EMBS International Conference on Biomedical Robotics and Biomechatronics*, 2006, pp. 105-111), along with additional tread patterns that were designed to investigate edge effects within the pattern.

Figure 33:
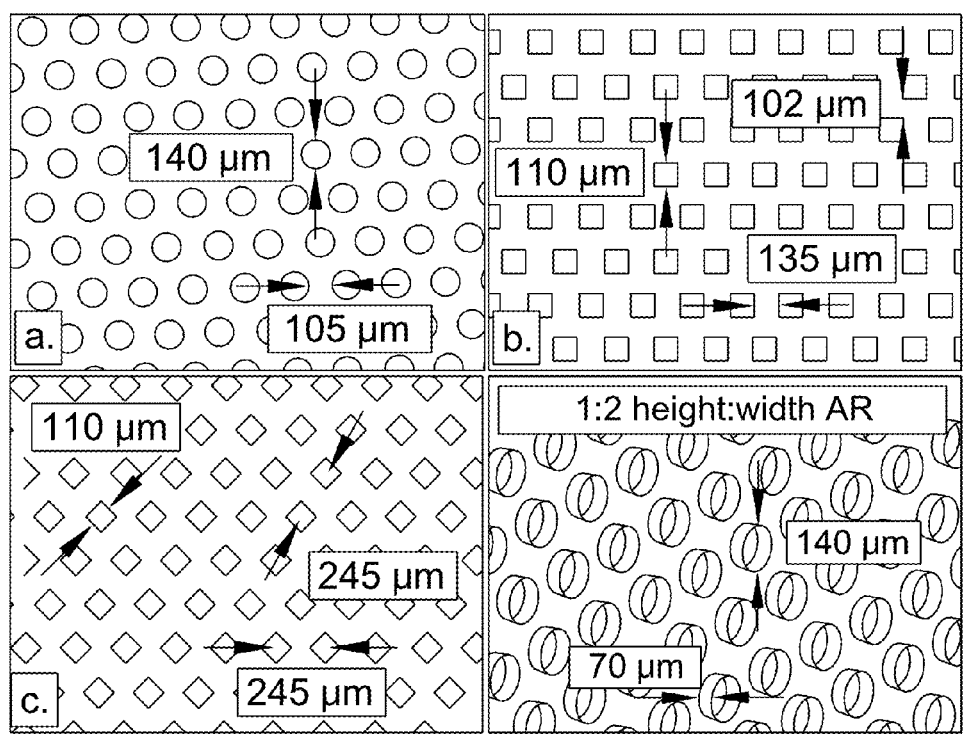
FIG. 33 illustrates various pillar geometries for the micro-patterned polydimethylsiloxane (PDMS) treads include equally-spaced circular (a), square (b), and diamond (c). The height-to-width aspect ratio (AR) of all micro-patterns was 1:2 (d)

The base case micro-pattern (FIG. 33a) was derived from an optimized anchoring design (M. E. Karagozler, E. Cheung, J. Kwon, and M. Sitti, "Miniature Endoscopic Capsule Robot using Biomimetic Micro-Patterned Adhesives," in *Proceedings IEEE/RAS-EMBS International Conference on Biomedical Robotics and Biomechatronics*, 2006, pp. 105-111) including circular pillars 140 µm in diameter with an aspect ratio (i.e., height:diameter) of 1:2 (FIG. 33d). The pillars were equally-spaced at 105 µm edge-to-edge distance (245 µm center-to-center distance.)

The geometry of the micro-pillars was varied to induce different edge effects into the pattern. All pillar geometries were designed to have equivalent polygonal circumferences. The first geometrical variation was designed so that the faces of the pillars were either perpendicular or parallel to the direction of travel, which led to a pillar with a square cross-section (FIG. 33b). To keep the circumference of all pillars constant (440 µm), the length of the square's side was set to 110 µm. The aspect ratio of this equally spaced square pillar tread was kept constant at 1:2. The center-to-center distance (245 µm) of the micro-pattern was kept constant by setting the vertical edge-to-edge distance to 102 µm and the horizontal edge-to-edge distance to 135 µm.

The second geometrical variation was designed so that the sides of the pillars were neither perpendicular nor parallel to the direction of travel and so that one edge of the pillar was facing the direction of travel. A square pillar, with a side dimension of 110 µm (to keep the circumference of all pillars equivalent) was oriented at an angle of 45 deg (FIG. 33c). The tilted squares (diamonds) were arranged with 245 µm center-to-center distance to form an array of diamond pillars. The aspect ratio of this equally-spaced diamond pillar tread was kept constant at 1:2.

Micro-Patterned Tread Fabrication

Tread fabrication includes micro-pattern SU-8 mold fabrication, and micro-pattern transfer onto PDMS. Due to its biocompatibility, accessibility, ease of use, and hydrophobicity, PDMS was chosen as a polymer for the micro-pattern fabrication. However, other suitable materials may be selected for micro-pattern tread fabrication. Examples include, but are not limited to perfluoropolyether (PFPE), Objet VeroWhitePlus RGD835 (which is a material simulating standard plastic, rigid opaque materials, from the Objet datasheet), or Objet TangoBlackPlus FLX980 (which is a material simulating standard plastic, rubber-like materials, from the Objet datasheet).

The SU-8 mold may be fabricated on a 76.2 millimeters (3 inches) silicon wafer using a standard photolithography technique. The patterns may be computer generated and printed on a chrome mask (Fine Line Imaging, Colorado, USA). SU-8 3050 photoresist (MicroChem. Corp., Newton, Mass., USA) may be spun (2000 RPM, 255 RPM/s, 30 sec) onto the wafer to obtain the 70 µm thickness. The mask may be used to transfer the micro-pattern to the photoresist. After the post-exposure bake and development, 1 ml of Omnicoat (MicroChem. Corp.) was spun (500 RPM, 100 RPM/s, 30 sec) onto the mold to facilitate removal of the PDMS.

The SU-8 mold may be used to transfer the micro-pattern onto the surface of a PDMS sample. The PDMS (Dow Corning Sylgard 184 Silicone Elastomer Kit) may be mixed using a 10:1 elastomer to curing agent ratio. Then, 2.25 ml of liquid PDMS may be poured onto the SU-8 mold to produce a 0.5 mm thick sample. The mold may be placed on a level plate in a vacuum chamber to facilitate degassing. Once all (or at least a portion of) the bubbles are removed, the PDMS may be thermally cured in a 100° C. oven for 60 minutes and then peeled from the mold. Micro-patterned PDMS samples may be inspected under a microscope to verify correct and accurate patterns were produced.

For experimental testing of the treads, four cylindrical aluminum wheel hubs (18 mm in diameter and 38 mm wide) were machined and wrapped in double-sided tape. Each micro-pattern was wrapped around its own wheel hub to produce three wheels, each coated with a unique micro-pattern: equally spaced circular pillars, equally spaced square pillars, and equally spaced diamond pillars. The fourth cylinder wheel was wrapped with smooth PDMS.

Benchtop Testing Platform

Figure 34:
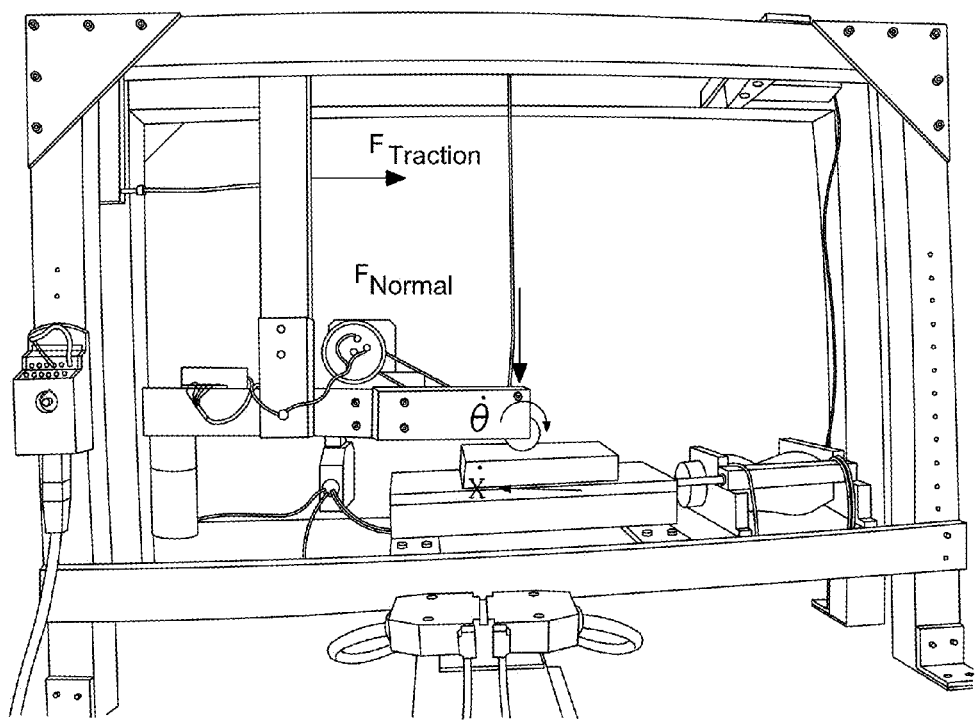
FIG. 34 illustrates the experimental testing device used to quantitatively measure the performance of the wheels on the synthetic tissue in which the device measures wheel traction under variable normal forces, and rotational and linear velocities.

A previously designed (L. J. Sliker, X. Wang, J. A. Schoen, and M. E. Rentschler, "Micropatterned Treads for In Vivo Robotic Mobility," *Journal of Medical Devices*, vol. 4, no. 4, pp. 041006-1-041006-8, December 2010; and L. J. Sliker and M. E. Rentschler, "The Design and Characterization of a Novel Testing Device for Qualitative Evaluation of Wheel Performance on Varying Substrates," *Transactions on Biomedical Engineering*, Under Review) testing device (FIG. 34) was used to evaluate the micro-patterned wheels. The device was designed to simulate the dynamics that occur as a wheel rolls across a substrate. The device is outfitted with a translating linear tray that can be actuated (26 DBM10D2B-L, Portescap, Malaysia) with linear speed $\dot{x}$ (mm/s), and a rotating axle that can be actuated (SST40C1010, Shinano Kenshi, Corp., Culver City, Calif., USA) with rotational speed $\dot{\theta}$ (rad/s). The axle facilitates interchangeable micro-patterned wheels, with radius r (mm). An open-loop controller (ROB-10267, Sparkfun Electronics, Boulder, Colo., USA) can precisely set the speeds of the wheel and the tray to induce various slip ratios ($r_s$).

$$r_s = 1 - \left|\frac{\dot{x}}{r\dot{\theta}}\right| \tag{1}$$

Slip ratio is a measure of percent slip. If $\dot{x}$ is larger than $r\dot{\theta}$ (i.e., the tray is moving faster than the tangential velocity of the wheel at the radius), then slip ratio is negative. If $\dot{x}$ is smaller than $r\dot{\theta}$ (i.e., the tray is moving slower than the tangential velocity of the wheel at the radius), then slip ratio is positive. Negative slip ratios are indicative of wheel dragging or braking, whereas positive slip ratios are indicative of wheel slipping (i.e., a burnout). For example, if $r_s=-0.1$, then $\dot{x}$ is 10% faster than $r\dot{\theta}$, and if $r_s=0.1$, then $\dot{x}$ is 10% slower than $r\dot{\theta}$. The linear and rotational velocity data are recorded using a linear and rotary potentiometer, respectively. The data is post-processed to verify that the desired speed matches the actual speed. The slip ratios induced for these tests were [−0.10, 0.00, 0.05, 0.10, 0.15, 0.20, 0.25] for beef liver, and [−0.30, −0.25, −0.20, −0.15, −0.10, −0.05, 0.00, 0.05, 0.10, 0.15, 0.20, 0.25, 0.30] for synthetic tissue. A smaller range of slip ratios was used for beef liver to decrease the length of the test, so that the condition of the tissue would remain relatively constant throughout the test.

The axle is fixed to a series of lever arms, which amplifies and applies the traction force to a load cell (ESP4-1, Load Cell Central, Monroeton, Pa., USA). The resolution of the force data (collected at 1000 samples/s, 24-bit ND converter) is 0.002 N.

The normal force of the wheel can be varied between three set weights (0.10 N, 0.20 N, and 0.30 N) by changing out the counterweight.

An automated LabVIEW program runs a given wheel/normal force/substrate combination through the range of slip ratios for that substrate. A single trial is defined as inducing one slip ratio for a period of 5 s (resulting in 5,000 data points). Each slip ratio is induced at three linear speeds (2 mm/s, 3 mm/s and 6 mm/s). Each trial is repeated 5 times for a total of 195 trials for synthetic tissue and 10 times for a total of 1,050 trials for beef liver. More trials were used for the real tissue due to its increased variability. Before each run, the load cell is calibrated. After a run, the normal force, substrate or wheel is changed, until data from all wheel, substrate and normal force combinations has been taken.

Substrate Preparation

All combinations of wheel, slip ratio, linear speed, and normal force (252 combinations for beef liver and 468 combinations for synthetic tissue) were repeated on three different substrates; beef liver, hydrated synthetic tissue, and dry synthetic tissue.

Beef liver was chosen as a substrate because it is a readily available tissue that exhibits viscoelastic properties inherent to all tissues. Although the properties do not exactly match those of GI tissue, they are a close viscoelastic approximation. Each automated test lasted about 20 minutes, so the tissue sample was replaced before each run, and was kept hydrated with 0.9% PBS (phosphate buffer solution) throughout each run. Liver samples were prepared with equivalent dimensions and similar topographies.

The synthetic tissue (TSM-10, Simulab Corp., Seattle, Wash., USA) substrate was chosen as a comparison to the real tissue. One piece of synthetic tissue was used for all of the tests. For the hydrated tests, the synthetic tissue was submerged in a 0.9% PBS bath.

The traction force production over the course of a 5 second trial was steady state, so the data (5,000 points) was averaged for each trial. The trials (10 for beef liver, 5 for synthetic tissue—less trials for synthetic tissue as repeatability error was much lower) were averaged and the standard error was calculated at each slip ratio. The standard error at each point was compared to the error of the load cell, and the larger of the two was reported. The traction force data is converted to a "performance" (i.e., a lumped coefficient of friction) by dividing by the applied normal force. Finally, the force data is plotted against slip ratio. The following discussion encompasses the effects that varying speed, hydration, and micro-pattern geometry have on tread performance.

Figure 35:
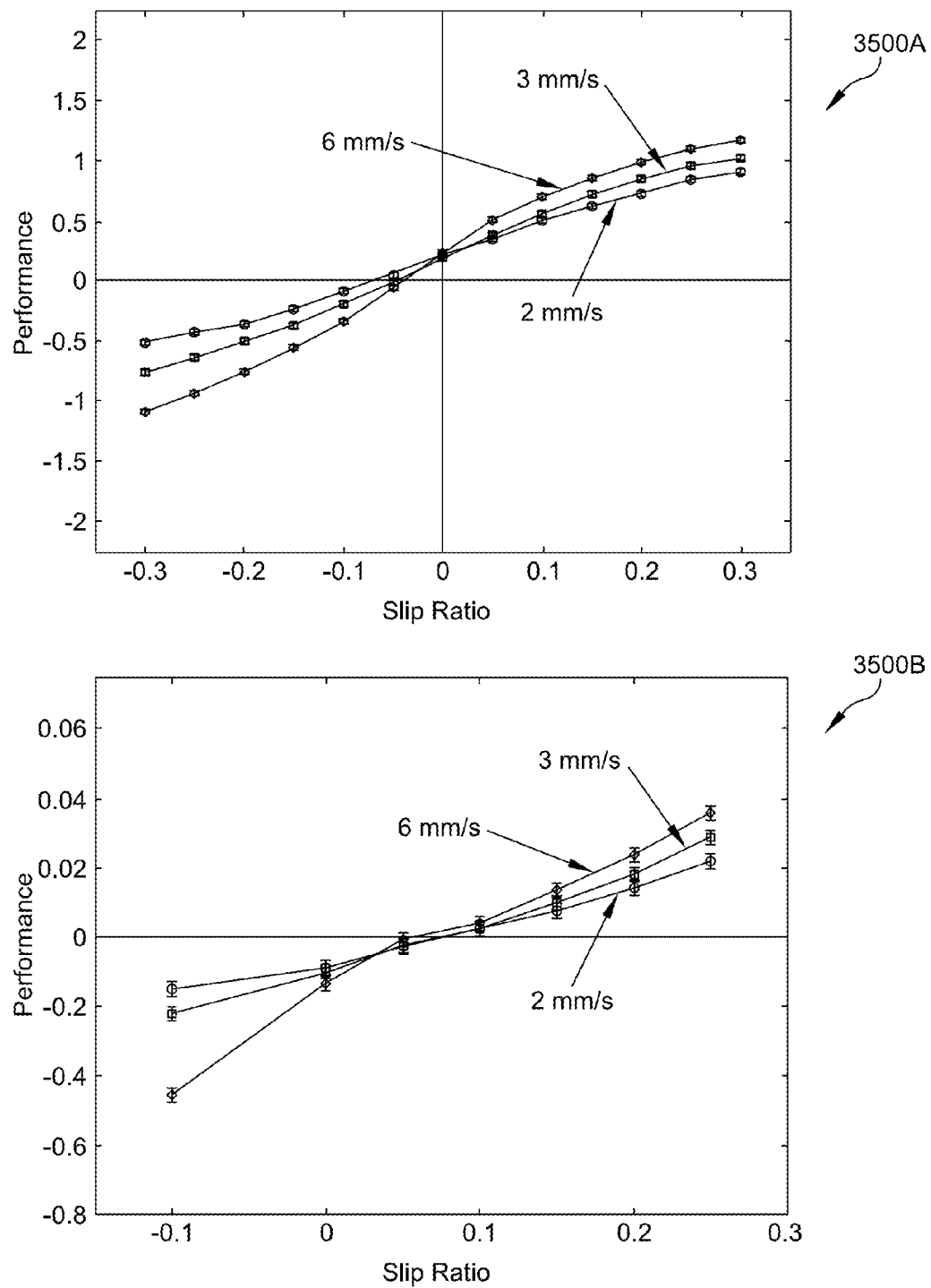
FIG. 35 illustrates experimental results showing the relationship between linear speed and tread performance for hydrated synthetic (top) and beef liver (bottom) tissue with data shown from the equally spaced diamond pillar micro-pattern with a 0.30 N normal force (top), and equally spaced circular pillar micro-pattern with a 0.20 N normal force (bottom)

It is possible to maintain a constant slip ratio by proportionally increasing or decreasing both the linear and rotational speeds. To study this effect, the linear and rotational speeds were proportionally varied at each induced slip ratio. For simplicity of the discussion, only translational speeds will be mentioned. Three translational speeds were studied (2 mm/s, 3 mm/s and 6 mm/s) based on expected in vivo robot travel velocities. The relationship between the linear speed and tread performance is shown in FIG. 35. For both the hydrated synthetic tissue 3500A (FIG. 35) and beef liver 3500B (FIG. 35), the performance is directly proportional to linear speed. This can be attributed to the viscoelastic properties of both the synthetic tissue and the beef liver. Since substrate stiffness is strain rate dependent, the substrates become stiffer as speed is increased, resulting in less energy loss and drag due to deformation. Although the data 3500A shown in FIG. 35, is from the diamond pillar micro-pattern with a 0.30 N normal force on hydrated synthetic tissue, and the data 3500B shown in FIG. 35 is from the circular pillar micro-pattern with a 0.20 N normal force on beef liver, similar trends were observed for all treads, normal forces, and dry synthetic tissue.

Figure 36:
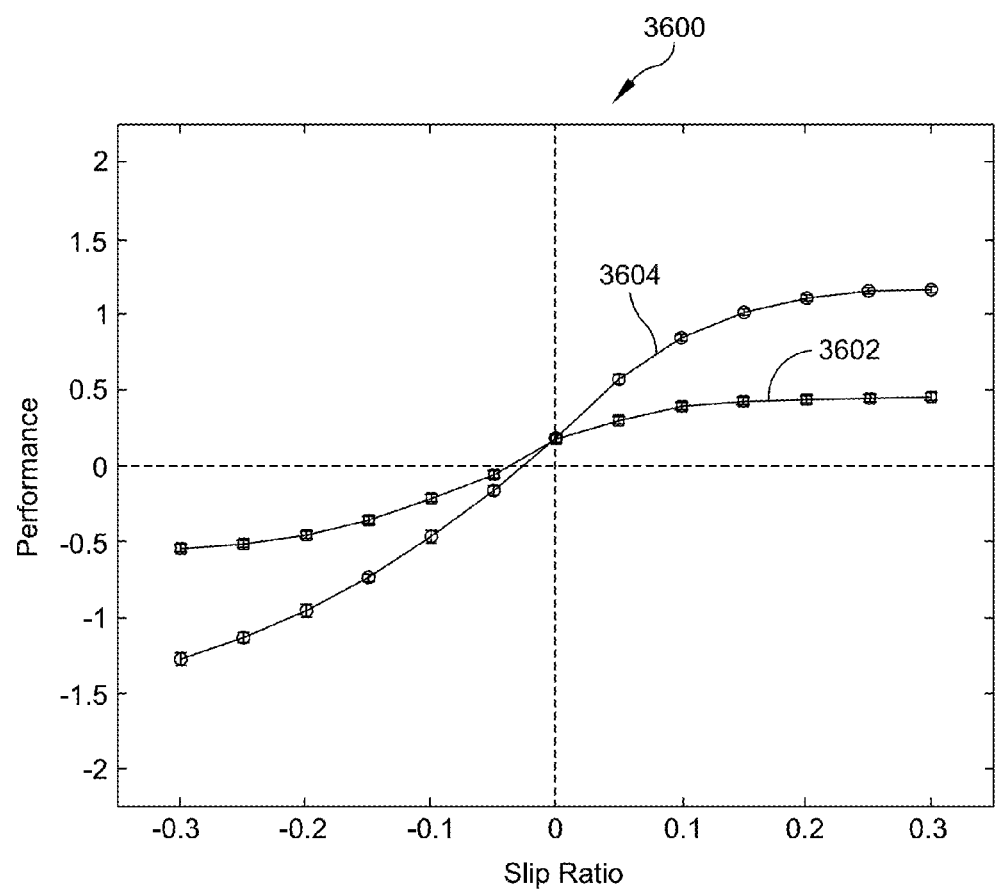
FIG. 36 illustrates experimental results showing the relationship between synthetic tissue hydration and tread performance with data shown from a smooth PDMS wheel with a 0.10 N normal force at a linear speed of 2 mm/s.

The relationship 3600 between synthetic tissue hydration 3602 (0.9% PBS bath) and performance is shown in FIG. 36. The performance decreases from dry synthetic tissues 3604 to hydrated synthetic tissue 3602 with the addition of hydration. This effect seems intuitive since the PBS acts as a lubricating layer, however both the PDMS and synthetic tissue are hydrophobic (water is repelled), so this effect might change with a change in hydrodynamic properties of the wheel, substrate, or both. Although the data shown in FIG. 36 is from a smooth PDMS wheel with a 0.10 N normal force at a linear speed of 2 millimeters/second, similar results were observed for all treads, normal forces, and speeds.

Figure 37:
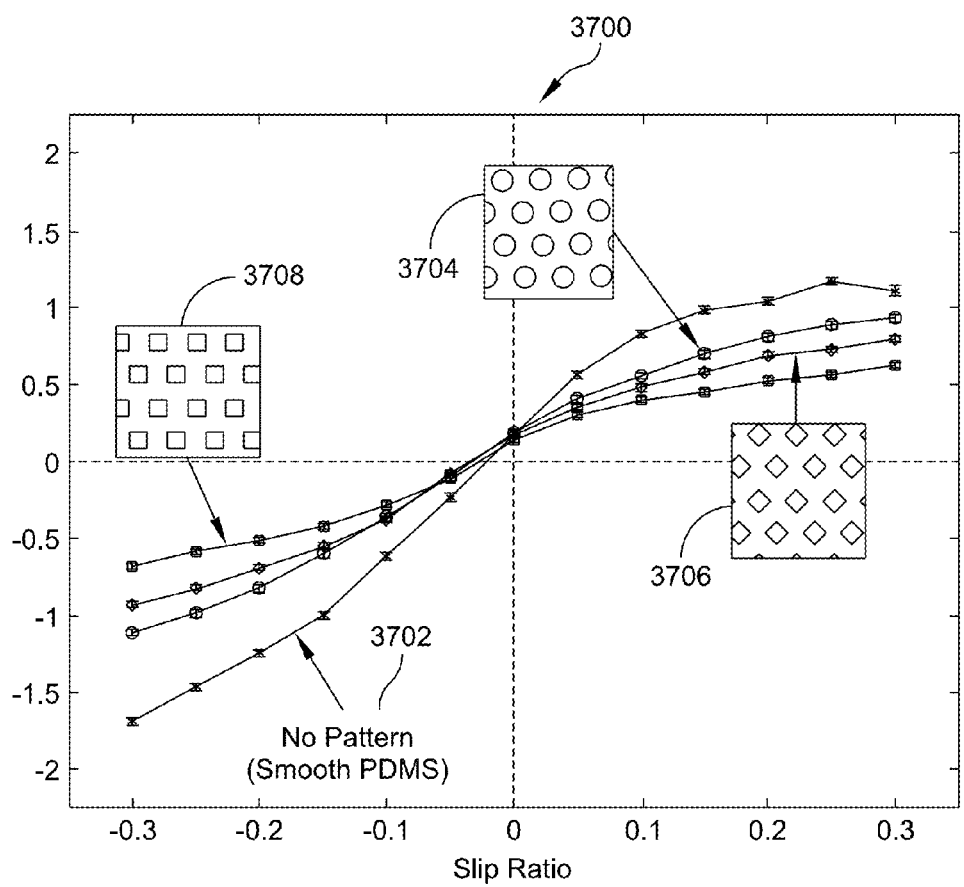
FIG. 37 illustrates experimental results showing the relationship between pillar geometry and tread performance on synthetic tissue. Data shown here is from a dry substrate with a 0.30 N normal force at a linear speed of 3 mm/s.
Figure 38:
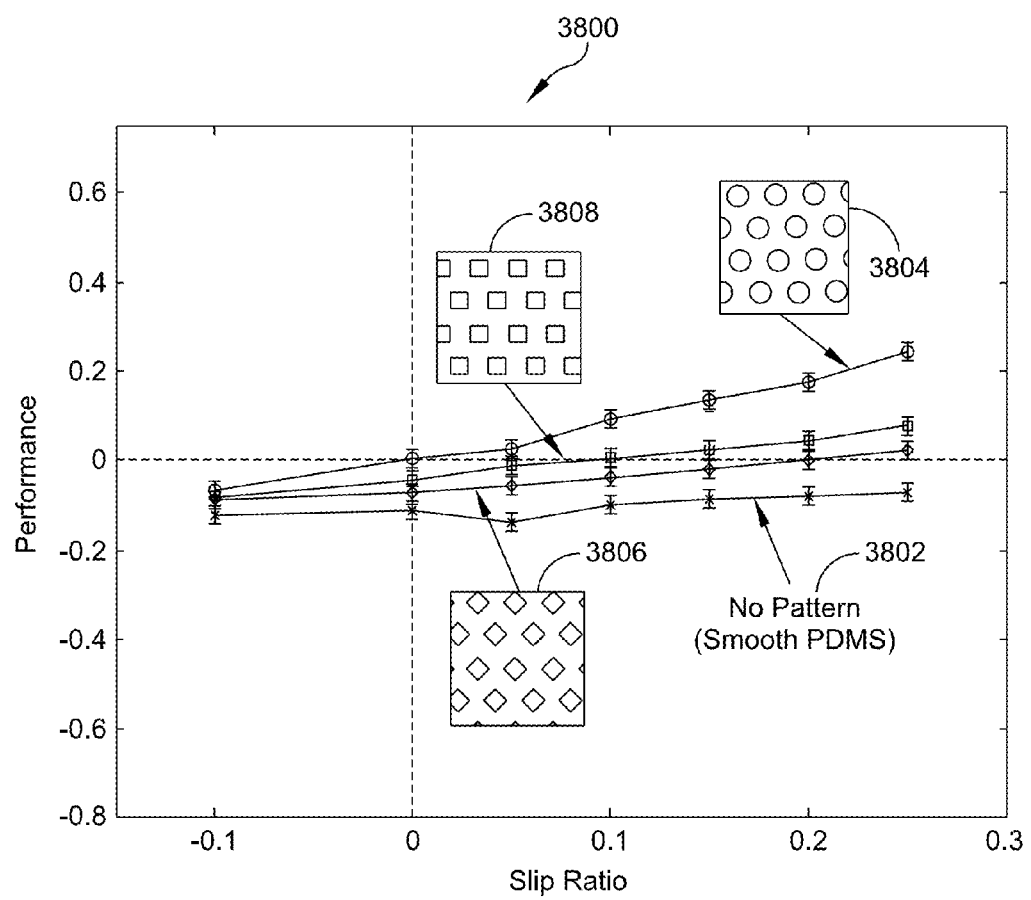
FIG. 38 illustrates experimental results showing the relationship between pillar geometry and tread performance on beef liver with data shown from a normal force of 0.30 N and a linear speed of 2 mm/s.

The relationship between pillar geometry and tread performance for synthetic tissue 3700 and beef liver 3800 are shown in FIGS. 37 and 38, respectively. The two relationships are very different. For synthetic tissue, the smooth PDMS tread 3702 outperformed all other treads for all normal forces and speeds. For beef liver this relationship was reversed; the smooth PDMS tread 3802 performed the worst for all normal forces and speeds. The tread performance for synthetic tissue may be first dependent on contact surface area, and second dependent on micro-pillar edge effects. The smooth tread has the largest contact surface area, while the micro-patterned surfaces have a lower contact surface area (only the tops of the pillars come into contact with the surface. Of the different pillar geometries, the circle 3704/3804 has the largest cross-sectional area, while the diamond 3706/3806 and square 3708/3808 have smaller (but equivalent to each other) cross-sectional areas. On synthetic tissue, circle 3704/3804 performs better than diamond performs better than square 3708/3808. Despite their equivalent cross-sectional areas, the diamond pattern might outperform the square pattern due to a mechanical advantage from the effect of the edge orientation.

From beef liver results, any one of the micro-patterns provides an increase in tread performance over a smooth tread. The circular pattern performs best, followed by the square, followed by the diamond. Again, it seems that among the micro-patterns, tread performance might be dependent on contact surface area. For the equivalent cross-sectional areas (square and diamond), the square pattern might have a mechanical advantage over the diamond due to edge effects on the tissue topography.

It is believed that no one has successfully modeled the contact mechanics between a micro-patterned surface and tissue. It's well known that tissue is viscoelastic in nature, and is inherently rough on a microscopic level. The micro-patterned surface most likely mechanically interacts on a microscopic level to enhance friction, however there are likely to be other contributing forces, such as van der Waals and capillary forces. The capillary forces would be a result of the liquid layer (mucous in a live animal or saline in a laboratory setting) between the tissue and micro-patterned surface. Other factors may include hydrophobicity variations of the tread and substrate as well as modeling of the micro-pattern/substrate interface.

Robotic Capsule Endoscope In Vivo Testing

Figure 32A:
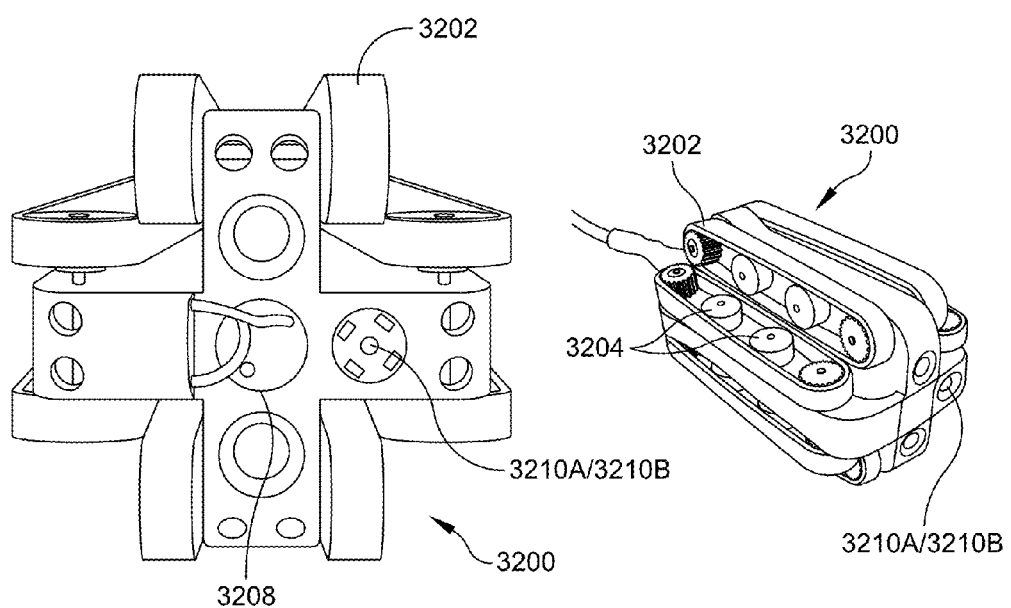
FIGS. 32a and 32b illustrate a robotic capsule endoscope (RCE) with micro-patterned PDMS treads, the RCE measures 29 mm in diameter, 46 mm in length, and weighs 29 grams, and the RCE features a camera and a light source.
Figure 32B:
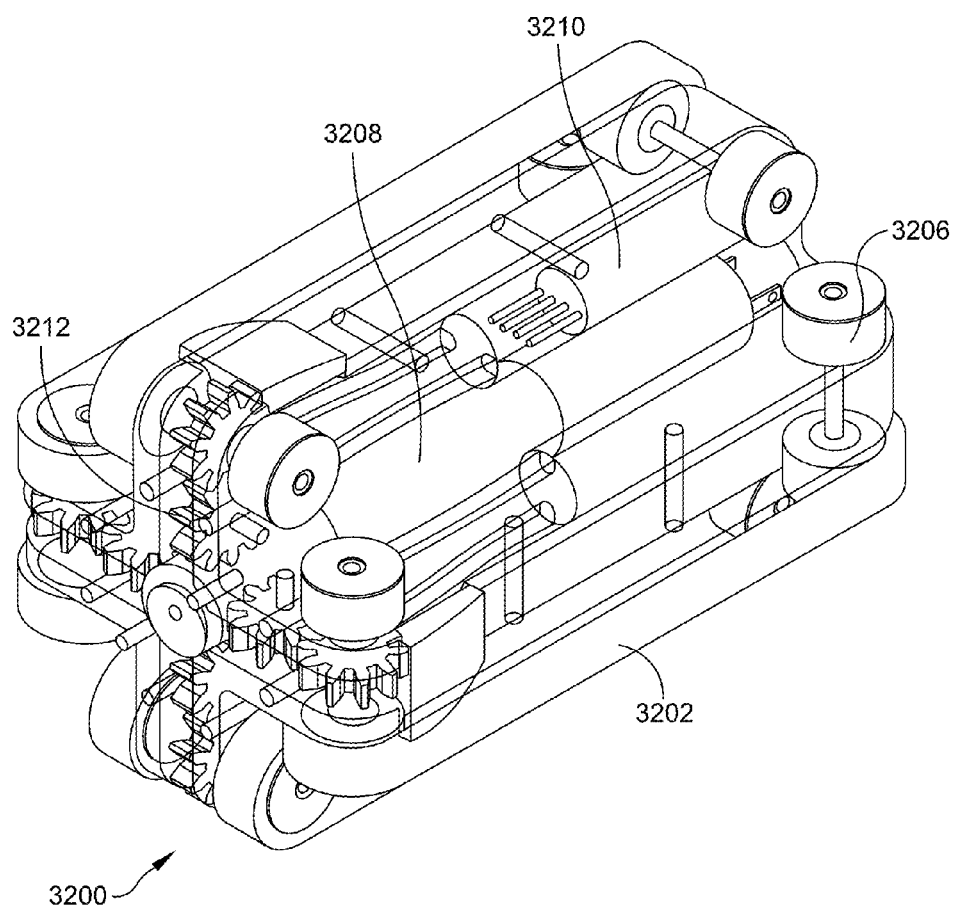

The best performing (on tissue) micro-patterned tread (circular pillars) was implemented onto an RCE prototype 3200 (FIG. 32). The prototype 3200 includes a plastic housing with a centrally located DC motor 3208 (0615 C 4.5 S, FAULHABER) with a 256:1 planetary gear-head (06/1 256:1, FAULHABER). The DC motor 3208 has a worm fixed to its shaft, which drives four concentrically symmetric perpendicular shafts. Each of the worm gears on these shafts mate with another shaft. The outermost shaft 3212 is fixed to timing pulleys 3206. The timing pulleys 3206 mate with the inside of the PDMS treads 3202. The RCE has two 3 mm treads 3202 on each of the four sides of the device (8 treads total) enabling forward and reverse motion. The RCE features a small camera 3210A (RS4018A-118, Bangu Technology Development Company Limited, Guangdong, China) equipped with 4 LEDs 3210B as a light source, and a tether 3910 for power and control.

The micro-patterned PDMS sheets 3202 (from micro-pattern PDMS fabrication) were cut into 3 mm wide strips for the RCE treads. Custom timing belts (3 mm wide) were also fabricated from PDMS, and the two were joined together using a combination of an oxygen plasma exposure (20 W for 25 s) and double-sided tape. This formed a looped tread with timing pulley on the inside of the loop, and micro-pattern on the outside of the loop.

Device mobility was tested in vivo using the large bowel of a live anesthetized porcine. An incision was made in the abdominal wall, and the cecum (a section of the large bowel) was resected. A small incision was made in the bowel, and the device was inserted. The device was activated and video was recorded from both the onboard camera and an external laparoscopic camera (22220130, Karl Storz, El Segundo, Calif., USA).

Figure 39:
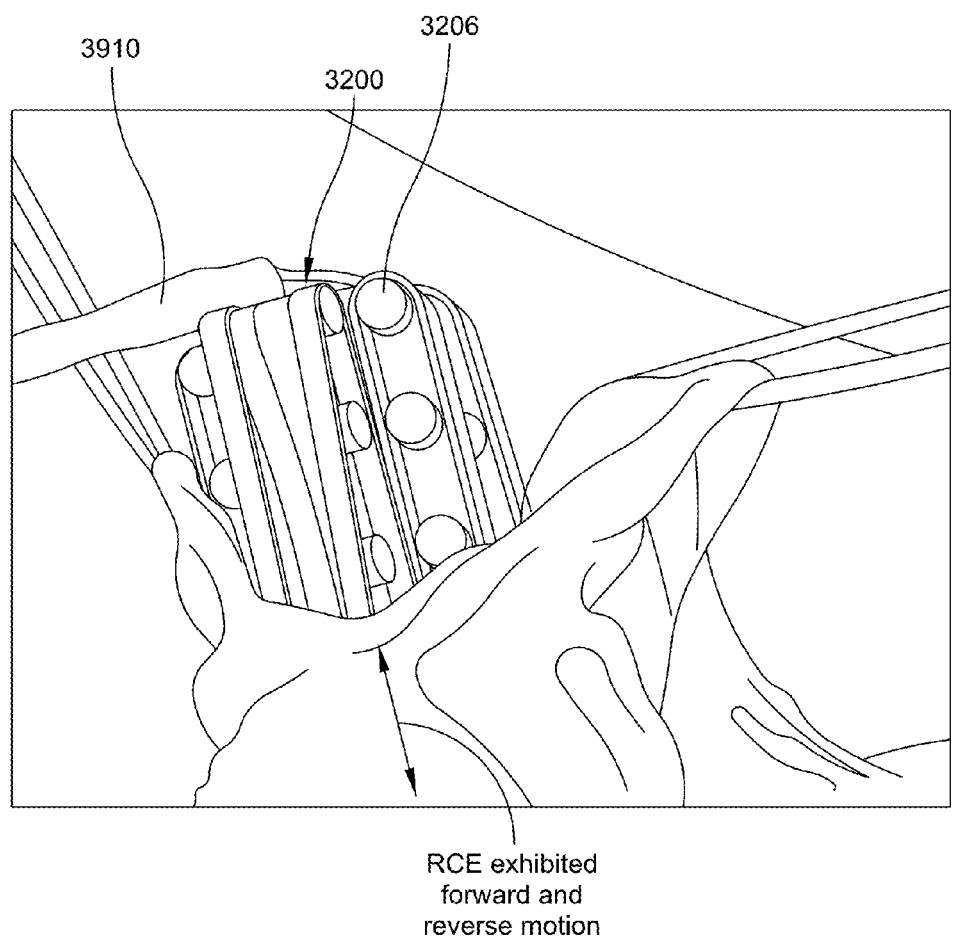
FIG. 39 illustrates the robotic capsule endoscope (RCE) prototype in the cecum (large bowel) of a porcine (pig) model (view from laparoscope) with the RCE exhibited both forward and reverse motion in the large intestine of a pig.

When placed in the cecum of the porcine the RCE 3202 was able to travel through the lumen upon activation of the drive system (FIG. 39). The RCE was able to travel in both forward and reverse motion. These results help demonstrate that a more advanced device, equipped with a real-time imaging system, sensors, and tools could be precisely controlled to move anywhere within the GI tract. Once at the surgical site of interest, the RCE could possibly provide therapy in the form of biopsy, tissue dissection, drug delivery, or the "tagging" of tissue for future surgical removal (e.g., colectomy for a cancerous section of colon). This RCE could ultimately be swallowed or deployed off of the end of an endoscope. This kind of device could also have the potential for natural orifice translumenal endoscopic surgery (NOTES), where the RCE enters through a natural orifice, travels through the GI tract, exits the GI tract, performs a surgical procedure elsewhere in the body (e.g., appendectomy), returns to the GI tract, and exits the body naturally.

Micro-patterned treads of varying geometry were experimentally evaluated on beef liver, and hydrated and dry synthetic tissue. Increasing speed (at constant slip ratio) increases tread performance, most likely due to the strain rate hardening response of the substrate materials. Hydrating the synthetic tissue causes a decrease in tread performance. Micro-patterning a PDMS surface provides decreased tread performance on hydrated and dry synthetic tissue, but increased performance on beef liver. The circular pillar micro-patterned tread (best performance on beef liver) was implemented into an RCE prototype and evaluated in vivo. The results indicate that mobility of an RCE is possible in the large intestine using micro-patterned PDMS treads.

Endoscopy is a current surgical method used to clinically investigate the lumen of the gastrointestinal (GI) tract. This surgical method involves a long, flexible scope termed endoscope, which enters the patient through a natural orifice. The endoscope has a camera and illumination source on the tip and often has the capability of taking small tissue biopsies. Although this tool has promoted the field of minimally invasive surgery and proven to be a successful and versatile tool, there are limitations to the device. The entire GI tract includes the esophagus, gastric cavity, and small and large bowels. The small bowel itself is about 7 m long. The major limitation to the endoscope is that it is not capable of viewing the entire small bowel, specifically the jejunum and ileum, the medial and distal sections of the small bowel respectively. Capsule endoscopy (CE) is a method for overcoming these limitations. Currently there are only two commercially available CE devices, the PillCam® SB (to view the small bowel) and the PillCam® ESO (to view the esophagus). (Given Imaging Website (2011, Apr. 6), Given Imaging Ltd., Duluth, Ga. Available: www.givenimaging.com.) These devices are pill sized capsules (11 mm×26 mm) which house a miniature video camera and light source and are swallowed by a patient. (Given Imaging Website (2011, Apr. 6), Given Imaging Ltd., Duluth, Ga. Available: www.givenimaging.com.) As the capsule passively moves through the GI tract, the camera within the capsule transmits images at a rate of 2 frames/s and can be immediately uploaded for the physician to view. (Given Imaging Website (2011, Apr. 6), Given Imaging Ltd., Duluth, Ga. Available: www.givenimaging.com.) Although these devices have made great strides in the pursuit of effective CE's, the devices present some limitations. The CE's are passive devices, so there is no control over the position of the device as it moves through the GI tract making it difficult to know exactly where, and at what orientation, the images are taken. Also, the rate at which the images are transmitted does not allow for doctors to have a continuous view of the GI tract as the devices pass through it. The major risk of CE devices is capsule retention. Most capsule retention cases are seen in patients with Crohn's disease and the retention rate is roughly 5%. (Cave D, Legnani P, de Franchis R, Lewis BS (2005) ICCE consensus for capsule retention. Surg Endosc 37:1065-1067; and Zhuan L, Rui G, Can X, Zhao-Shen L (2010) Indications and detection, completion, and retention rates of small-bowel capsule endoscopy: a systematic review. Gastrointest Endosc 71:280-286.)

The main focus of this research is to develop a robotic capsule endoscope (RCE) that is designed to provide continuous video feedback, and CE mobility and active locomotion through the large bowel and insufflated abdomen, demonstrating the feasibility of such a device in natural orifice translumenal endoscopic surgery (NOTES). For a NOTES procedure, the RCE would enter a natural orifice into the GI tract, exit the GI tract into the abdomen through an internal incision, perform a surgical task (i.e., liver biopsy, cholecystectomy, appendectomy, salpingectomy and oophorectomy) then exit the body through the GI tract. NOTES provides several advantages over traditional laparoscopy including the elimination of external incisions and the potential subsequent side effects such as pain, hernias, and external wound infections. Other benefits of NOTES include decreased adhesions, decreased need for anesthesia, and shorter hospital stays. Using micro-patterned treads for traction on the tissue, the position and orientation of the RCE can be controlled while maintaining visual capabilities. Due to previous laboratory success (Sliker L J, Wang X, Schoen J A, Rentschler M E (2010) Micropatterned Treads for In Vivo Robotic Mobility. ASME J Med Devices 4:041006-1-041006-8), polydimethylsiloxane (PDMS) micro-patterned treads are used as the mobility method for the RCE because they provide sufficient traction on the bowel tissue while minimizing tissue damage. The micro-pattern was biologically inspired by the hairs on the end of insect feet. Certain terrestrial animals have evolved to develop micro-hairs on the pads of their feet to enhance friction for locomotion on various substrates. (Beutel R G, Gorb S N (2001) Ultrastructure of attachment specializations of hexapods (Anthropoda): evolutionary patterns inferred from a revised ordinal phylogeny. J Zool Syst Evol Research 39:177-207; and Beutel R G, Gorb S N (2006) A revised interpretation of the Evolution of Attachment Structures in Hexapoda with Special Emphasis on Mantophasmatodea. Anthropod Systematics & Phylogeny 64:3-25.) The pad is able to match the surface structure of the substrate, maximizing the contact surface area, and thus increasing the frictional and adhesive properties of the feet. (Gorb S (2000) Biological microtribology: anisotropy in frictional forces of orthopteran attachment pads reflect the ultrastructure of a highly deformable material. Proc R Soc London, Ser B 267:1239-1244; Gorb S N (2001) Attachment Devices of Insect Cuticle, Springer, N.Y.; and Persson B N J, Gorb S (2003) The effect of surface roughness on the adhesion of elastic plates with application of biological systems. J Chem Phys 119:11437-11444.) Other groups have attempted to enhance friction within the large bowel using micro-patterned PDMS (Karagozler M, Cheung E, Kwon J, Sitti M (2006) Miniature Endoscopic Capsule Robot using Biomimetic Micro-Patterned Adhesives. Biomedical Robotics and Biomechatronics 105-111; Cheung E, Karagozler M E, Park S, Kim B, Sitti M (2005) A New Endoscopic Microcapsule Robot using Beetle Inspired Microfibrillar Adhesives. Proceedings of the 2005 IEEE/ASME International Conference on Advanced Intelligent Mechatronics 551-557; Glass P, Cheung E, Sitti M (2008) A Legged Anchoring Mechanism for Capsule Endoscopes Using Micropatterned Adhesives. IEEE Transactions on Biomedical Engineering 55:2759-2767; and Buselli E, Pensabene V, Castraturo P, Valdastri P, Menciassi A, Dario P (2010) Evaluation of friction enhancement through soft polymer micro-patterns in active capsule endoscopy. Meas Sci Technol 21:1-7) and using other friction enhancement techniques. (Valdastri P, Webster R, Quaglia C, Quirini M, Menciassi A, Dario P (2009) A New Mechanism for Mesoscale Legged Locomotion in Compliant Tubular Environments. IEEE Transactions on Robotics 25:1047-1057.)

Robotic Capsule Endoscope Design and Fabrication

The following criteria were developed when designing the RCE: 1) the ability to travel within a collapsed lumen, 2) the ability to traverse a planar tissue surface, 3) capability of both forward and reverse motion, 3) sized to fit within the large intestine of a human (6 centimeter diameter), and 4) provide visual feedback to a monitor located external to the patient.

The RCE design can be divided into four main parts, the 1) housing, 2) drivetrain, 3) micro-patterned treads, and 4) vision and illumination system.

RCE Housing

Based on previous success with robotic mobility using micro-patterned PDMS treads, a tissue-robot interface was designed for the RCE to address the first two design criteria. In order to gain mobility within a collapsed lumen, the housing was designed to include tank-like treads on all sides of the robot. The housing was designed to have a rectangular prismatic geometry so as to produce a robot with four relatively large flat sides for traversing planar tissue, while creating tread surface area for traveling within a lumen. In order to maximize traction both in a lumen and on planar tissue, each side of the RCE was designed to have two treads, creating a large tread to housing surface area ratio. For simplicity of the design, the RCE needed to be capable of forward and reverse motion, but not left, right, up, or down. In other words, all treads could be driven in the same direction at any given time, minimizing the number of required actuators, and thus reducing the size of the RCE. The RCE presented here could be reconfigured to enable turning capabilities in the abdomen by configuring two RCEs side-by-side in a tank configuration. For travel within a cylindrical lumen (the RCE's primary goal), the design relies upon the geometry of the robot and its environment for steering. As long as the robot is longer than it is wide and there is sufficient radial pressure from the lumen, the lumen will direct the robot in the axial direction, preventing it from turning around or getting stuck within the lumen. The housing (FIG. 40) was designed to hold the drivetrain, 8 micro-patterned treads (two per side), a vision system, and an illumination system. The housing was prototyped (Protogenic, Westminister, Colo., USA) using Protoclear 10120 (DSM Somos, Elgin, Ill., USA).

RCE Drivetrain

The drivetrain includes a direct current (DC) motor (FAULHABER, Croglio, Switzerland) with a 256:1 planetary gearhead reduction (FAULHABER, Croglio, Switzerland), a gear train, and timing pulleys. The DC motor is centrally located within the housing. A 0.5 modulus worm (GW0.5-01-14, Gizmoszone, Hong Kong, China) was press-fit on the shaft of the motor. Four (one per side) 0.5 modulus worm gears (GWG0.5-10-19, Gizmoszone, Hong Kong, China) were mounted to a bottom axle and driven by the worm. The ratio between the worm and worm gears provides an additional 10:1 reduction. Two 3 mm wide timing pulleys, made from timing pulley stock (A 6A15-010MXL02, Stock Drive Products/Sterling Instruments, New Hyde Park, N.Y., USA), are also fastened to each top axle (one on each end). Therefore, as the worm gears are driven, power is transferred to the top axles and thus the timing pulleys.

Micro-Patterned PDMS Treads

Figure 40:
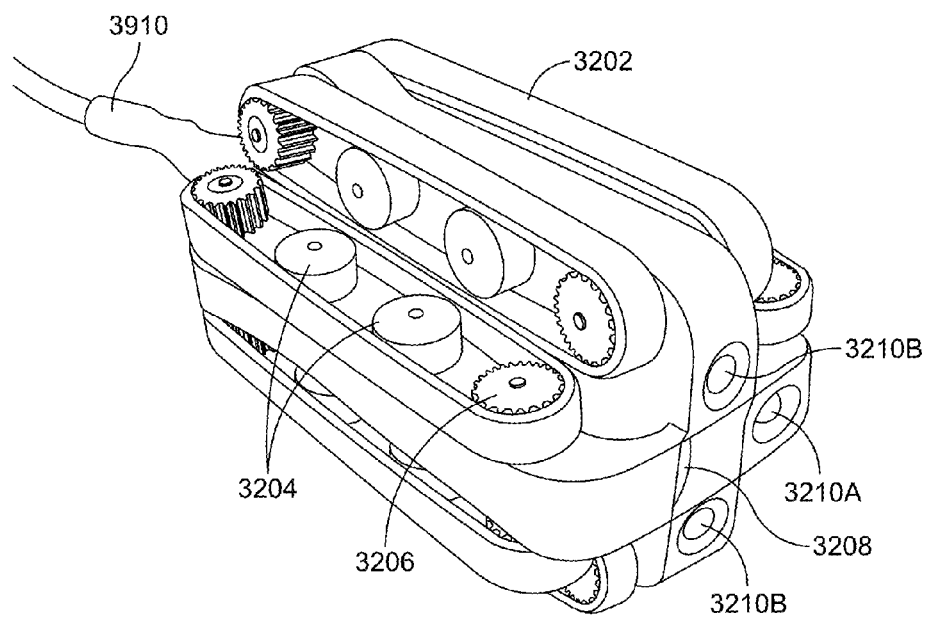
FIG. 40 illustrates a fully assembled robotic capsule endoscope on a benchtop.

The purpose of the drivetrain is to transfer power from the DC motor 3208 to the timing pulleys 3206 on the end of each top axle. The timing pulleys 3206 then drive each micro-patterned tread 3202. Each PDMS tread 3202 had custom timing belt teeth 4602 (see FIGS. 46*a* and 46*b*) on the inside of the belt to mate with the driving timing pulley 3206. The outside of each PDMS tread 3202 features a micro-pattern includes 140 µm diameter, 70 µm high circular pillars. The pillars may be equally spaced with a center-to-center distance of 245 µm. In addition to the timing pulleys 3606, two Teflon rollers 3204 are added to each tread 3202 for support (FIG. 40). In order to prevent the treads 3202 from slipping off the pulleys 3606, washers, slightly larger than the pitch diameter of the pulleys 3206, may be adhered to the outer faces of the pulleys 3206 using epoxy. The overall dimensions of the RCE 3200 for this embodiment are 29 millimeters wide, 29 millimeters tall, and 46 millimeters long. The mass of the RCE for this embodiment is 29 grams. The RCE travels at a maximum speed of 3 millimeters/second.

Vision and Illumination Systems

Figure 41:
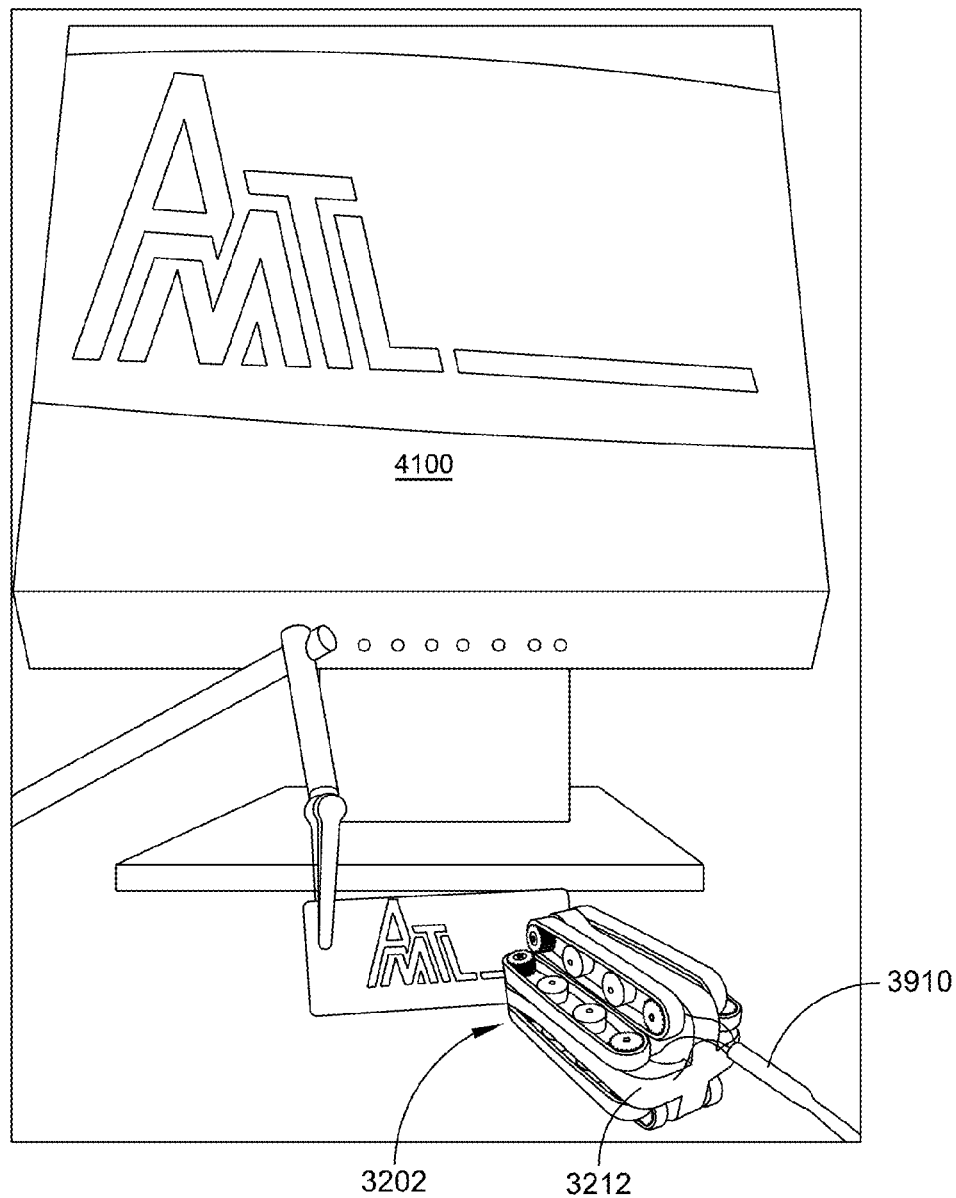
FIG. 41 illustrates a robotic capsule endoscope (RCE) with vision and illumination system.

The rear of the RCE housed the gear train for power transfer from the actuator, while the forward part of the RCE housed the vision and illumination system, as illustrated in FIG. 40. Three symmetric holes may be created in the housing for the imaging and illumination systems. The RCE design integrateds two different imaging techniques, visible light and infrared (IR) light. IR technology has shown to be useful for distinguishing healthy and cancerous tissue. (Ntziachristos V, Chance B (2000) Breast imaging technology: probing physiology and molecular function using optical imaging—applications to breast cancer. Breast Cancer Res 3:41-46.) IR rays emitted at the near infrared (NIR) range are ideal for imaging large organs. (Ntziachristos V, Chance B (2000) Breast imaging technology: probing physiology and molecular function using optical imaging—applications to breast cancer. Breast Cancer Res 3:41-46.) The tissues of large organs exhibit low absorption and allows light at a safe power to penetrate the tissue. (Ntziachristos V, Chance B (2000) Breast imaging technology: probing physiology and molecular function using optical imaging—applications to breast cancer. Breast Cancer Res 3:41-46.) When the emitter produces wavelengths in the NIR range, they can be reflected back to a camera, producing a thermal image. A 4 mm wide analog camera with 4 integrated LEDs (RS4018A-118, Bangu Technology Development Company Limited, Guangdong, China) was placed in one of the holes. The two remaining holes each housed a 3 mm infrared emitting diode (LIR204X, Jameco Electronics, Belmont, Calif., USA). A user-controlled system may be implemented to select the type of illumination and the intensity of the light. All of the wires for the LEDs, camera, and motor may be routed out of the back (near the gear train) of the RCE and tethered to an external control box. The box featured controls for light selection and intensity, motor activation and direction, and camera activation. The image from the camera may be displayed on a monitor 4100, external to the patient, for real-time viewing (FIG. 41).

The camera is capable of detecting both visible and IR light. When the camera is placed in an environment with no visible light (i.e., an insufflated abdomen), and the IR illumination is activated, a grey scale thermal image is produced.

Benchtop Performance Evaluation

Upon fabrication, the RCE was evaluated in a controlled laboratory setting to benchmark the performance of the device prior to in vivo testing. Both the mobility and the imaging/illumination systems were tested.

To test the mobility system, the device was driven across multiple flat surfaces (laminate, paper, latex, and synthetic tissue) to evaluate mobility. Next, the device was placed in between two layers of synthetic tissue (Simulab Corporation, Seattle, Wash., USA), with a 500 g mass on the top, to benchmark the durability and required torque of the RCE, to move through a collapsed lumen.

To test the vision/illumination system, the RCE was placed in an isolated (from light) box. A monitor was placed outside of the box and the camera was activated with 1) no light source, 2) visible light from the LEDs, 3) IR light, and 4) visible and IR light. Various objects (color and grey scale) were placed in the field of view at various distances from the RCE to benchmark the quality of the imaging system with the various illumination sources.

Porcine Study

The benchtop tests provided a benchmark performance level for the RCE under various conditions. The purpose of the porcine study was to determine the level of performance relative to the benchmark performance level in various in vivo environments. The two primary test conditions of interest were mobility on planar tissue in an insufflated cavity, and mobility within a collapsed lumen. To test mobility of the RCE on planar tissue, the device was placed within an insufflated abdomen. To test for mobility within a lumen, the RCE was placed in the cecum (section of the large intestine).

During in vivo testing, a 5 cm long incision was made in the umbilicus of the pig and then the RCE was inserted through the incision with approximately 30 cm of wire to reduce drag on the RCE. After insertion, the incision was sutured around the wire to produce an airtight seal. Two 12 mm trocar ports were inserted in the abdominal wall using a standard technique. One trocar was used for a laparoscopic camera (model 22220130, Karl Storz, El Segundo, Calif., USA) and $CO_2$ insufflation, while the other was used as a tool port (to manipulate the RCE). Upon abdominal insufflation, the RCE was positioned on bowel and mesentery using laparoscopic tools. Then, the RCE was activated to evaluate mobility on bowel and mesentery. Next, the RCE was repositioned onto the liver/abdominal wall using laparoscopic tools. Again, the RCE was activated to evaluate mobility on liver and abdominal wall. Throughout the test, video from the laparoscopic camera was recorded. The imaging system from the RCE was also recorded throughout the entire test to evaluate imaging system performance.

After mobility testing in the insufflated abdomen, the imaging system was tested. The light source from the laparoscope was deactivated. The visible light source on the RCE was activated, and then deactivated. Next, the IR light source on the RCE was activated and then deactivated. Finally, both the visible and IR light sources on the RCE were simultaneously activated and then deactivated. Throughout the test, video from the RCE camera was recorded for evaluation.

In order to test for mobility within a lumen, the RCE was placed in the cecum of the porcine model. Due to size restrictions, the test could not be performed in the small intestine, though future versions of this device will likely be tested in the small bowel. The test was performed as follows. The 5 cm long incision was reopened and the RCE was removed from the abdomen. A section of the cecum was pulled out of the abdomen and placed on the outside of the porcine. A 3 cm incision was made in the cecum and then the cecum was cleaned out using suction. The incision was held open using forceps while the RCE was inserted partially into the cecum. The RCE was activated to evaluate the performance of the device in the lumen.

Device Performance

The purpose of the benchtop tests was to set a benchmark performance level for all RCE tasks, so that performance during the in vivo study could be compared to a control. During benchtop mobility testing, the device was able to successfully traverse each of the terrain types (laminate, paper, latex and synthetic tissue). Also, the device was able to travel the maximum possible distance (length of the synthetic tissue sample, 170 mm) between two layers of synthetic tissue with a 500 g mass on the top of it. During the benchtop imaging system testing, an adequate picture was displayed on the monitor for each of the lighting scenarios. Common objects (i.e., cord, pencil, pen, calculator, battery, coin) placed within the field of view could easily be identified on the monitor under all of the lighting scenarios.

Porcine Study Results

Figure 42:
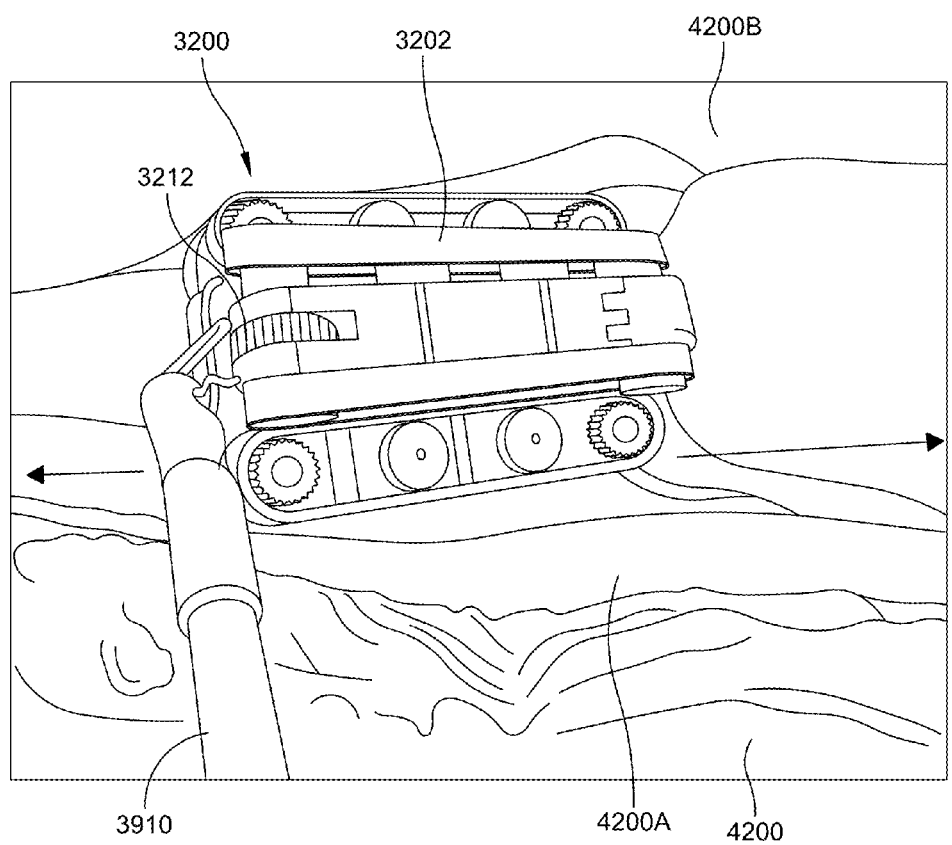
FIG. 42 illustrates a robotic capsule endoscope (RCE) inside the insufflated abdomen of a live anesthetized porcine on liver (view from laparoscope)

During the first phase of the porcine study, the RCE 3200 was placed in the insufflated abdomen of the porcine. First the RCE 3200 was placed on a combination of bowel and mesentery. When the motor was activated, the RCE 3200 moved forward approximately 5 cm with minimal slipping. The RCE 3200 was positioned at an angle such that two of the sides (i.e., four treads) were in contact with the tissue. After 5 cm of travel, the direction of the motor was switched, and the RCE 3200 travelled backwards 5 cm to the starting position. Then, the RCE 3200 was moved to the liver using laparoscopic tools. The RCE 3200 was positioned so that three sides of the RCE 3200 were in contact with tissue 4200 (FIG. 42). Two of the sides were in contact with liver 4200A, while one of the sides of in contact with abdominal wall 4200B. Again, when the RCE was activated, it travelled forward approximately 5 cm (FIG. 42, dashed line) with no visible slipping. When the motor was reversed, the RCE 3200 travelled back 5 cm to the original location.

Figure 43:
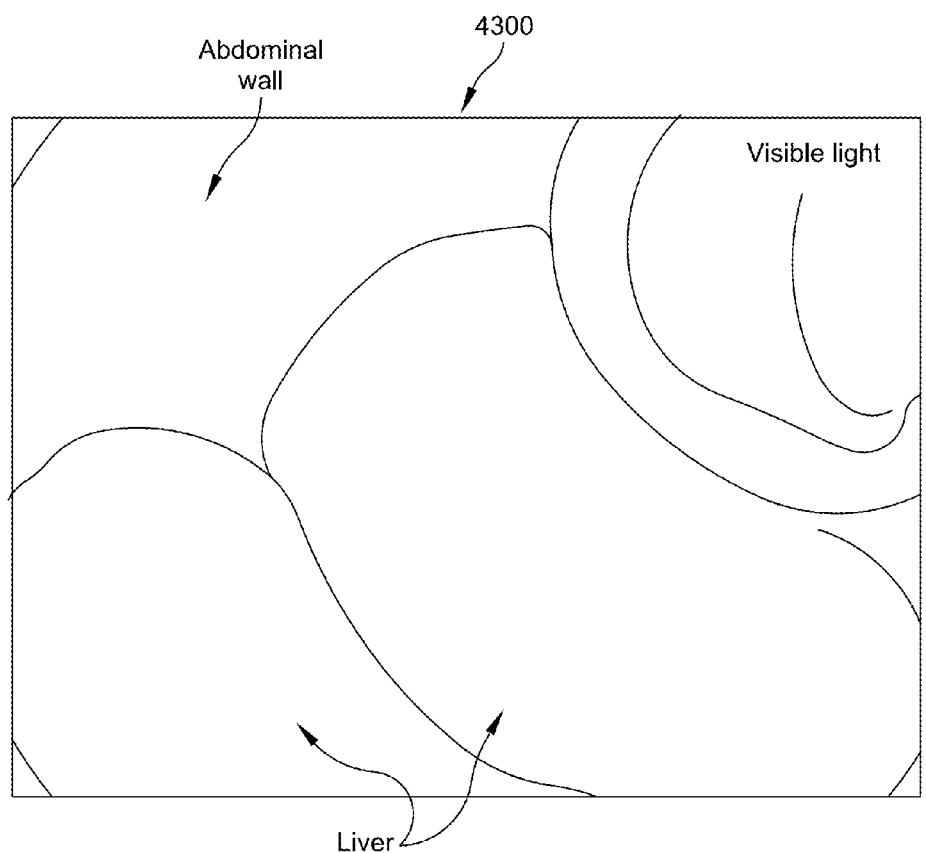
FIG. 43 illustrates a view from the robotic capsule endoscope (RCE) imaging system inside the insufflated abdomen using a visible light source.
Figure 44:
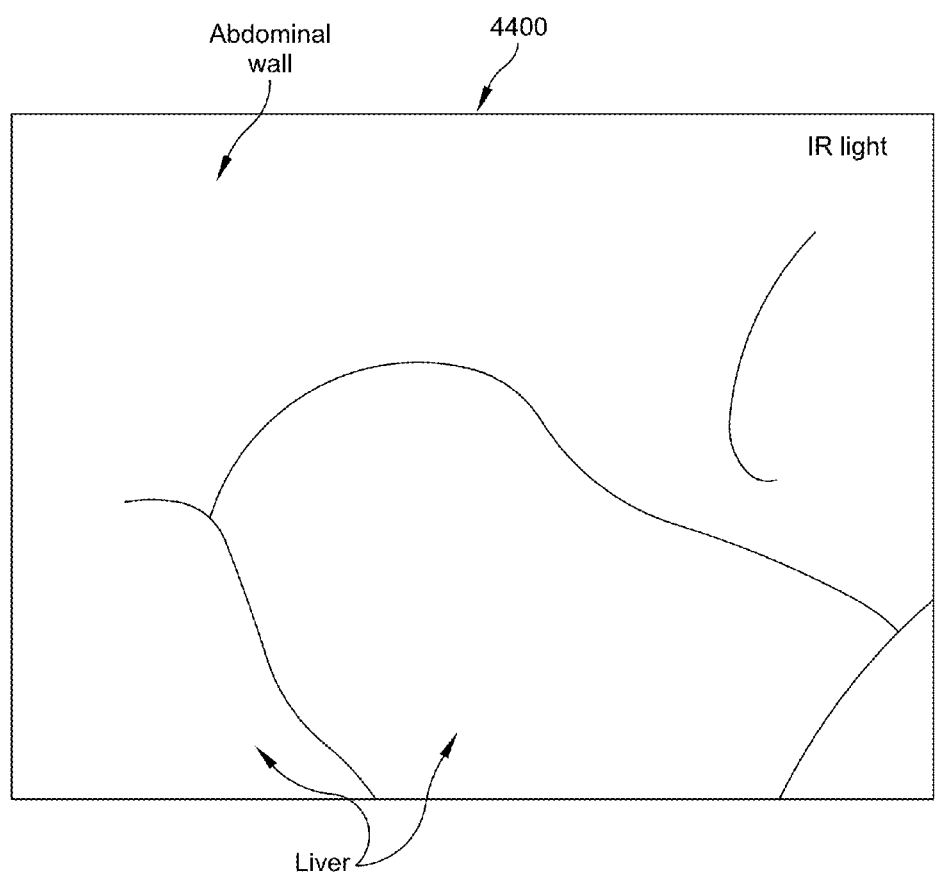
FIG. 44 illustrates a view from the robotic capsule endoscope (RCE) imaging system inside the insufflated abdomen using an IR light source.

Next, the imaging system was tested. The RCE 3200 was positioned so that several organs of varying color and density were in the field of view. The image 4300 from the camera with visible light only is shown in FIG. 43. The image 4300 was adequate enough to identify the organs within the field of view. The image 4400 from the camera with IR light only is shown in FIG. 44. The IR image 4400 provides a grey scale thermal view of the organs. Although it was hard to identify the different organs, the IR light does provide a high contrast image that could be useful in diagnosing diseased or unhealthy tissue. FIGS. 43 and 44 are taken from the same RCE orientation, so the field of view is nearly identical. In FIG. 44 (infrared light), there is a large white spot in the bottom center of the frame. This might initially be mistaken as contrast from the tissue, but it is, in fact, a focused reflection from the infrared diodes.

Figure 45:
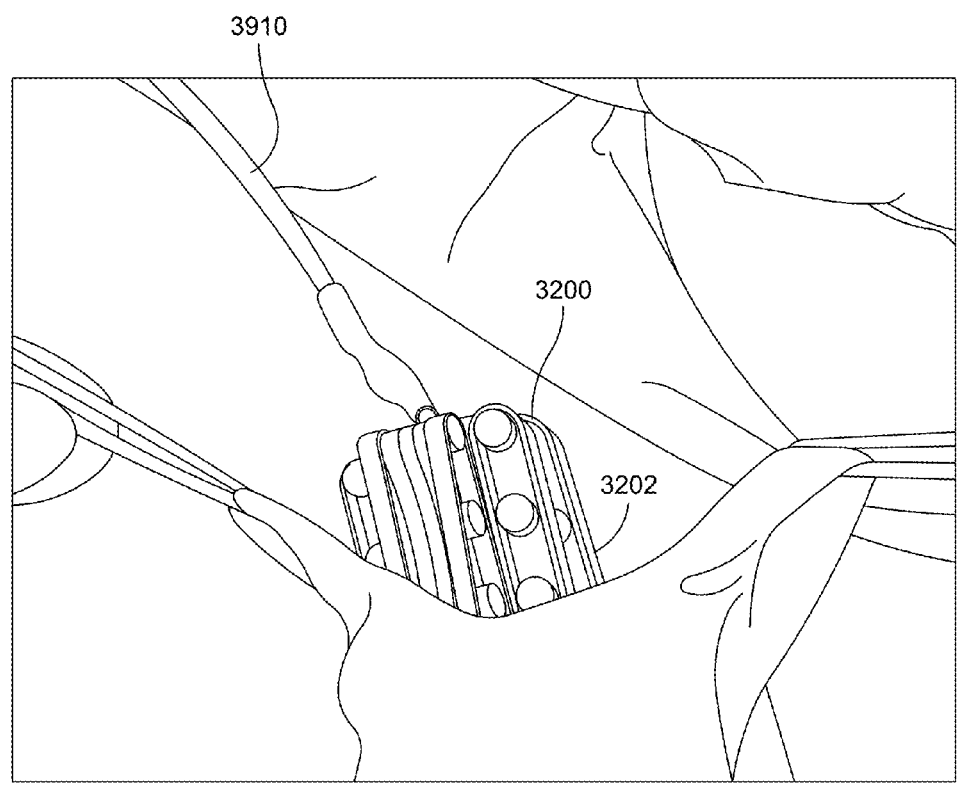
FIG. 45 illustrates robotic capsule endoscope (RCE) inside the cecum of a live anesthetized porcine.

With reference to FIG. 45, the final phase of the porcine study was the demonstration of mobility within a collapsed lumen. Due to size restrictions, the device was placed inside the cecum of the large bowel and not the small bowel. An incision was made in the cecum, and the device was placed about halfway into the incision. When the device was activated, it traveled approximately 4 centimeters into the cecum. When the direction of the motor was switched, the device traveled approximately 5 cm back out of the cecum, past the starting position. During reverse operation, the device was working against gravity and with the weight of the tether. This test was repeated three times with similar results. During the travel through the cecum, minimal slippage was observed. While the device was in the cecum, visual feedback was impaired due to the close proximity of the tissue to the camera lens.

The results of this and previous research (Sliker L J, Wang X, Schoen J A, Rentschler M E (2010) Micropatterned Treads for In Vivo Robotic Mobility. ASME J Med Devices 4:041006-1-041006-8) show that in vivo mobility is possible in both the insufflated abdominal cavity and a collapsed lumen using micropatterned treads in a robotic capsule endoscope configuration. These results illustrate that the area of NOTES can be advanced with future versions of the RCE. A mobile RCE that could enter the GI tract non-invasively, travel through the GI tract to the abdomen, exit the GI tract, travel through a collapsed (or possibly insufflated abdomen), perform a surgical task (i.e., cholecystectomy, appendectomy), return to the GI tract, then exit the body non-invasively would be a large advancement in the field of minimally invasive surgery (MIS). Additionally, the advantages of a mobile RCE just in the GI tract are numerous. With an active, cost effective, compact RCE, the device could provide inexpensive non-invasive diagnostic, exploratory, surgical, drug and other therapies at hard-to-reach locations within the small bowel.

A prototype RCE was designed and fabricated. Main features of the RCE includes micro-patterned PDMS treads as a mobility method, forward and reverse locomotion, and an onboard analog imaging system with both visible and IR light sources. The RCE was tested extensively in a controlled laboratory setting as well as in a live anesthetized porcine surgery. The RCE was fully functional on the benchtop, and performed equally as well in vivo. The RCE was able to traverse several planar tissue surfaces (i.e., bowel, mesentery, abdominal wall and liver) in an insufflated abdominal cavity as well as travel in and out of a lumen (i.e., the cecum). The imaging system provided an adequate visual feedback in the insufflated abdomen with both visible and IR light sources, but failed to provide an adequate image in the cecum, due to close proximity between the tissue and imager lens.

Desirable dimensions for an RCE are be approximately 12 millimeters in diameter and 25 mm in length. Tools may be added to the RCE for surgical tasks such as tissue manipulation, biopsy, cauterization, ablation, and drug delivery. The analog imaging system may be replaced with an equivalently sized high definition digital system. Eventually, the RCE will need to be untethered. To do this, the device will be wirelessly controlled and have an onboard power supply.

Tread Fabrication

Fabrication of micro-patterned treads for the robotic capsule endoscope (RCE) has progressed through multiple revisions. Each revision has either improved the functionality of the tread by increasing flexibility or reducing thickness, and/or improved the ease of fabrication. Each tread includes two major parts: the micro-patterned polydimethylsiloxane (PDMS) treads and a driving mechanism. The micro-patterned PDMS is on the outside surface of the tread, which interfaces with the tissue, while the driving mechanism is on the inside surface of the tread, and interfaces with the robot's driving mechanism (e.g., a timing pulley or roller). PDMS is inherently hydrophobic which makes it hard to bond to itself or other materials. Thus, it is a challenge to adhere the micro-patterned PDMS to the driving mechanism. Each tread is formed in the shape of a loop. Since the micro-patterned PDMS treads are fabricated in sheets, it is a challenge to transform the sheets into a loop.

Figure 46A:
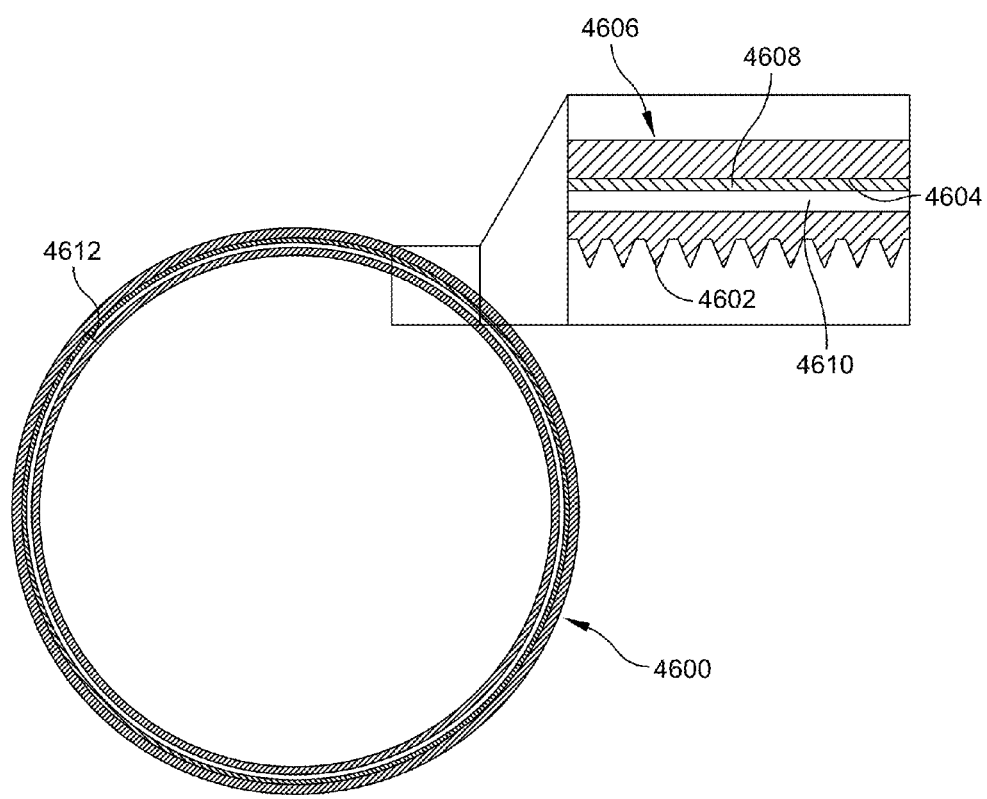
FIGS. 46a-46c illustrate titanium coated treads (a.), custom PDMS timing belt treads (b.), and friction PDMS treads (c.)

FIG. 46*a* illustrates an embodiment of a titanium coated timing belt with PDMS treads 4600. This first iteration of the tread fabrication was for RCE version 1 (RCE v1), which employed a timing belt/timing pulley drive system. In an attempt to increase the adhesion properties of the PDMS, the non-patterned side 4604 of the PDMS 4606 was coated with 100 nm of titanium (Ti) 4608 using a standard thermal deposition procedure. Double-sided tape 4610 (3M, 3M415) was applied to the outside surface of polyurethane timing belts 4602 (SDP/SI, A 6B18M094030). The micro-patterned PDMS 4606 was trimmed to the correct size, and the Ti coated side 4608 was pressed onto the tape 4610 (FIG. 46*a*). This resulted in a two-layer tread 4600, with a polyurethane timing belt 4602 as a driving mechanism and micro-patterned PDMS 4606 outer surface. Eight of these treads were fabricated for RCE v1. Each tread had a radius of 15 mm, a width of 3 mm and a thickness of 1.5 mm. The main problems associated with this tread were high stiffness, large thickness and seam separation. A tread seam 4612 was bonded to close the loop.

Figure 46B:
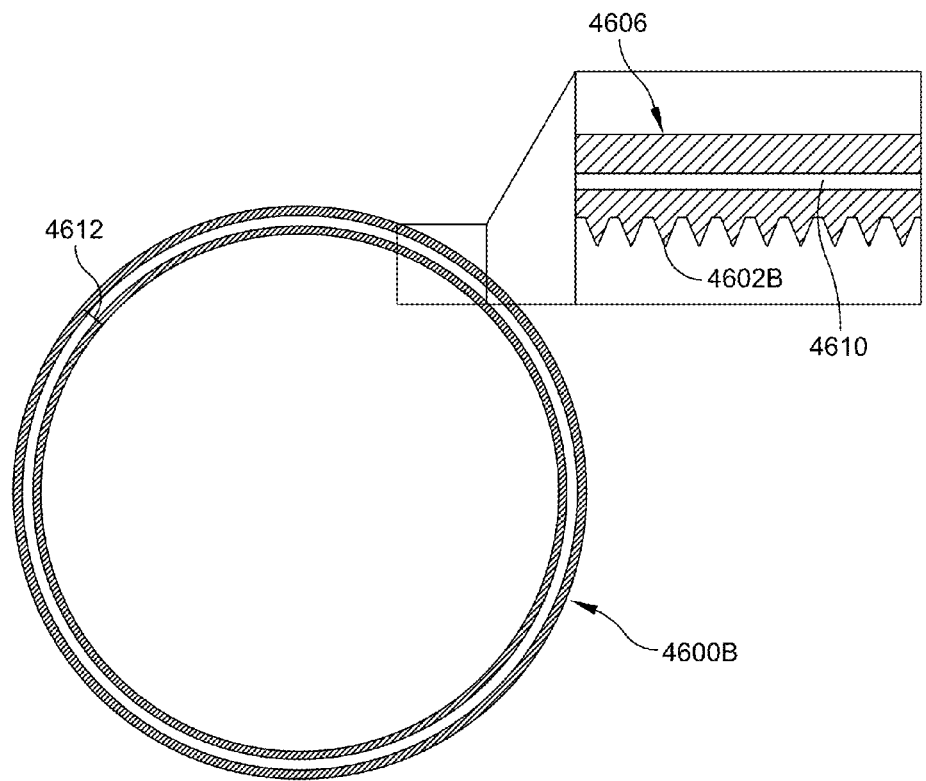

FIG. 46*b* illustrates a custom PDMS timing belt 4602B with PDMS treads. This second iteration of the tread fabrication was for RCE version 2 (RCE v2), which also employed a timing belt/timing pulley drive system. To reduce the stiffness of the treads, the polyurethane timing belts were replaced with custom PDMS timing belts 4602B. Also, to reduce tread seam separation, a new fabrication procedure was employed. A mold for the PDMS timing belts 4602B was fabricated using polyurethane timing belts (SDP/SI, A 6B18M094030) and an aluminum mold. Trenches (3 mm wide, 95 mm long, and 1.5 mm deep) were formed in an aluminum plate. Polyurethane timing belts 4602B were cut, stretched out, and glued to the bottom of the trenches (teeth side up). Liquid PDMS was poured into the mold and cured. The PDMS was polymerized by a heat curing process (100° C. for 1 hr). The polymerized PDMS was peeled out of the mold, creating strips of PDMS with one smooth side and one side containing timing belt teeth. The micro-patterned PDMS strips and the timing belt PDMS strips were then adhered together using double-sided tape 4610 (3M, 3M415). To increase the adhesion properties of the PDMS, the strips were exposed to 20 W $O_2$ plasma for 25 sec prior to contact with the double-sided tape. To form a closed loop, excess tape was used to overlap the seam 4612 (in between the two layers of PDMS). The following procedure was used to form closed loop treads using micro-patterned PDMS and custom timing belt PDMS strips:

(1) Lay out a 100 mm strip of double-sided tape with backing paper still attached to one side (sticky side up)
(2) Lay out a 95 mm strip of timing belt PDMS (smooth side up)
(3) Expose both strips to 20 W $O_2$ plasma for 25 sec.
(4) Immediately press smooth side of timing belt PDMS to sticky side of tape.
(5) Peel off backing on tape
(6) Expose new sticky side to 20 W $O_2$ plasma for 25 sec
(7) Immediately form closed loop, using the 5 mm excess tape to overlap the seam
(8) Expose the smooth side of a 95 mm long micro-patterned PDMS strip to 20 W $O_2$ plasma for 25 sec
(9) Immediately press smooth side of PDMS onto tape, forming a layer of micro-patterned PDMS on the outside surface of the tread.

This procedure resulted in flexible treads with minimal seam separation. The treads had custom PDMS timing belts 4602B as an inside surface for mechanical engagement with the timing pulleys on the RCE. The treads also featured micro-patterned PDMS 4606 on the outside surface. Eight treads were fabricated in this manner for RCE v2. The treads had a radius of 15 mm, a width of 3 mm, and a thickness of 1.5 mm.

Figure 46C:
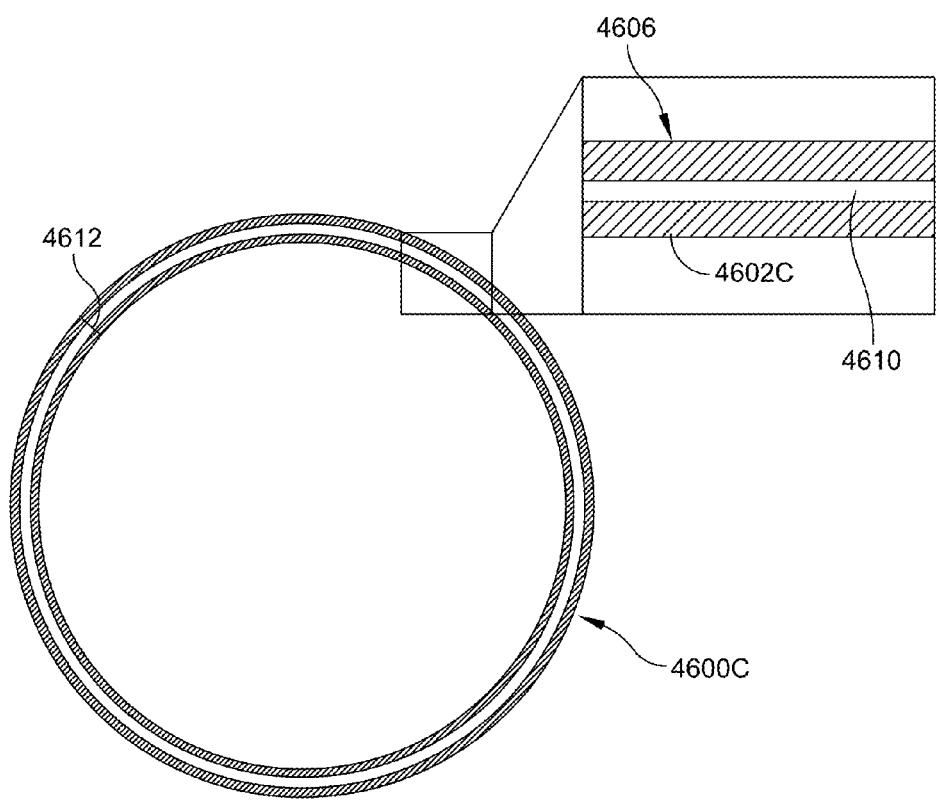

FIG. 46*c* illustrates friction driven PDMS treads 4600C. This third iteration of the tread fabrication was for RCE version 3 (RCE v3), which employed a friction drive system. The friction drive system eliminated the need for timing belts as a mechanical engagement system, enabling a reduction in tread thickness and overall size of the RCE. The design of the RCE required fewer, but wider treads, decreasing the fabrication time and increasing the ease of handling. The treads were fabricated in a similar manner to iteration 2, except the PDMS timing belts were replaced with a thin layer of smooth PDMS 4602C. The thin layer of PDMS 4602C was used to promote friction between the inside surface of the tread and the frictional rollers on the RCE. The following procedure was used to fabricate closed loop treads:

(1) Lay out a 100 mm strip of double-sided tape with backing paper still attached to one side (sticky side up).
(2) Clamp the tape so that 5 mm of the tape is covered.
(3) Paint the remaining uncovered 95 mm of the sticky side with a thin layer of liquid PDMS.
(4) Heat cure the PDMS in an oven at 100° C. for 1 hr
(5) Unclamp the tape and wrap the strip around an 1.5" diameter cylinder (PDMS side down), using the excess 5 mm to overlap the seam.
(6) Peel off the paper backing
(7) Expose the tape and the smooth side of a 95 mm long micro-patterned PDMS strip to 20 W $O_2$ plasma for 25 sec.
(8) Immediately wrap the micro-patterned PDMS strip around the tape (smooth side to tape).
(9) Slide the tread off of the cylinder.

Figure 47:
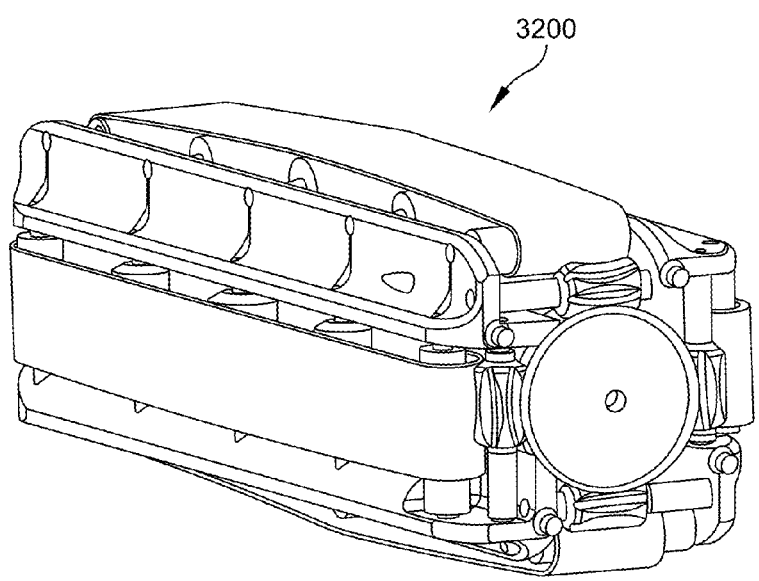
FIG. 47 illustrates a close up view of the back of RCEv3 prototype.

This procedure results in treads with a smooth PDMS inside surface for frictional engagement with the RCE rollers and a micro-patterned PDMS layer on the outside surface of the treads. Four treads were fabricated in this manner for RCE v3. The treads had a radius of 15 mm, a width of 6 mm, and thickness of 0.75 mm. Another view of RCE 3200 is illustrated in FIG. 47.

Figure 48:
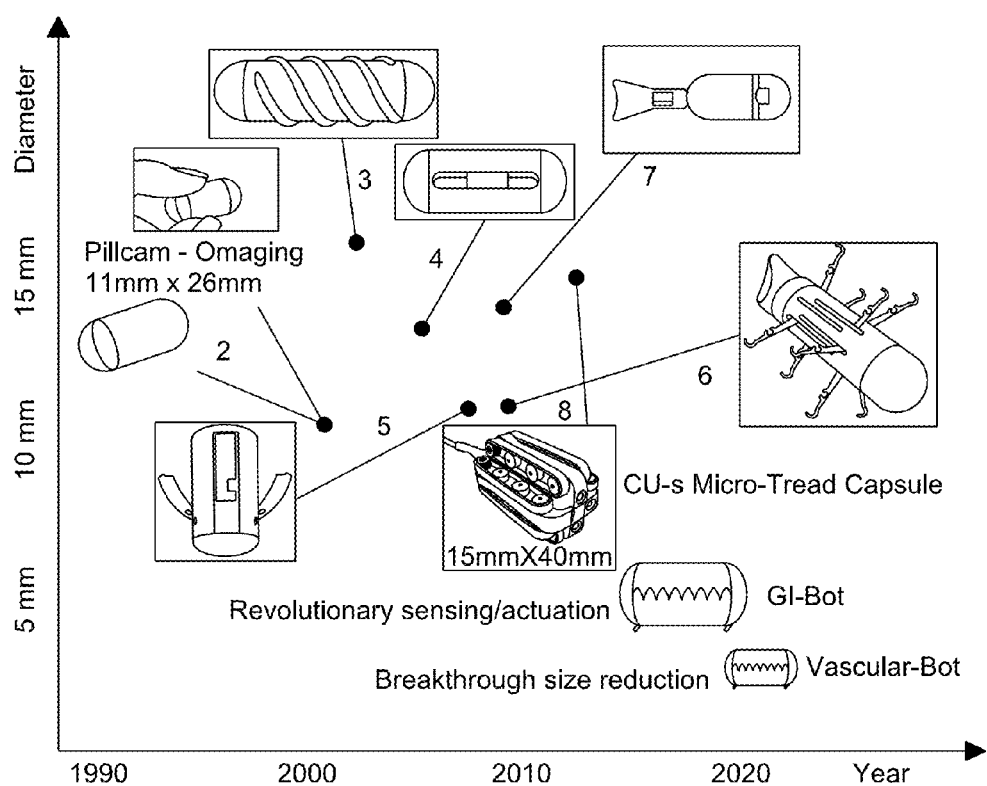
FIG. 48 illustrates an evolution of in vivo micro-robots from Pillcam products, Micro-Tread Capsule, to the transformative GI-Bot and Vascular-Bot.

With reference to FIG. 48, there is shown an evolution of in vivo micro-robots from Pillcam products, Micro-Tread Capsule, to the transformative GI-Bot and Vascular-Bot presents major imaging devices and micro-robots developed for the vision of in vivo micro-robotic non-invasive surgery. The Pillcam announced by Given Imaging in 2001 is the first commercial capsule endoscopy for small bowel visualization and Given's most recent new addition is Bravo for pH monitoring of gastric reflux. (Given Imaging, http://www.given-imaging.com/en-us/Pages/GivenWelcomePage.aspx.) Other research micro-robots, sequenced in FIG. 48, include a magnetically actuated screw-shaped robot (Sendoh, M., Ishiyama, K., and Arai, K.-I. Fabrication of magnetic actuator for use in a capsule endoscope. IEEE Trans. Magnetics, 2003, 39(5), 3232-3234), an anchoring robot using shape-memory actuators, (Kim, B., Lee, S., Park, J. H., and Park, J. Design and fabrication of a locomotive mechanism for capsule-type endoscopes using shape memory alloys (SMAS). IEEE/ASME Trans. Mechatronics, 2005, 10(1), 77-85), an anchoring robot utilizing micro-patterned legs (Glass, P., Cheung, E., and Sitti, M., 2008, "A Legged Anchoring Mechanism for Capsule Endoscopes Using Micropatterned Adhesives". IEEE Transactions on Biomedical Engineering, 55(12), December, pp. 2759-2767), a legged robot for mobility in the large bowel (Quirini, M., Menciassi, A., Scapellato, S., Stefanini, C., and Dario, P. Design and fabrication of a motor legged capsule for the active exploration of the gastrointestinal tract. IEEE/ASME Trans. Mechatronics, 2008, 13(2), 169-179), and tail-enabled robot for mobility in the gastric cavity (E. Morita, N. Ohtsuka, Y. Shindo, S, Nouda, T. Kuramoto, T. Inoue, M. Murano, E. Umegaki, K. Higuchi, 2010, "In vivo trial of a driving system for a self-propelling capsule endoscope using a magnetic field (with video)." Gastrointestinal Endoscopy, 72(4), pp. 836-840), and a mobile robotic capsule endoscope (RCE) that incorporates micro-patterned treads. (Sliker, L., Kern, M., Schoen, J. A., Rentschler, M. E., "Surgical Evaluation of a Novel Robotic Capsule Endoscope using Micro-Patterned Treads," Journal of Surgical Endoscopy, under review (SEND-11-1291.) This mobile RCE developed at the University of Colorado (CU) illustrates an example of the state-of-the-art micro-robots, with our micro-tread technology, and has been used successfully in porcine surgeries. In an embodiment, an RCE may have cross-sectional areas of about: V1: 9.77 square centimeters; V2: 8.23 square centimeters; and V3: 3.61 square centimeters.

Automotive Tread-Surface Interaction

A mobile device moving inside the body can be viewed in the general context of tread-surface interaction. Tread-surface interaction has been studied extensively in the robotics and automotive communities in the context of vehicle-terrain interaction. First attempts to develop a comprehensive theory applicable to all terrains were made at the Land Locomotion Laboratory. (Bekker, M. G., Off the Road Locomotion. Ann Arbor, Mich.: University of Michigan Press, 1960.) In 1967, Onafeko and Reece developed an improved theory for including shear stress with wheel slip during wheel-soil interaction. (Onafeko, O., and Reece, A. R., "Soil Stresses and Deformations Beneath Rigid Wheel," Journal of Terramechanics, 4(1): 59-80, 1967.) Wong and Reece (1967) showed that there are both radial and tangential stresses on the wheel-soil interface. (Wong, J., and Reece, A., "Prediction of Rigid Wheel Performance Based on the Analysis of Soil-Wheel Stresses, Part I. Performance of Driven Rigid Wheels," Journal of Terramechanics, 4(1): 81-98, 1967.) It was also shown that these do not only depend on soil properties and wheel dimensions, but wheel slip as well. Additional work has used analytical models to approximate wheel/soil interaction (Muro, T., "Tractive Performance of a Driven Rigid Wheel on Soft Ground Based on the Analysis of Soil-Wheel Interaction," Journal of Terramechanics, 30(5): 351-369, 1993; and Wulfsohn, D., and Upadhyaya, S., "Traction of Low-Pressure Pneumatic Tires in Deformable Terrain," SAE Transactions, 100(2): 348-363, 1991), as well as finite element methods. (Saliba, J., "Elastic-Viscoplastic Finite-Element Program for Modeling Tire/Soil Interaction," Journal of Aircraft, 27(4): 350-357, 1990; and Hiroma, T., Wanjii, S., Kataoka, T., and Ota, Y., "Stress Analysis Using FEM on Stress Distribution Under a Wheel Considering Friction with Adhesion Between a Wheel and Soil," Journal of Terramechanics, 34(4): 225-233, 1997.)

Passenger car tires are currently designed with an eye on aesthetics and functionality. (Okonieski, R. E., Moseley, D. J., Cai, K. Y, 2003. Simplified approach to calculating geometric stiffness properties of tread pattern elements. Tire Science and Technology 31(3), 132-158.) Most focus however is on the tread element stiffness, which the tread designer monitors as the design evolves. (Okonieski, R. E., Moseley, D. J., Cai, K. Y, 2003. Simplified approach to calculating geometric stiffness properties of tread pattern elements. Tire Science and Technology 31(3), 132-158.) Changes to the tread geometry involve many attributes including the number of sipes, sipe depth, sipe location, block element edge taper, nonskid depth, etc. (Okonieski, R. E., Moseley, D. J., Cai, K. Y, 2003. Simplified approach to calculating geometric stiffness properties of tread pattern elements. Tire Science and Technology 31(3), 132-158.) A number of optimization methods, including neural networks, have been applied for construction of low noise tread profiles, and shapes of tire treads for avoiding lateral slippage. (Becker, M., Szczerbicka, H., Thomas, M., 2007. Neural networks and optimization algorithms applied for construction of low noise tread profiles. Cybernetics and Systems 38(5-6), 535-548; and Ahmed, S. R., Nath, S. K. D., Uddin, M. W., 2005. Optimum shapes of tire-treads for avoiding lateral slippage between tires and roads. International Journal for Numerical Methods in Engineering 64(6), 729-750.) One study developed a method for determining the optimum tread shape for avoiding later slippage between tires and roads. (Ahmed, S. R., Nath, S. K. D., Uddin, M. W., 2005. Optimum shapes of tire-treads for avoiding lateral slippage between tires and roads. International Journal for Numerical Methods in Engineering 64(6), 729-750.) Other work has used FEA to study tread patterns under contact loading. (Ghoreishy, M., 2006. Finite element analysis of the steel-belted radial tire with tread pattern under contact load. Iranian Polymer Journal (English Edition) 15(8), 667-674; Hofstetter, K., Grohs, C., Eberhardsteiner, J., Mang, H. A., 2006. Sliding behaviour of simplified tire tread patterns investigated by means of FEM. Computers & Structures 84(17-18), 1151-63; and Seta, E., Nakajima, Y., Kamegawa, T. Ogawa, H., 2000. Hydroplaning analysis by FEM and FVM: effect of tire rolling and tire pattern on hydroplaning. Tire Science and Technology 28(3), 140-156.) This research has included studying the effect of steel-belted radial tires on contact loading, sliding behavior of simplified tire tread patterns, and the effects of tire rolling and tire pattern on hydroplaning.

Figure 49:
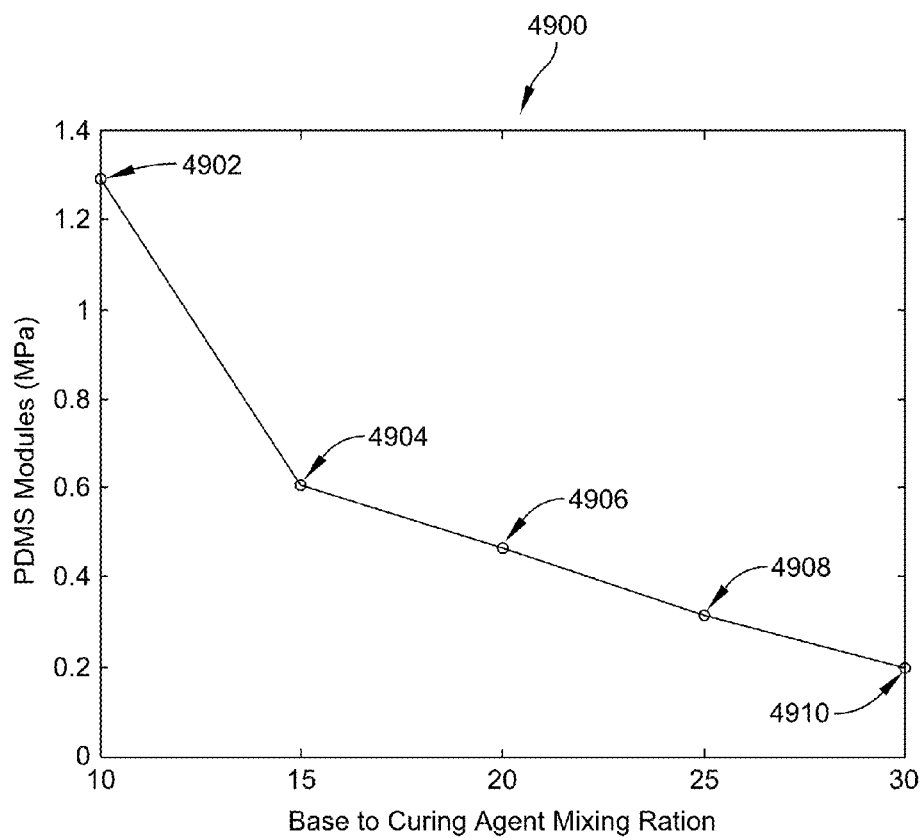
FIG. 49 illustrates five different moduli that were obtained for the PDMS treads by varying the base to curing agent mixing ratio during polymer fabrication; higher concentration of curing agent resulted in higher PDMS modulus; the modulus was varied between 0.2 MPa and 1.3 MPa; the relationship between mixing ratio and PDMS modulus is a decaying exponential; this created a large gap between 0.6 MPa and 1.3 MPa with a linear variation in mixing ratios.
Figure 50:
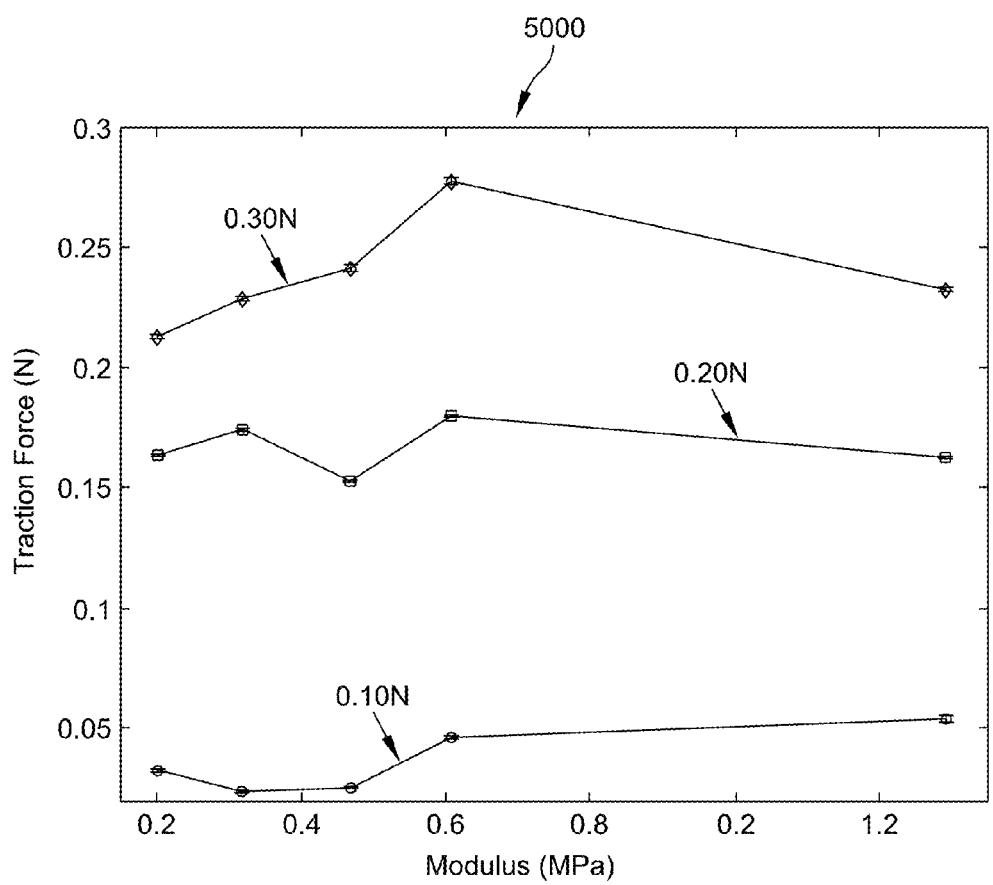
FIG. 50 illustrates the effect of PDMS modulus on traction force for multiple normal forces (0.10 N, 0.2 N, and 0.3 N); this data was performed using the equally spaced circular pillar micro-pattern on dry synthetic tissue at a slip ratio of 0.2 and a translational speed of 6 mm/s.
Figure 51:
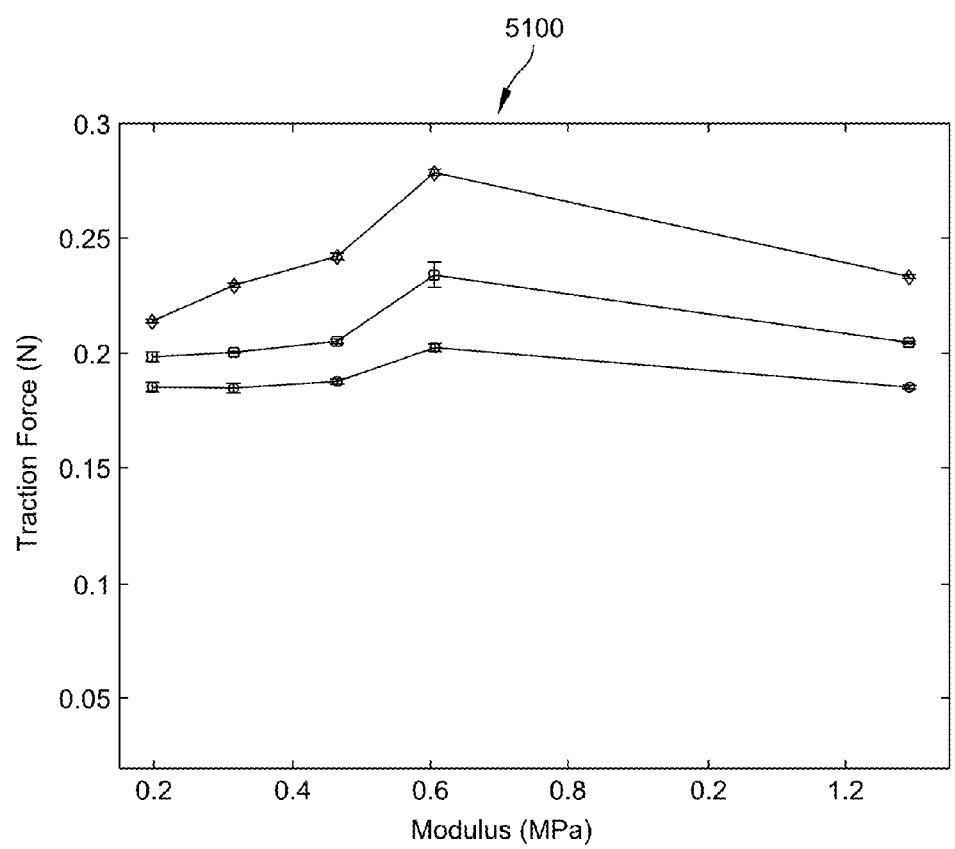
FIG. 51 illustrates the effect of PDMS modulus on traction force for multiple translational speeds (2 mm/s, 3 mm/s, and 6 mm/s); this data was performed using the equally spaced circular pillar micro-pattern on dry synthetic tissue at a slip ratio of 0.2 and a normal force of 0.3 N.

The effect of varying PDMS modulus on traction force was explored and the results are summarized in FIGS. 50 and 51. The experiment (illustrated in graph 4900) included 5 different pillar moduli 4902, 4904, 4906, 4908, 4910, obtained by varying the base to curing agent mixing ratio of the PDMS during polymer fabrication (FIG. 49). As the concentration of curing agent is increased (concentration of base is decreased), the end modulus increases. The relationship between mixing ratio and PMDS (pillar) modulus takes the form of a decaying exponential. In these experiments, a linear progression of mixing ratios was used (10:1, 15:1, 20:1, 25:1, 30:1), which created a large gap between 0.6 MPa and 1.3 MPa. Future tests will include more mixing ratios between 10:1 and 15:1 to produce sample Moduli in the range of 0.6 MPa to 1.3 MPa.

Results shown in FIGS. 50 and 51 were conducted using the equally-spaced circular pillar micro-patterned tread on dry synthetic tissue (TSC-10, Simulab, Seattle, Wash., USA). Tests were repeated on synthetic tissue hydrated with 0.9% PBS, and similar trends were observed. FIG. 50 is a graph 5000 illustrative of the effect of varying pillar modulus on traction force for three different normal forces (0.10 N, 0.20 N, and 0.30 N) at a slip ratio of 0.2 and a translational speed of 6 mm/s. FIG. 51 is a graph 5100 illustrative of the effect of varying pillar modulus on traction force for three different translational speeds (2 mm/s, 3 mm/s, and 6 mm/s) at a slip ratio of 0.2 and a normal force of 0.30 N. Therefore, the 0.30 N line (green) in FIG. 50, and the 6 mm/s line (green) in FIG. 51 represent the same data. The same effect of increasing pillar modulus is shown in both plots. It seems that there is an optimal modulus for traction force near 0.6 MPa, however, this cannot be confirmed as more tests need to be completed in the range of 0.6 MPa to 1.3 MPa. It appears that traction force increases and then decreases in the range of 0.2 MPa to 1.3 MPa, but the maximum is not clear due to the lack of data points between 0.6 MPa and 1.3 MPa.

The effect of varying normal force on traction force is shown in FIG. 50. As normal force is increased traction force is also increased. This is intuitive when referring to Coulomb friction, $F_f \leq \mu F_N$, where $F_f$ is the frictional force of the micro-patterned tread on the dry synthetic tissue, $F_N$ is the normal force of the robot, and $\mu$ is the coefficient of friction between the robot tread and the dry synthetic tissue. The effect of varying translational speed on traction force is shown in FIG. 51. As translational speed increases traction force is also increased. This is due to the strain rate hardening of the synthetic tissue, which is an inherent property of viscoelastic materials. The effective stiffness of the tissue depends on the rate of force application. As the substrate becomes more stiff, less energy is lost and traction is increased.

Figure 52:
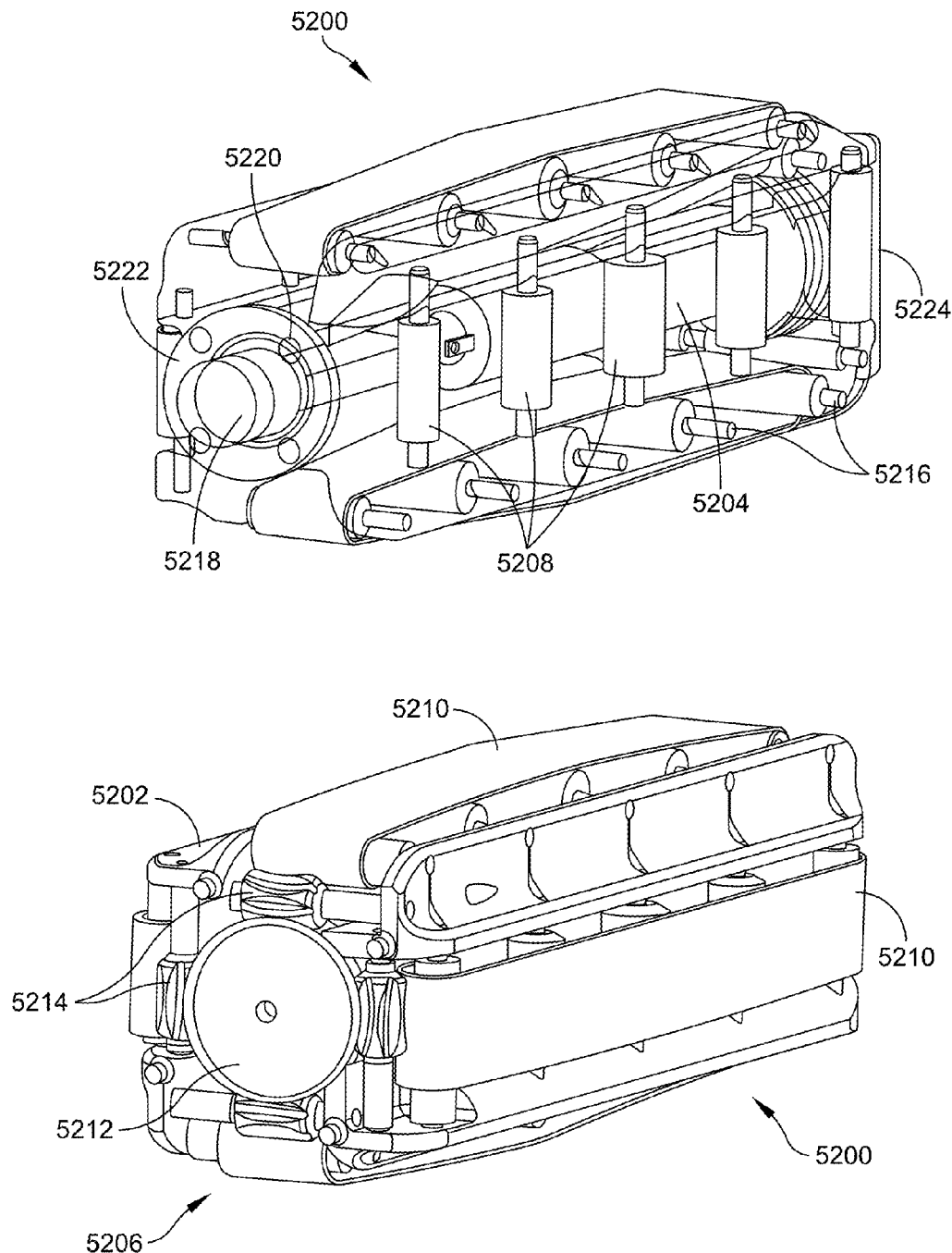
FIG. 52 illustrates two assembly views of the RCE V3 device with the upper left image as a front isometric view and the lower right image as a rear isometric view with the end cap removed to show the geared drive train.

With reference to FIG. 52, and in an embodiment, there is illustrated the RCE V3 5200 with an outer housing 5202 for a centrally located, planetary geared, DC motor 5204 (Faulhaber, Clearwater, Fla.), a custom designed geared drive train 5206, and a series of rollers 5208 for the micro-patterned PDMS treads 5210 to pass over as the RCE 5200 moves. A custom designed worm 5212 (pitch diameter of 0.0787 in and modulus* of 0.013) is press fit and adhered to the shaft of the DC motor 5204 with a 5 Minute® Epoxy (ITW Devcon, Danvers, Mass.). The worm 5212 drives four mating worm gears 5214 (6 teeth, modulus of 0.013 (modulus calculated as the inverse of the diametral pitch), and pitch diameter of 1.99 mm) that are equally spaced, radially around the worm 5212. Four adjacent shafts 5216 also have cylindrical rollers 5208 (outer diameter of 2.30 mm and length of 8.38 mm) to drive the four PDMS treads (approximately 6 mm wide and 0.75 mm thick). The rollers along the body of the housing have various outer diameters to make the shape of the device more rounded. The shafts for the gears and rollers are made from 1 mm drill bit shanks and are approximately 12 mm long. The device also has a centrally located 4 mm diameter video camera 5218 (Bangu Technology Development Company Limited, Baoan District Shenzhen Guangdong, China) with 30 fps and four 2 mm diameter, yellow LEDs 5220 (Digi-Key Corporation, Thief River Falls, Minn.) embedded in a front cap 52222 to view and illuminate the bowel. A clear piece of plastic (not illustrated) is adhered to the front cap 5222 to prevent any fluids from entering the device 5200 and damaging the internal electronic components. An end cap 5224 is adhered to the rear of the device to protect the geared drive train 5206.

In an embodiment, housing 5202, gears 5214, tread rollers 5208, front cap 5222 and end cap 5224 may be rapid prototyped using an Objet 30 (Objet, Billerica, Mass.) machine and an Objet VeroWhitePlus™ (Objet, Billerica, Mass.) resin. The housing has a 2.89 mm² cross-sectional area and is approximately 58.16 mm long. The micro-patterned PDMS treads 5210 are custom fabricated from Polydimethylsiloxane, a silicone based polymer with viscoelastic properties. The micro-pattern consists of equally spaced circular pillars that have a center-to-center distance of 245 μm and a diameter of 140 μm. The assembled RCE V3 device has an approximate cross-sectional area of 3.61 cm² and a weight of 30 g.

What is claimed is:

1. A micro-patterned tread for a robotic capsule endoscope, the micro-patterned tread comprising:
    a first side and a second side of the micro-patterned treat tread, the first side and the second side in opposition to one another;
    a micro-patterned surface disposed on the first side in a direction extending outwardly from the second side;
    a roller engaging surface disposed on the second side in a direction extending outwardly from the first side;
    a first layer having the first side with the micro-patterned surface thereon, the first layer including a molded surface and a non-molded surface in opposition to one another, the molded surface including PDMS molded to form the micro-pattern surface, wherein the first layer is formed in a first mold;
    a second layer having the second side with the roller engaging surface thereon, the second layer including a molded surface and a non-molded surface in opposition to one another, the molded surface including PDMS molded to form the roller engaging surface, wherein the second layer is formed within a second mold; and
    an adhesive configured to join the first layer and the second layer together with the non-molded surface of the first layer and the non-molded surface of the second layer joined together so as to dispose the first side and the second side in opposition to one another.

2. The tread of claim 1, wherein the tread has a micro-pattern of pillars with a diameter of about 140 μm.

3. The tread of claim 2, wherein the pillars of the tread have a height of 70 μm.

4. The tread of claim 3, wherein the pillars of the tread are circular.

5. The tread of claim 4, wherein the pillars of the tread are equally spaced with a center-to-center distance of 245 μm.

6. The tread of claim 2, wherein the pillars of the tread are circular.

7. The tread of claim 2, wherein the pillars of the tread are square.

8. The tread of claim 2, wherein the pillars of the tread are diamond.

9. The tread of claim 2, wherein the pillars of the tread are equally spaced with a center-to-center distance of 245 μm.

10. The tread of claim 9, wherein the pillars of the tread form gaps of a distance of about 105 μm therebetween.

11. The tread of claim 2, wherein the pillars of the tread form a gap to diameter ratio of about 0.75.

12. The tread of claim 1, wherein the tread has a micro-pattern of pillars with each pillar having a diameter of less than 200 μm.

13. The tread of claim 12, wherein the pillars have a height to width aspect ratio of 1:2.

14. The tread of claim 1, wherein the tread has a micro-pattern of pillars with each pillar having a height of about 70 μm.

15. The tread of claim 1, wherein the pillars have a height to width aspect ratio of 1:2.

16. The tread of claim 1, wherein the pillars have a height to width aspect ratio within a range of about 1:4 to about 2:1.

17. The tread of claim 1, wherein the first side comprises PDMS.

18. The tread of claim 1, wherein the second side comprises PDMS.

19. The tread of claim 1, wherein the second side comprises a smooth layer of PDMS configured to frictionally engage rollers of the robotic capsule endoscope.

20. The tread of claim 1, further comprising a titanium layer disposed on the non-molded surface of the first layer.

21. The tread of claim 20, wherein the adhesive comprises a double sided tape between the titanium layer and the non molded surface of the second layer.

22. The tread of claim 20, wherein the second side of the tread includes a timing belt and wherein the timing belt is configured to engage timing pulleys of the robotic capsule endoscope.

23. The tread of claim 1, further comprising a tread seam configured to join opposing ends of the tread to one another so as to form a continuous surface along the first side and a continuous surface along the second side.

* * * * *